United States Patent
Jiaang et al.

(10) Patent No.: US 9,255,072 B2
(45) Date of Patent: Feb. 9, 2016

(54) PYRAZOLE COMPOUNDS AND THIAZOLE COMPOUNDS AS PROTEIN KINASES INHIBITORS

(75) Inventors: Weir-Torn Jiaang, Taichung (TW); Tsu-An Hsu, Taipei (TW); Wen-Hsing Lin, Miaoli County (TW); Yu-Sheng Chao, New York, NY (US)

(73) Assignee: National Health Rsearch Institutes, Zhunan Town (TW)

( * ) Notice: Subject to any disclaimer, the term of this patent is extended or adjusted under 35 U.S.C. 154(b) by 88 days.

(21) Appl. No.: 13/409,624

(22) Filed: Mar. 1, 2012

(65) Prior Publication Data

US 2012/0225880 A1 Sep. 6, 2012

Related U.S. Application Data

(60) Provisional application No. 61/449,245, filed on Mar. 4, 2011.

(51) Int. Cl.

| | | |
|---|---|---|
| *C07D 231/40* | (2006.01) | |
| *C07D 403/12* | (2006.01) | |
| *C07D 413/14* | (2006.01) | |
| *C07D 401/12* | (2006.01) | |
| *C07D 413/12* | (2006.01) | |
| *C07D 417/12* | (2006.01) | |
| *C07D 417/14* | (2006.01) | |
| *A61K 31/496* | (2006.01) | |
| *A61K 31/5377* | (2006.01) | |
| *A61K 31/506* | (2006.01) | |
| *C12N 9/12* | (2006.01) | |

(52) U.S. Cl.
CPC ............ *C07D 231/40* (2013.01); *C07D 401/12* (2013.01); *C07D 403/12* (2013.01); *C07D 413/12* (2013.01); *C07D 413/14* (2013.01); *C07D 417/12* (2013.01); *C07D 417/14* (2013.01); *C12N 9/12* (2013.01); *C12N 9/1205* (2013.01); *C12Y 207/01112* (2013.01)

(58) Field of Classification Search
None
See application file for complete search history.

(56) References Cited

U.S. PATENT DOCUMENTS

| | | | |
|---|---|---|---|
| 7,795,288 B2 | 9/2010 | Bold | |
| 8,455,658 B2 * | 6/2013 | Vo et al. | ........................ 548/200 |
| 2006/0148822 A1 * | 7/2006 | Bloomfield et al. | ..... 514/255.05 |

FOREIGN PATENT DOCUMENTS

| | | | | |
|---|---|---|---|---|
| WO | WO 01/17995 | * | 3/2001 | .................... 548/200 |
| WO | 2004/108136 | | 12/2004 | |
| WO | 2005/074922 | | 8/2005 | |
| WO | 2008/075068 | | 6/2008 | |

OTHER PUBLICATIONS

Ito, Nobuyuki. Cancer Science 94(1), (2003) 3-8.*
Database Registry Chemical Abstracts Service, Columbus, Ohio, Accession No. RN 436850-69-0, Entered STN: Jul. 3, 2002.*

* cited by examiner

*Primary Examiner* — Samantha Shterengarts
(74) *Attorney, Agent, or Firm* — Cesari and McKenna, LLP

(57) ABSTRACT

A compound of formula (I):

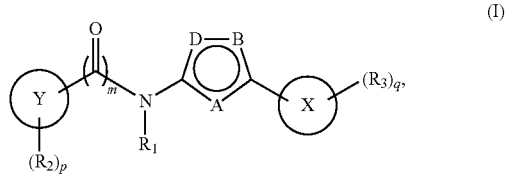

wherein A, B, D, X, Y, $R_1$, $R_2$, $R_3$, m, p, and q are defined herein. Also disclosed is a method for inhibiting FMS-like tyrosine kinase 3, aurora kinase, or vascular endothelial growth factor receptor.

14 Claims, No Drawings

PYRAZOLE COMPOUNDS AND THIAZOLE COMPOUNDS AS PROTEIN KINASES INHIBITORS

CROSS REFERENCE TO RELATED APPLICATIONS

This application claims priority to U.S. Provisional Application No. 61/449,245, filed on Mar. 4, 2011, the contents of which are hereby incorporated by reference.

BACKGROUND

Protein kinases play important roles in cellular signal pathways that regulate various cell functions such as differentiation, proliferation, migration and apoptosis. Deregulation of protein kinases is implicated in a number of diseases including cancer.

FMS-like tyrosine kinase 3 ("FLT3"), vascular endothelial growth factor ("VEGF") receptor, and aurora kinase, are three common protein kinases.

FLT3 is a receptor tyrosine kinase. Mutations of FLT3 can lead to development of cancer, e.g., acute myeloid leukemia. See Pratz et al., *Current Drug Targets,* 2010, 11(7), 781-9.

VEGF is a signal protein produced by cells that stimulates the growth of new blood vessels. It stimulates cellular responses by binding to a tyrosine kinase receptor, i.e., VEGF receptor ("VEGFR"), on the cell surface, causing it to dimerize and become activated through transphosphorylation. VEGFR has been identified as the predominant regulator of tumor angiogenesis. See Hicklin et al., *J Clin Oncol.,* 2005, 23, 1011-1027.

Aurora kinases are essential for cell proliferation. Defects in these kinases lead to severe mitotic abnormality, a condition which is highly associated with tumorigenesis. See Fu et al., Mol. Cancer Res., 2007, 5, 1-10.

These three protein kinases are attractive therapeutic targets in cancer treatment.

SUMMARY

This invention is based on the discovery that certain pyrazole compounds and thiazole compounds can be used to inhibit the activity of FLT3, VEGFR and aurora kinase.

One aspect of this invention relates to a compound of formula (I):

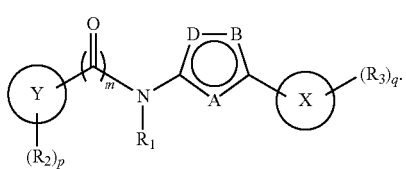

(I)

In this formula, each of A, B, and D, independently, is N, S, O, NR, or CR and at least one of them is N, in which R is H, alkyl, or C(O)OR$_f$, and R' is H, halo, alkyl, haloalkyl, cyclyl, heteroalkyl, heterocyclyl, aryl, or heteroaryl, R$_f$ being C$_1$-C$_{12}$ alkyl, aryl, cycloalkyl, or heteroaryl; each of X and Y, independently, is arylene or heteroarylene; R$_1$ is H, alkyl, haloalkyl, heteroalkyl, cyclyl, heterocyclyl, aryl, or heteroaryl; each of R$_2$ and R$_3$, independently, is alkyl, alkenyl, alkynyl, heteroalkyl, haloalkyl, alkoxyalkyl, hydroxyalkyl, cyclyl, heterocyclyl, aryl, heteroaryl, halo, nitro, cyano, amino, hydroxy, alkoxy, aryloxy, C(O)R$_a$, C(O)OR$_a$, C(O)NR$_a$R$_b$, CR$_a$R$_b$NR$_c$R$_d$, CR$_a$R$_b$NR$_c$C(O)NR$_d$R$_e$, CR$_a$R$_b$NR$_c$C(O)OR$_d$, CR$_a$R$_b$NR$_c$C(O)NR$_d$R$_e$, CR$_a$R$_b$NR$_c$S(O)R$_d$, CR$_a$R$_b$NR$_c$S(O$_2$)R$_d$, NR$_a$R$_b$, NR$_a$C(O)NR$_b$R$_c$, NR$_a$S(O)R$_b$, NR$_a$S(O$_2$)R$_b$, NR$_a$C(O)R$_b$, NR$_a$C(O)OR$_b$, S(O)R$_a$, S(O$_2$)R$_a$, S(O)NR$_a$R$_b$, or S(O$_2$)NR$_a$R$_b$, in which each of R$_a$, R$_b$, R$_c$, R$_d$, and R$_e$, independently, is H, alkyl, heteroalkyl, cyclyl, heterocyclyl, aryl, heteroaryl, arylalkyl, or heteroalkyl; m is 0 or 1; p is 0, 1, 2, 3, 4 or 5; and q is 0, 1, 2, 3, 4, or 5.

One subset of the just-described compounds includes pyrazole compounds in which A is CR', B is N or NR, and D is N or NR. In these compounds, when m is 1, X and Y can be arylene (e.g., phenyl), and R$_1$ can be H; when m is 0, X can be arylene (e.g., phenyl), Y can be heteroarylene (e.g., pyrimidine), and R$_1$ can be H. This subset also includes compounds in which A is CH, B is N or NR, and D is N or NR, wherein R being C(O)OR$_f$, R$_f$ being C$_1$-C$_{12}$ alkyl, aryl, cycloalkyl, or heteroaryl.

Another subset of the compounds described above are thiazole compounds in which A is S, B is CR', and D is N. In these compounds, when m is 1, X and Y can be arylene (e.g., phenyl), and R$_1$ can be H; when m is 0, R$_1$ can be H, X can be arylene (e.g., phenyl), and Y can be heteroarylene (e.g., pyrimidine).

The term "alkyl" refers to a straight or branched monovalent hydrocarbon containing, unless otherwise stated, 1-20 carbon atoms (e.g., C$_1$-C$_{10}$). Examples of alkyl include, but are not limited to, methyl, ethyl, n-propyl, i-propyl, n-butyl, i-butyl, and t-butyl. The term "alkenyl" refers to a straight or branched monovalent or bivalent hydrocarbon containing 2-20 carbon atoms (e.g., C$_2$-C$_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., C$_2$-C$_{10}$) and one or more triple bonds. Examples of alkynyl include, but are not limited to, ethynyl, ethynylene, 1-propynyl, 1- and 2-butynyl, and 1-methyl-2-butynyl. The term "alkoxy" refers to an —O-alkyl. Examples of alkoxy include, but are not limited to, methoxy, ethoxy, n-propoxy, isopropoxy, n-butoxy, iso-butoxy, sec-butoxy, and tert-butoxy. The term "amino" refers to NH$_2$, alkylamino, or arylamino. The term "aryloxy" refers to an —O-aryl. The term "alkoxyalkyl" refers to an alkyl group substituted with one or more alkoxy groups. The term "halo" refers to any radical of fluorine, chlorine, bromine or iodine. The term "haloalkyl" refers to an alkyl group substituted with one or more halo groups. The term "hydroxyalkyl" refers to an alkyl group substituted with one or more hydroxy groups. The term "heteroalkyl" refers to an alkyl group substituted with one or more hetero groups.

The term "cyclyl" refers to a saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl. The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, and tetrahydrofuranyl.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl.

The term "arylene" refers to a bivalent 6-carbon monocyclic, 10-carbon bicyclic, 14-carbon tricyclic aromatic ring system. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, alkoxy, aryloxy, alkoxyalkyl, amino, halo, haloalkyl, hydroxyalkyl, heteroalkyl, cyclyl, heterocyclyl, aryl, heteroaryl, arylene and heteroarylene mentioned herein include both substituted and unsubstituted moieties. Possible substituents on alkyl, alkenyl, alkynyl, alkoxy, aryloxy, alkoxyalkyl, amino, halo, haloalkyl, hydroxyalkyl, heteroalkyl, cyclyl, heterocyclyl, aryl, heteroaryl, arylene and heteroarylene include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, aryloxy, carbamido, carbamyl (—C(O)NH$_2$), carboxyl (—COOH), and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The compounds described above include the compounds themselves, as well as their salts, their solvates, and their prodrugs, if applicable. A salt, for example, can be formed between an anion and a positively charged group (e.g., amino) on a pyrazole compound or a thiazole compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a pyrazole compound or a thiazole compound. Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds as described above. In particular, carbamoyl derivatives of the pyrazole compounds of this invention, with the structures shown below, can be used as prodrugs:

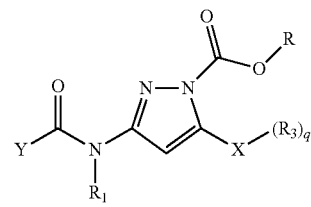

R represents a straight or branched $C_1$-$C_{12}$ alkyl, an aryl, a cycloalkyl, or a heteroaryl group.

The compounds can be used to inhibit FLT3, aurora kinase, or VEGFR either in vitro (e.g., research use) or in vivo (e.g., cancer treatment).

Also within the scope of this invention is a pharmaceutical composition containing one or more of the compounds of formula (I) described above, which can be used in cancer treatment, and the use of such a composition for the manufacture of a medicament for treating cancer.

The details of one or more embodiments of the invention are set forth in the description below. Other features, objects, and advantages of the invention will be apparent from the description of examples and also from the appending claims.

DETAILED DESCRIPTION

Shown below are exemplary compounds of this invention:

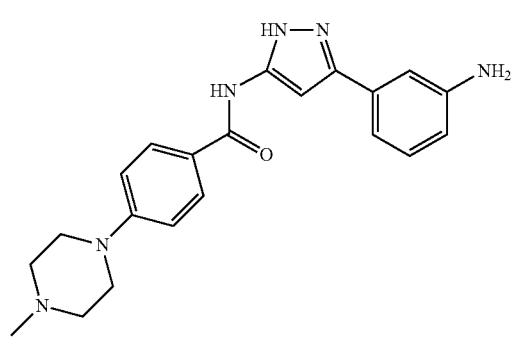

1

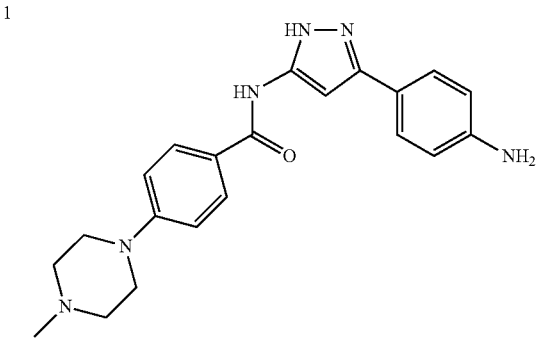

2

-continued
3
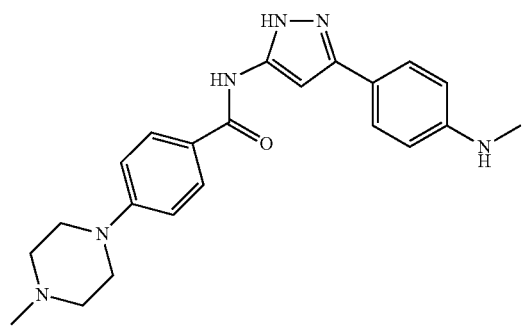
4
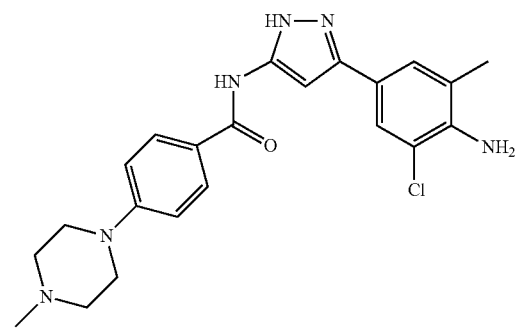
5
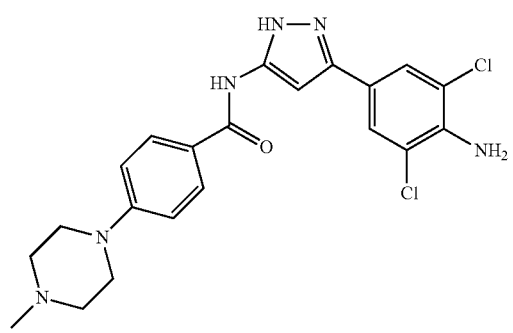
6
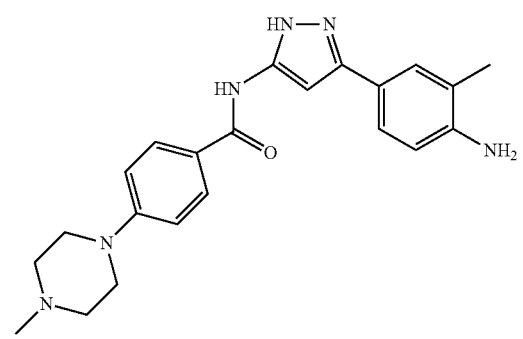
7
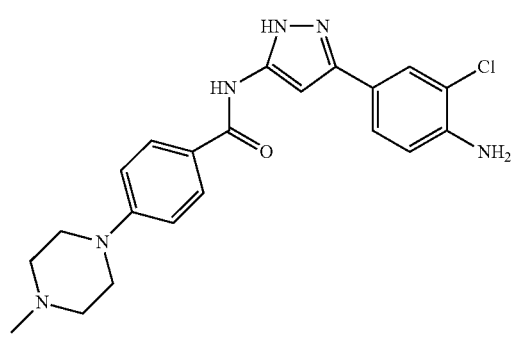
8
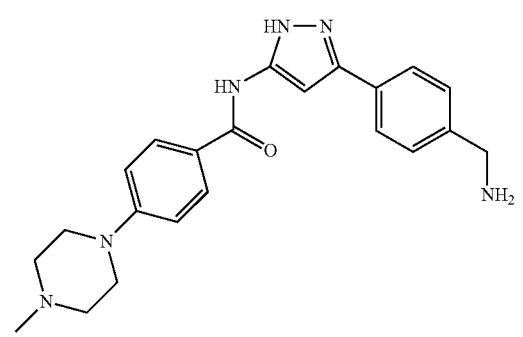
9
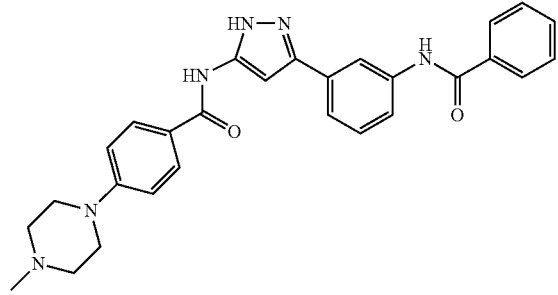
10
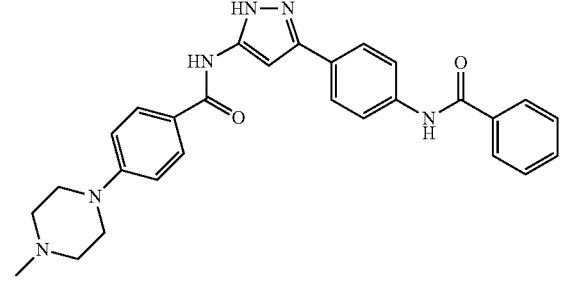
11
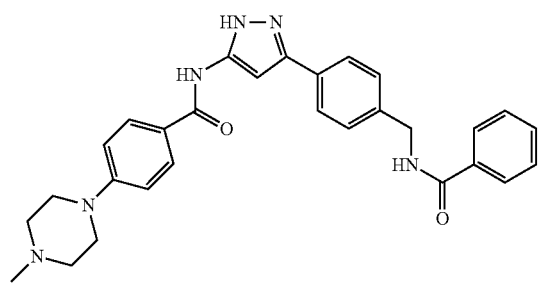
12
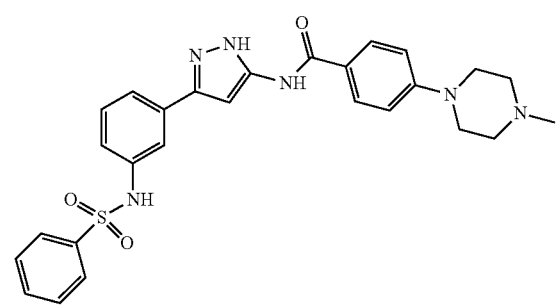

-continued
13
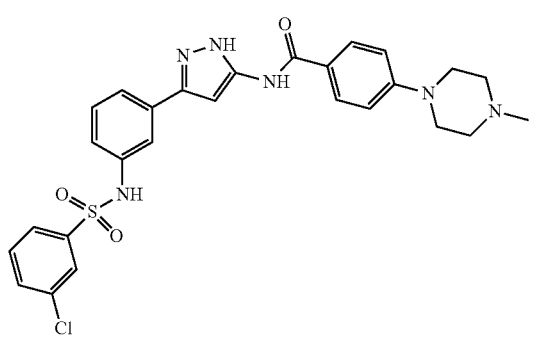
14
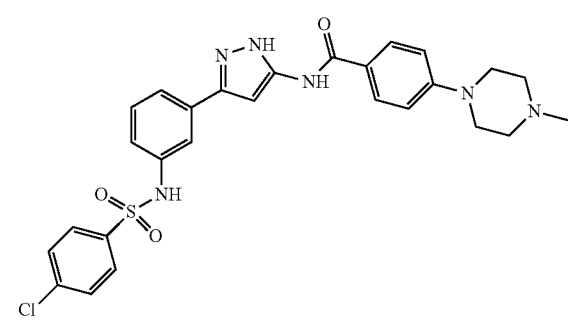
15
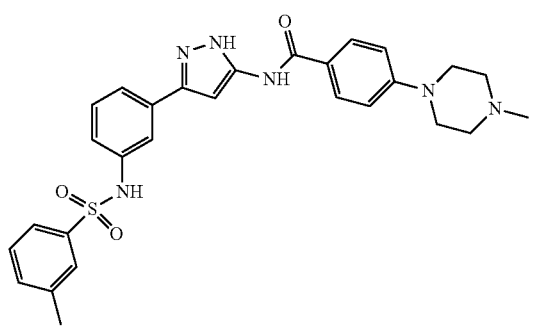
16
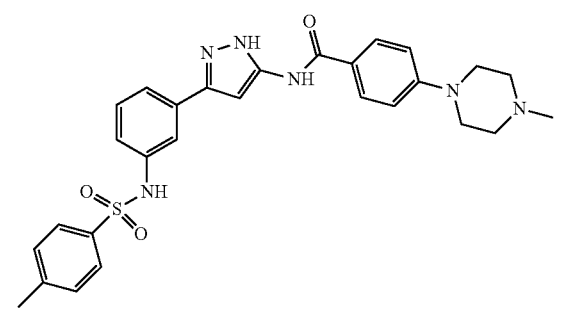
17
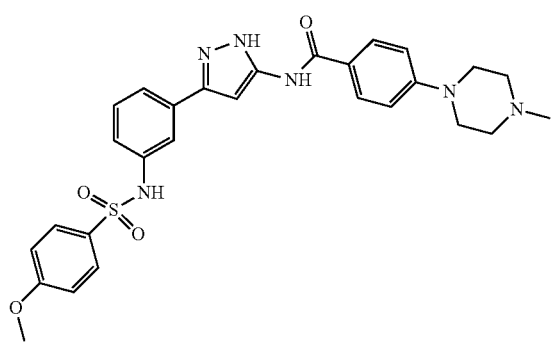
18
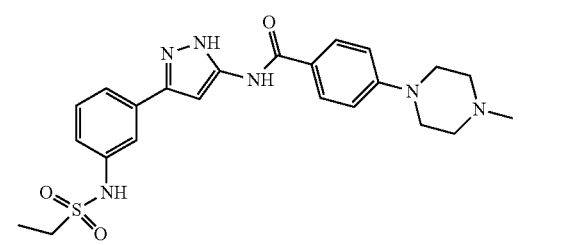
19
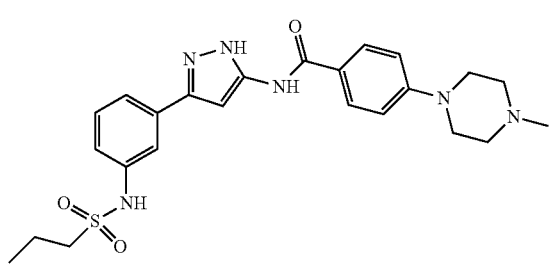
20
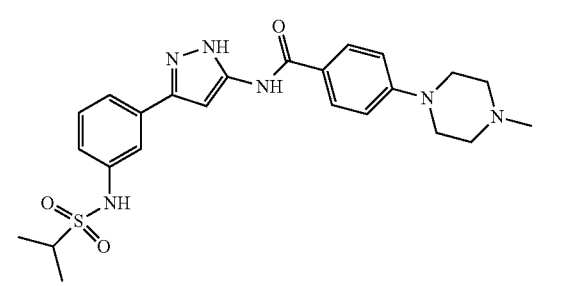

-continued
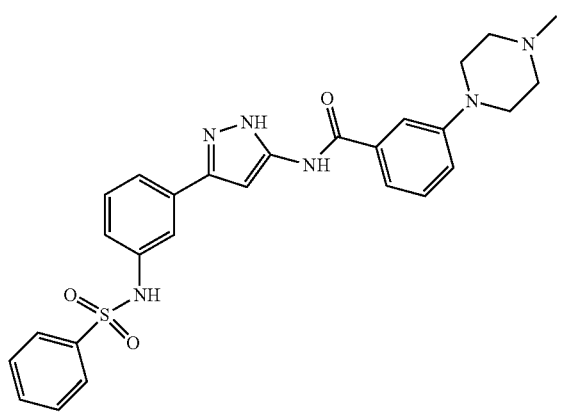
21
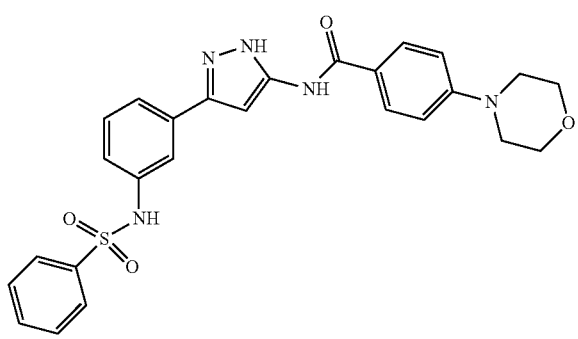
22
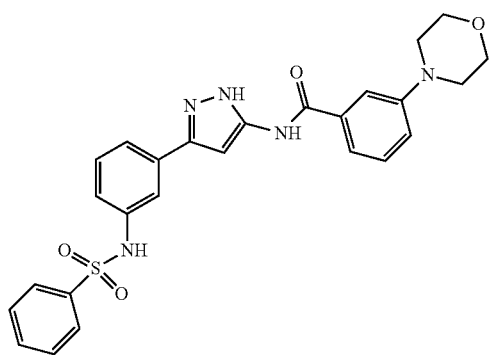
23
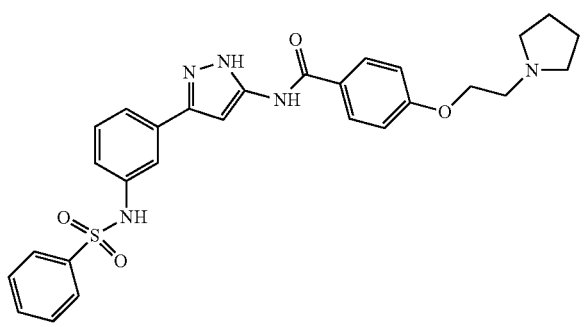
24
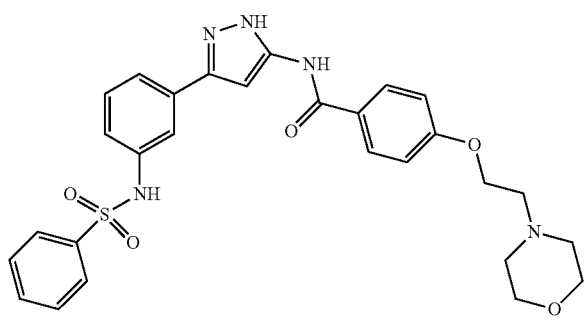
25
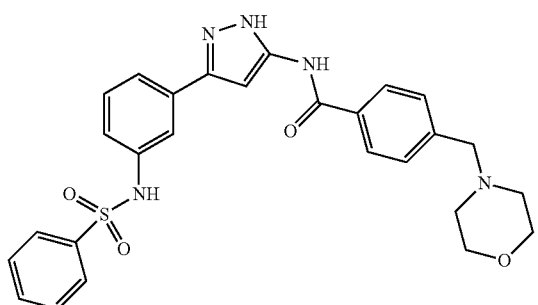
26
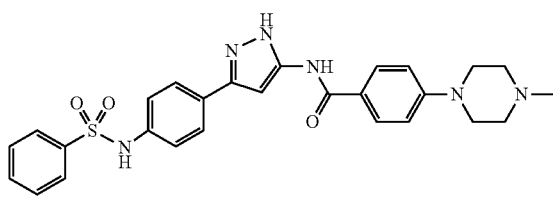
27
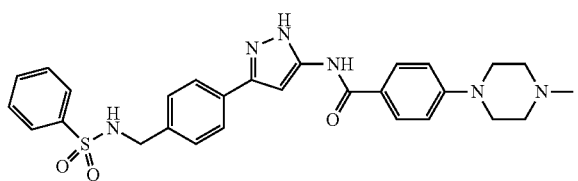
28

-continued
29
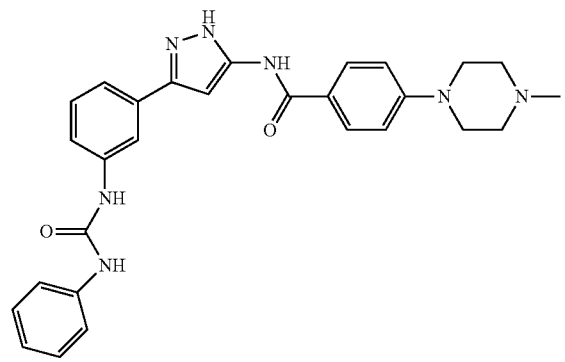
30
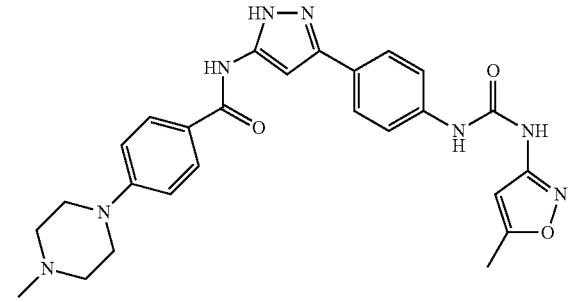
31
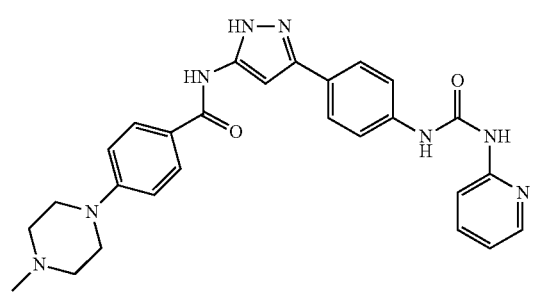
32
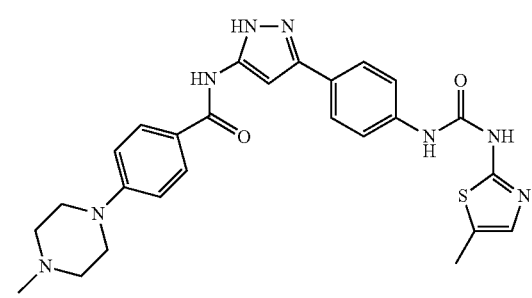
33
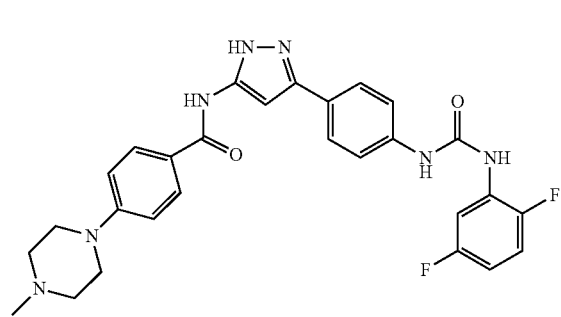
34
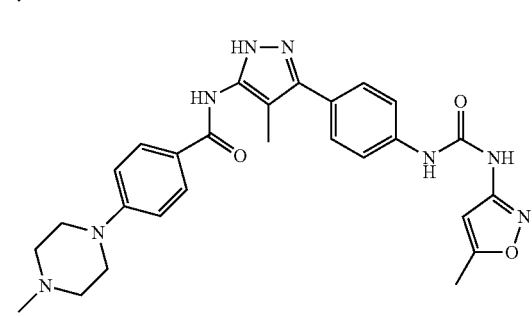
35
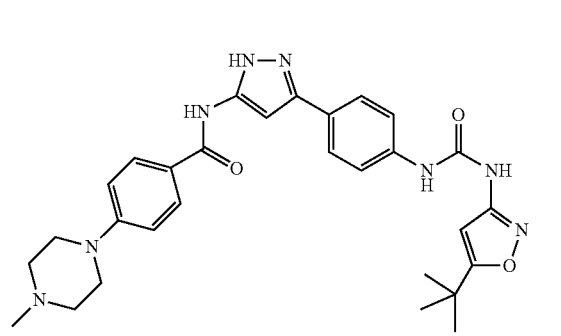
36
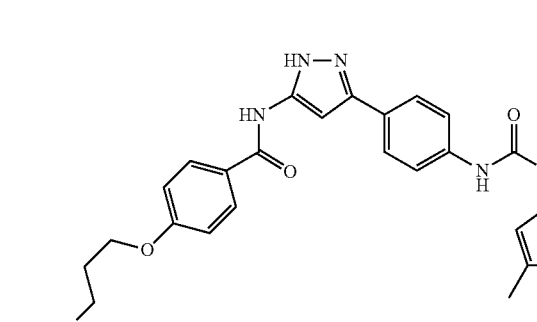
37
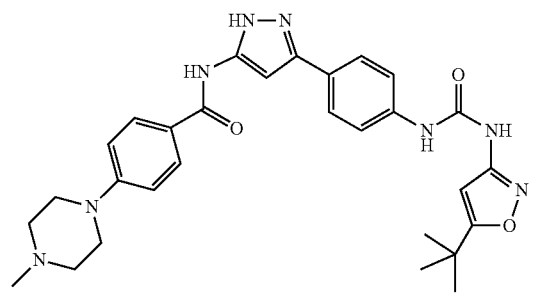
38
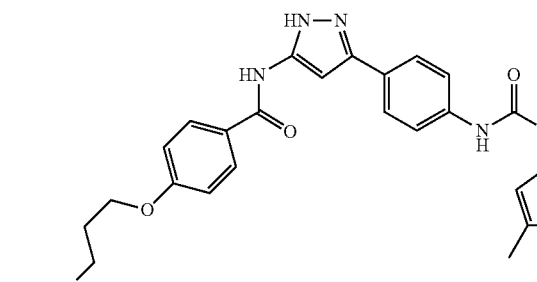

-continued
39
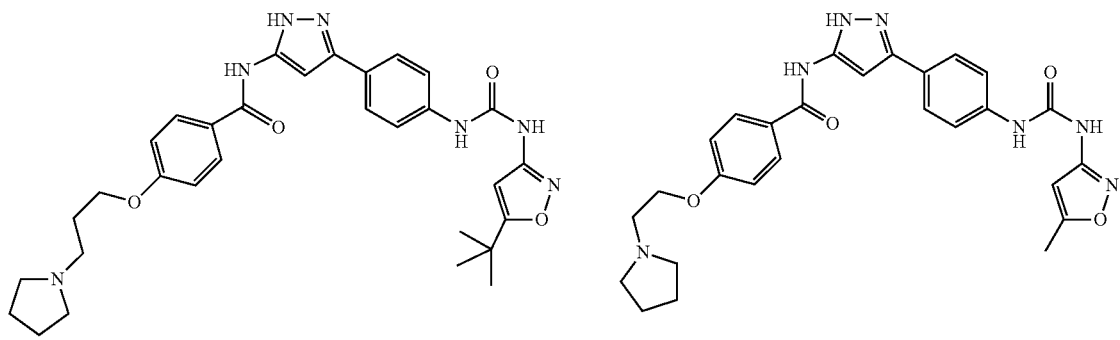
40
41
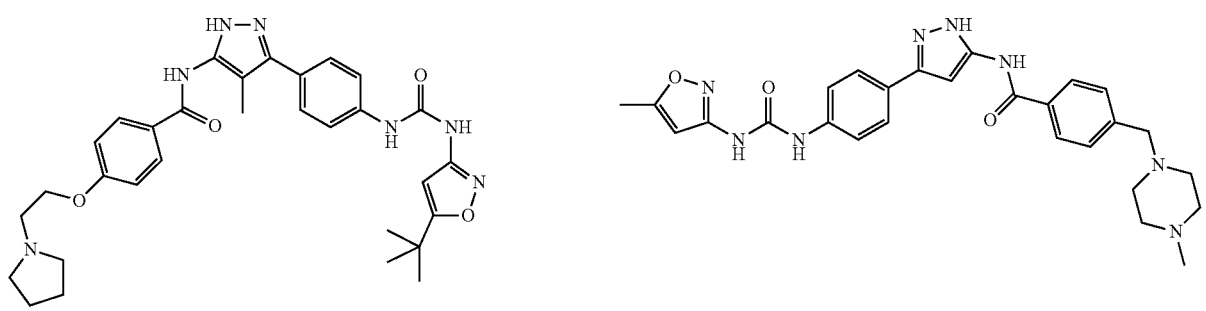
42
43
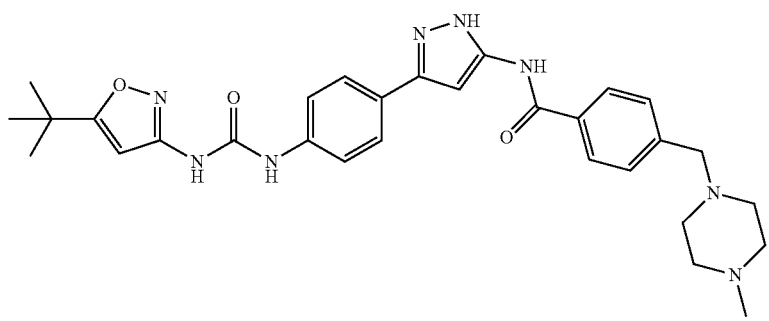
44
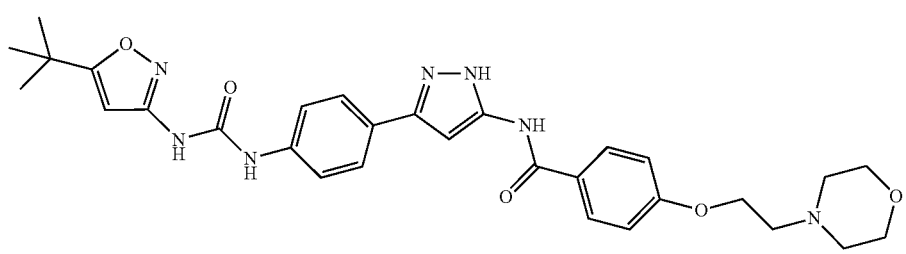
45
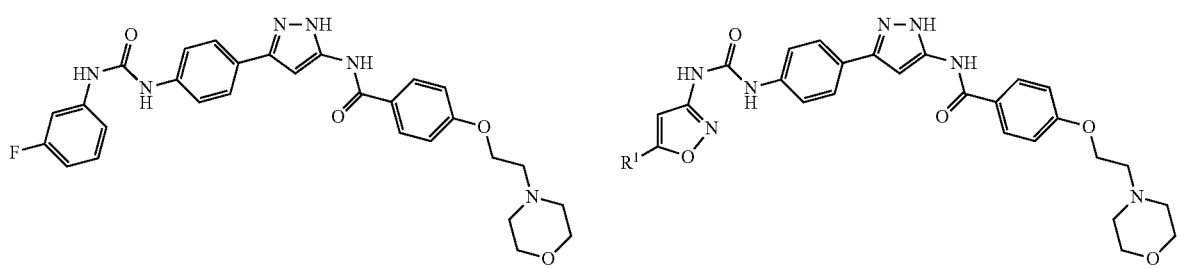
46a R¹ = CH₃, R² = H
46b R¹ = C₂H₅, R² = CH₃
46c R¹ = cyclopropyl, R² = CH₃

-continued
47
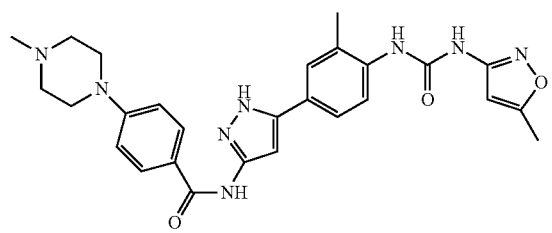
48
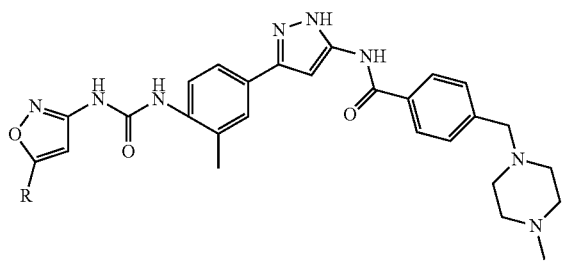
48a R = CH₃
48b R = C₂H₅
49
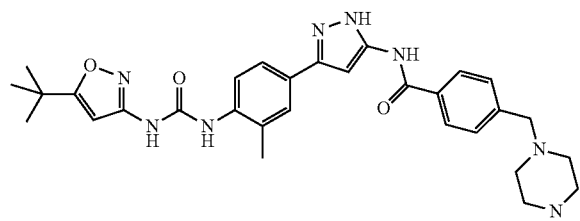
50
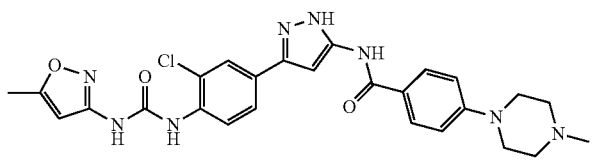
51
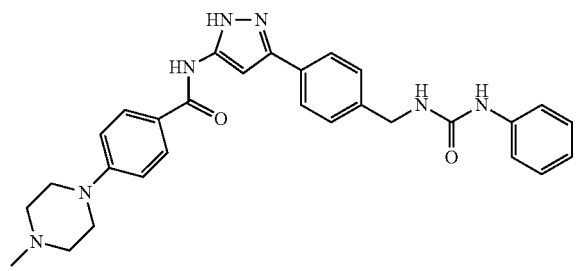
52
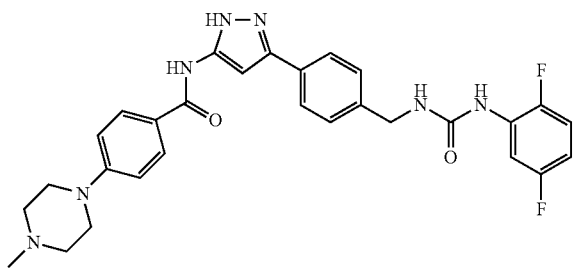
53
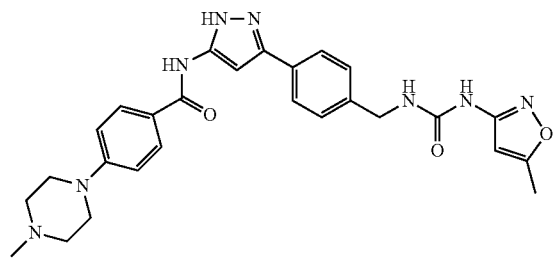
54
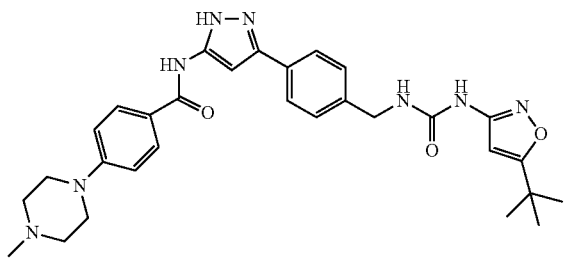
55
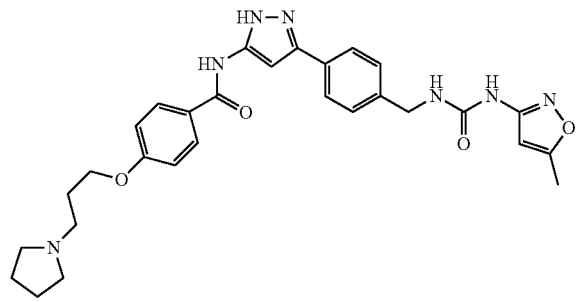
56
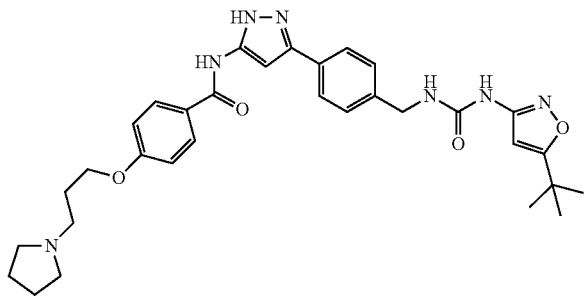

-continued
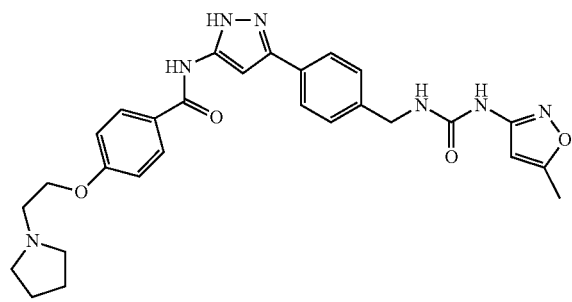
57
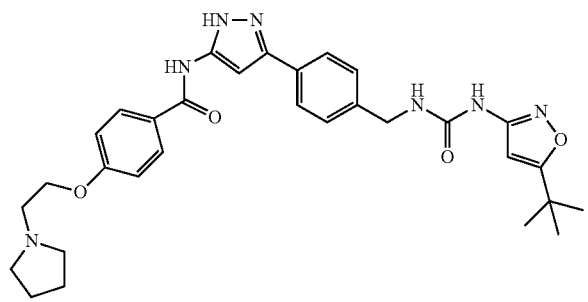
58
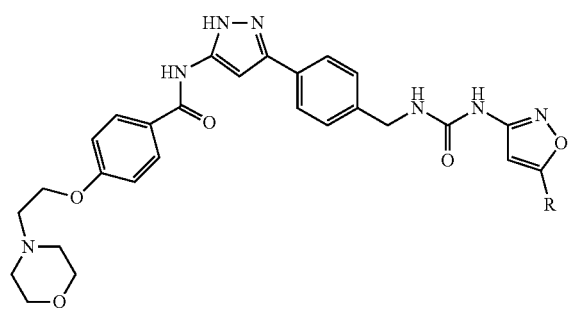
59a R = CH₃
59b R = C₂H₅
59c R = isopropyl
59d R = cyclopropyl
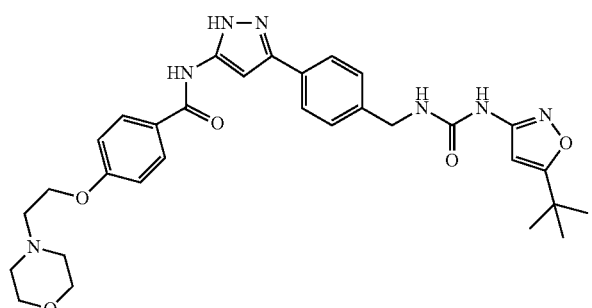
60
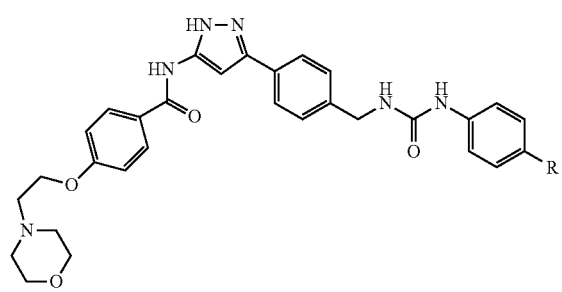
61a R = H
61b R = F
61C R = Cl
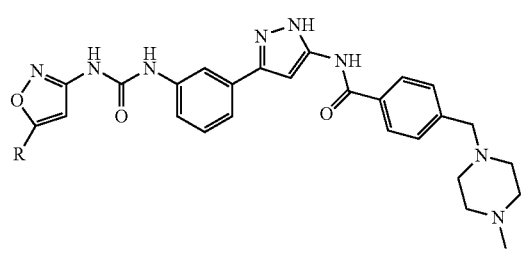
62a R = CH₃
62b R = C₂H₅
62c R = isopropyl
62d R = cyclopropyl
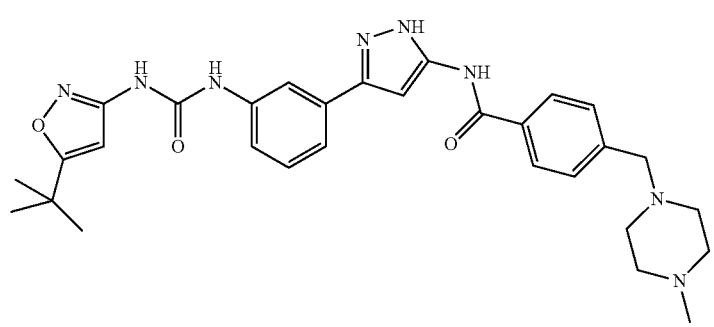
63

64
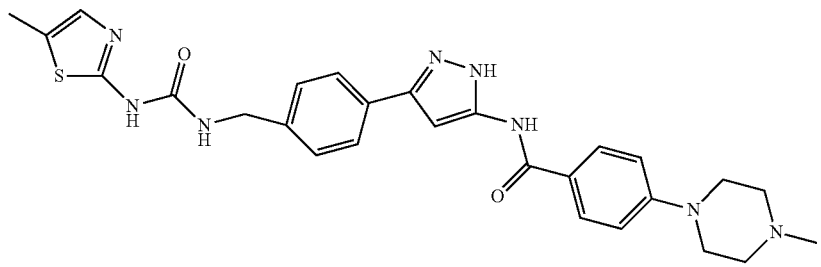
65
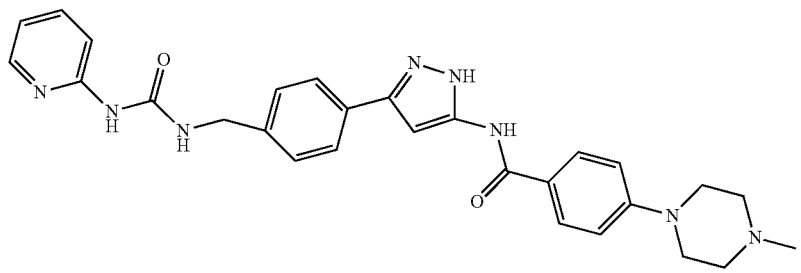
66
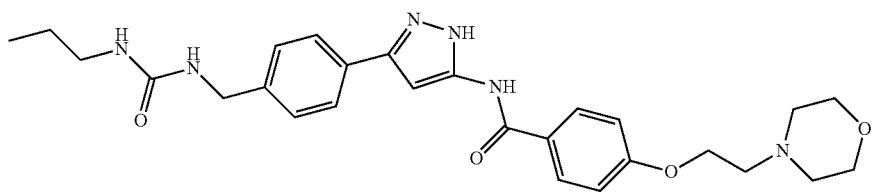
67 68
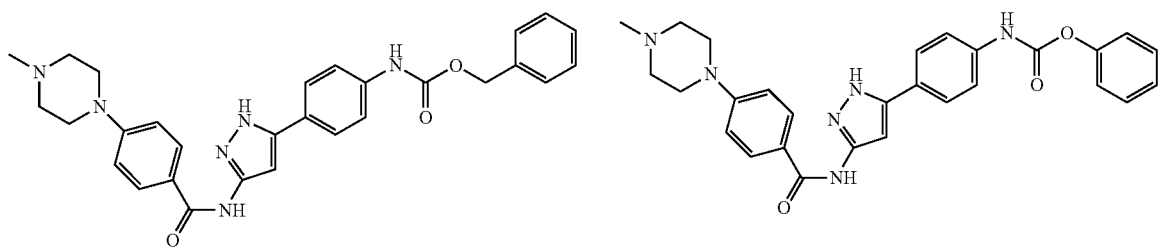
69 70
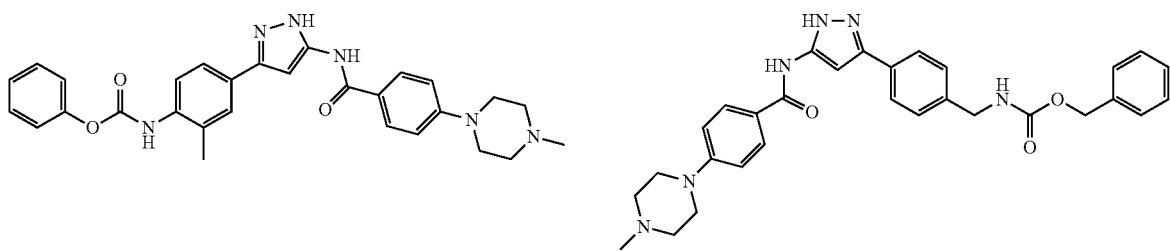

-continued
| | |
|---|---|
| 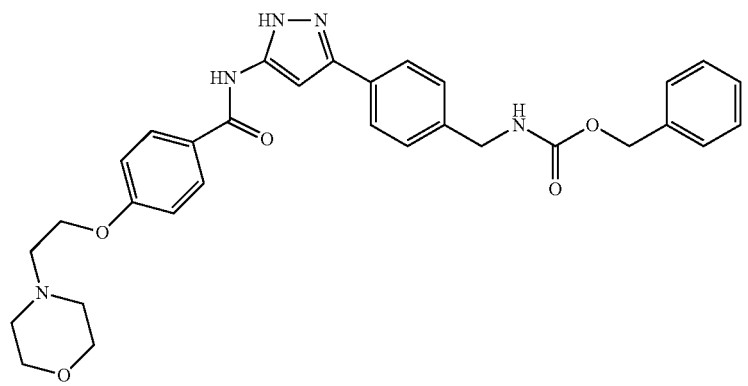 | 71 |
| 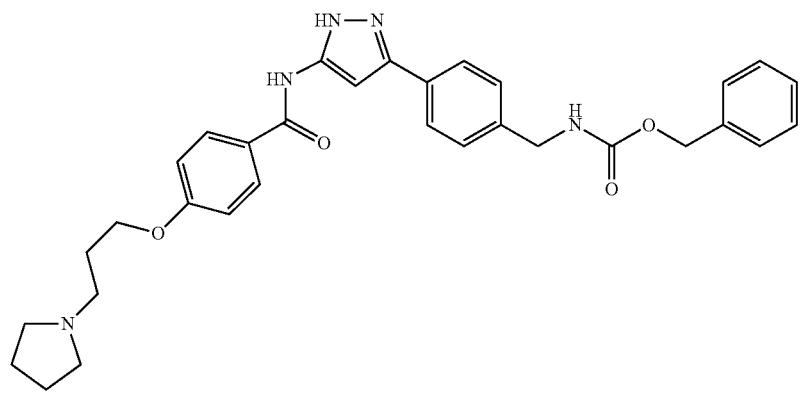 | 72 |
| 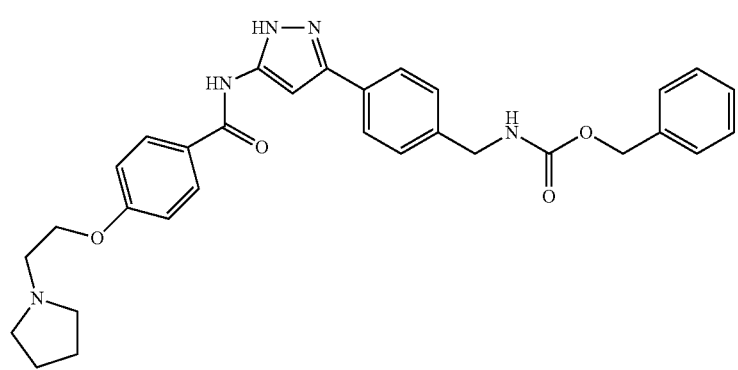 | 73 |
| 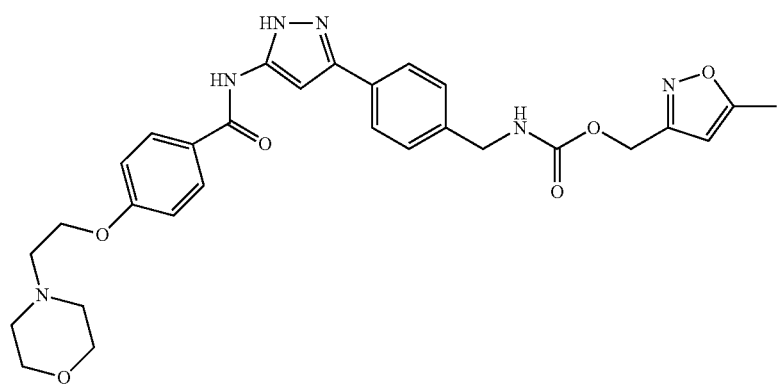 | 74 |

75
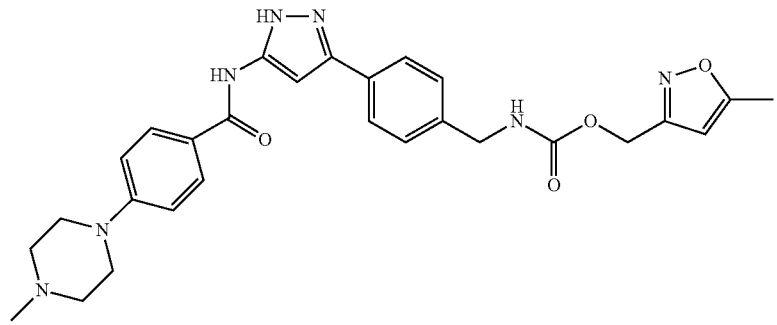
76
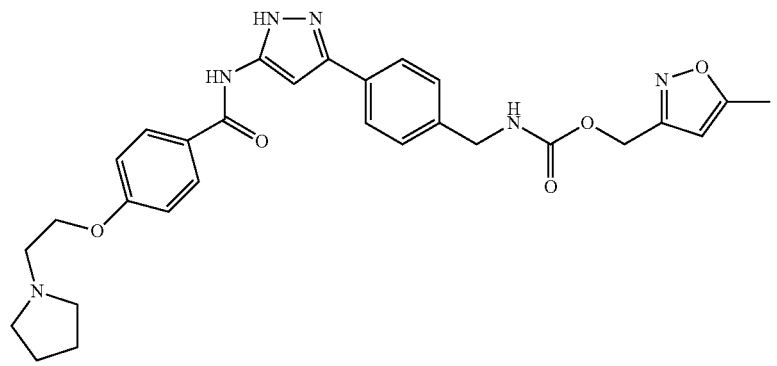
77
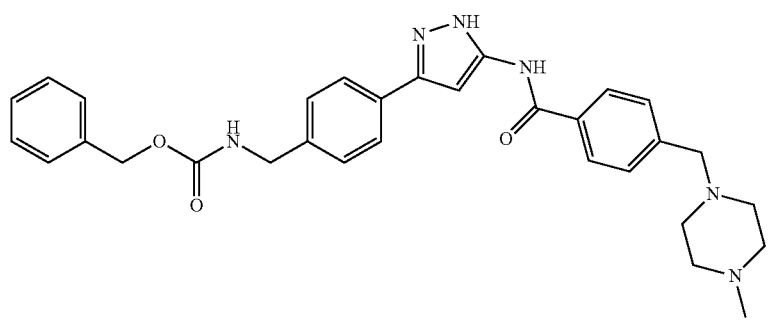
78
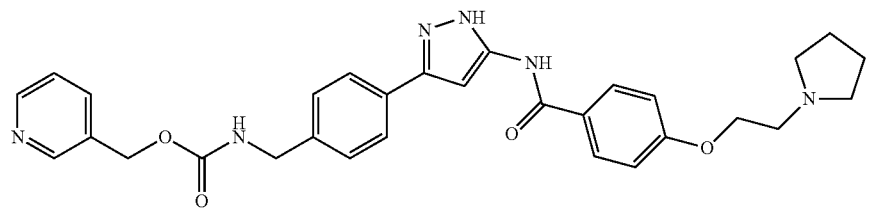
79
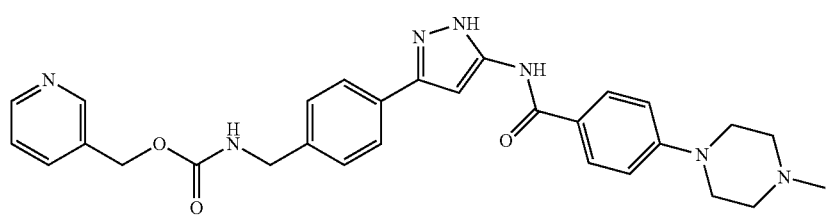

-continued
80
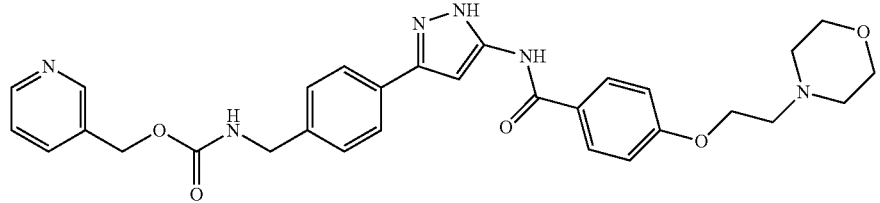
81
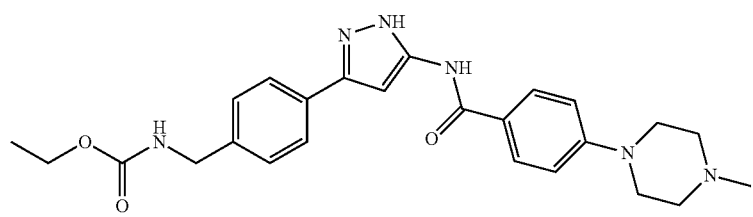
82
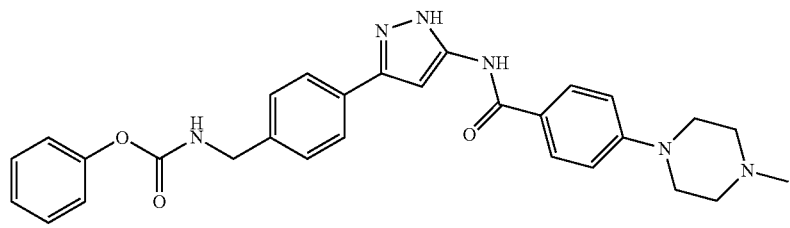
83
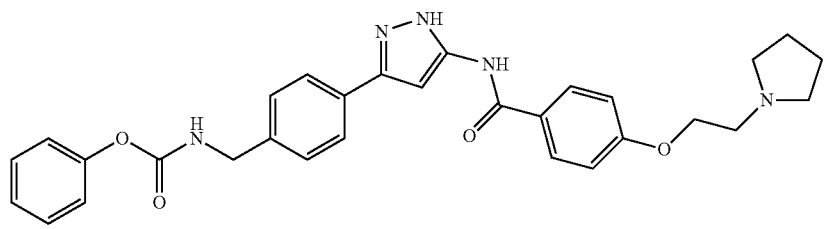
84
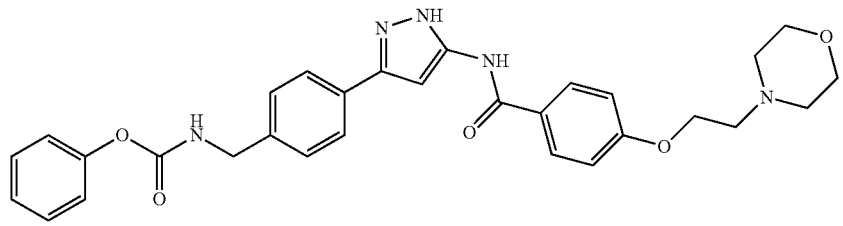
85
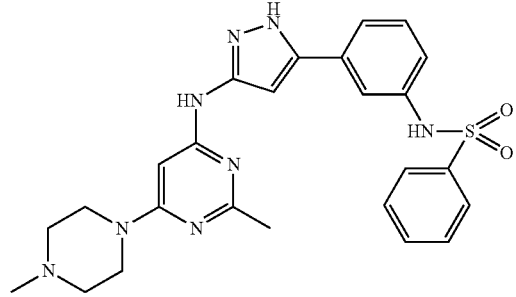
86
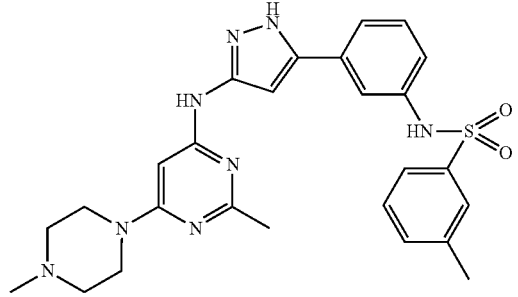

-continued
87
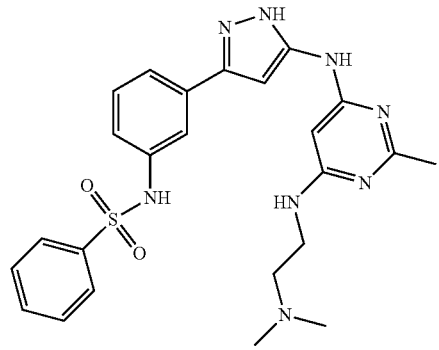
88
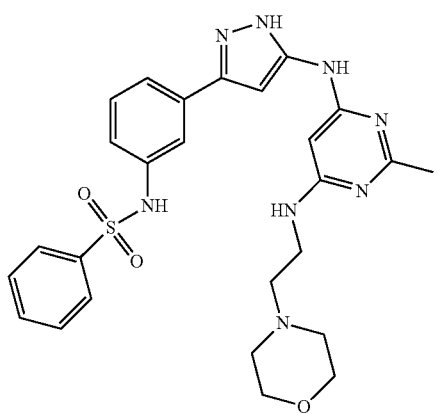
89
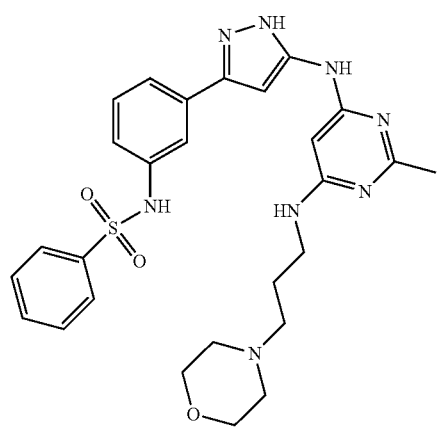
90
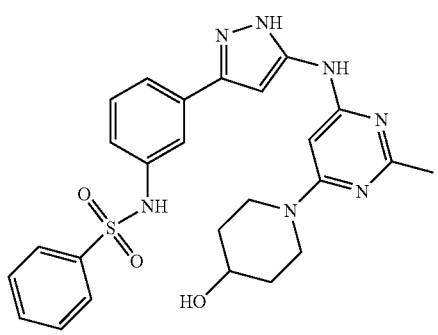
91
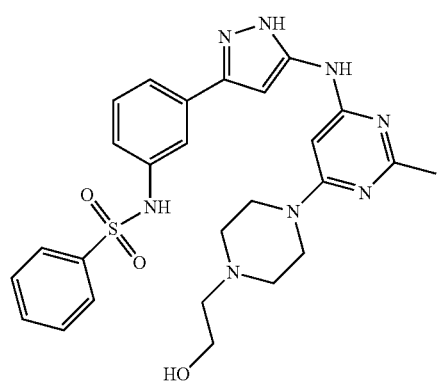
92
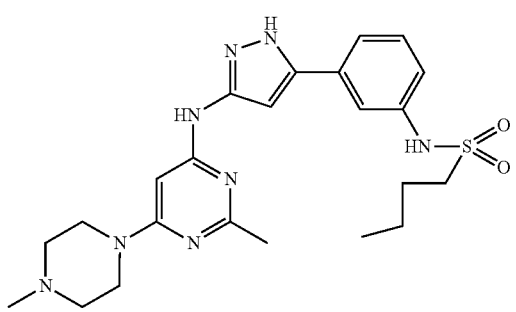

-continued
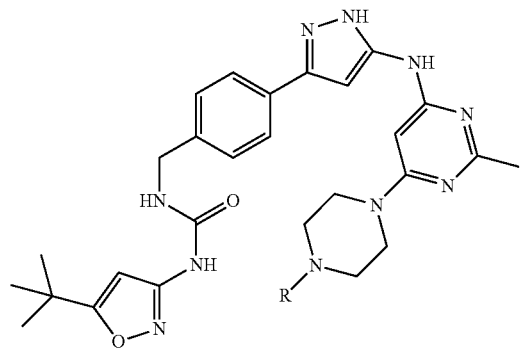
93a R = CH₂CH₂OH
93b R = CH₃
93c R = H
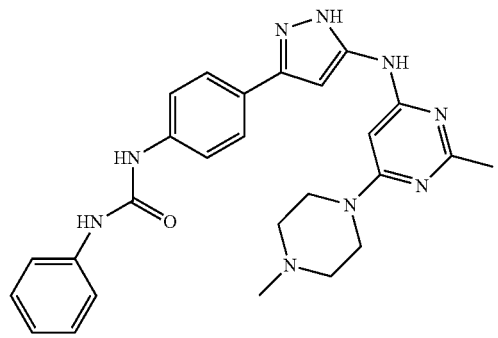
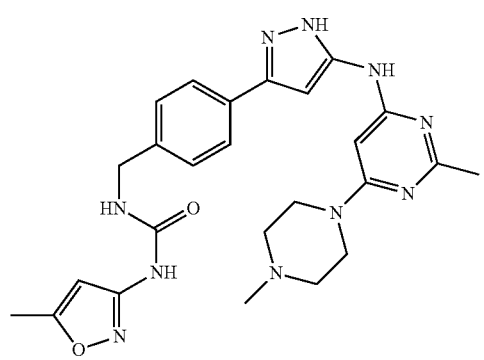
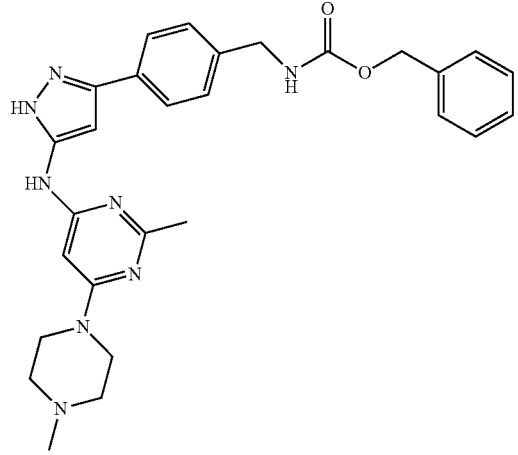
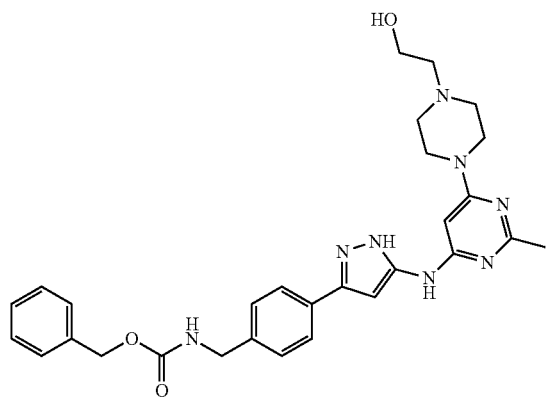
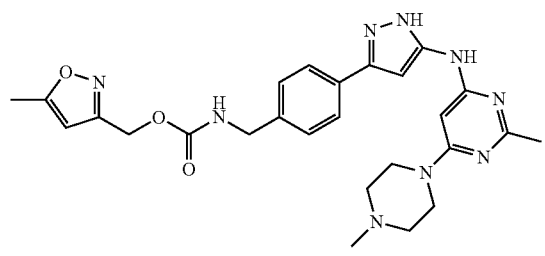
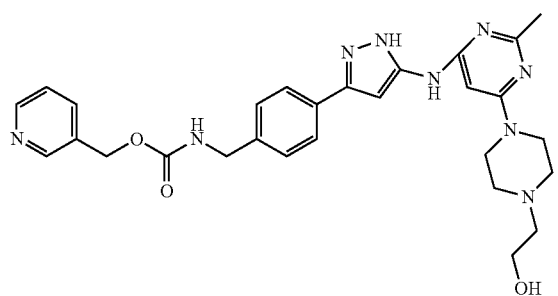

-continued
| | |
|---|---|
| 101 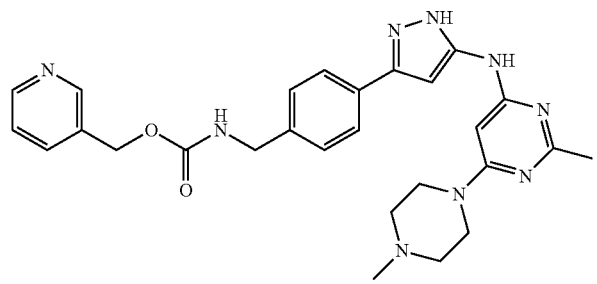 | 102 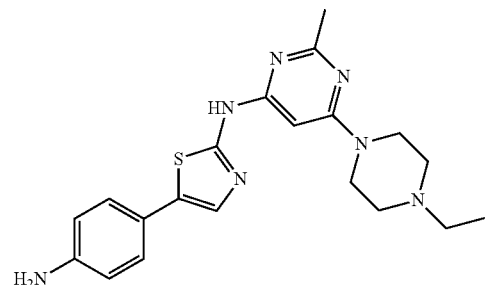 |
| 103 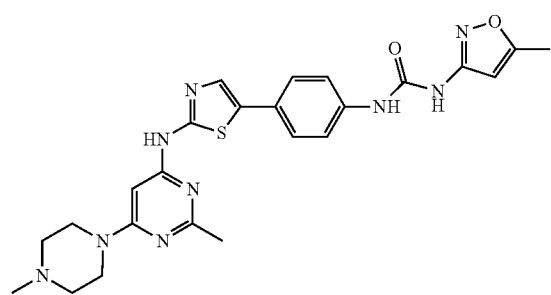 | 104 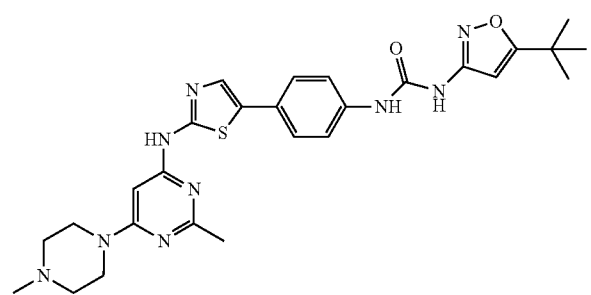 |
| 105 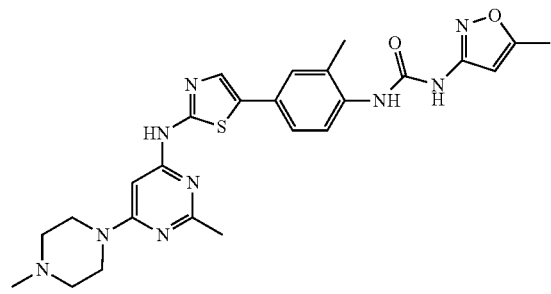 | 106 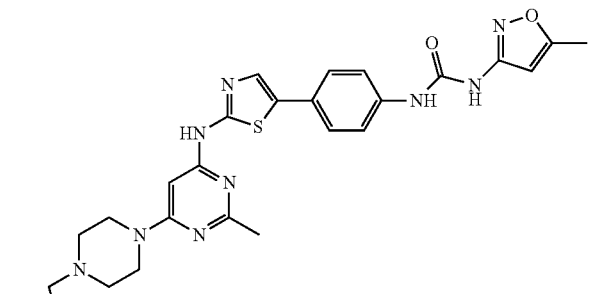 |
| 107 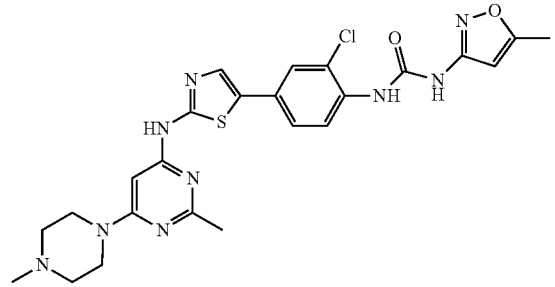 | 108 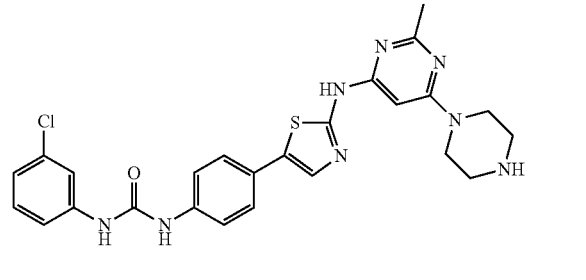 |
| 109 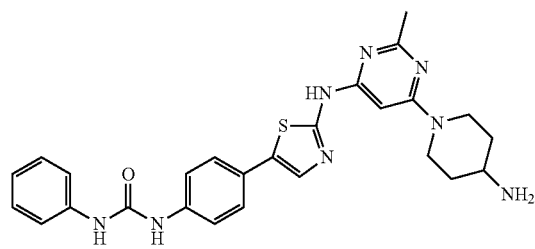 | 110 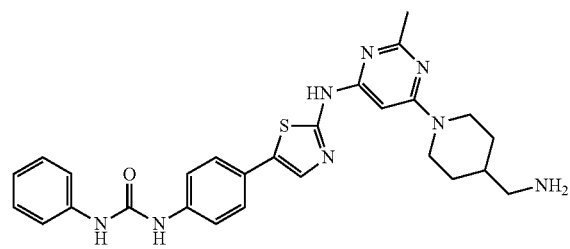 |

-continued
111 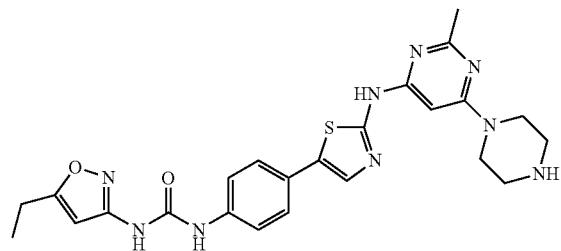
112 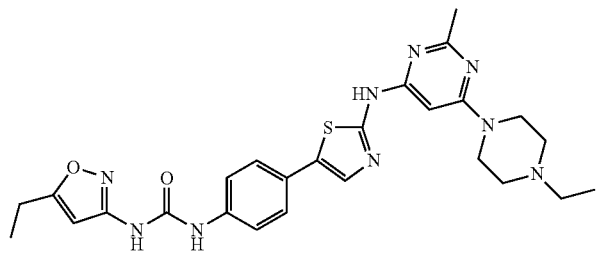
113 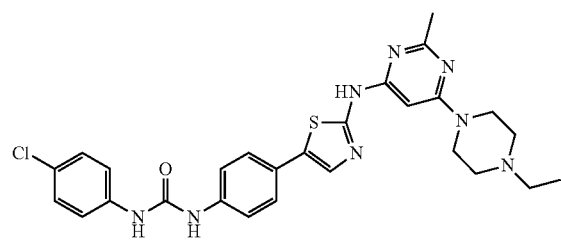
114 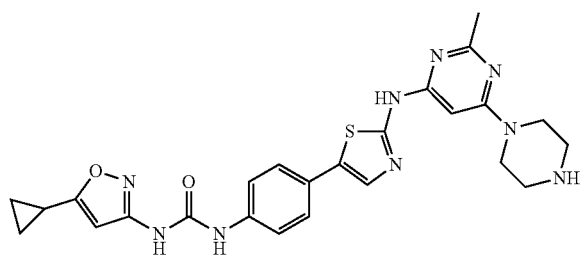
115 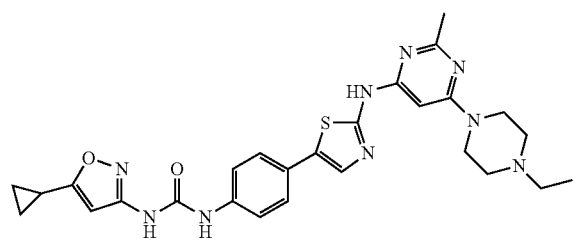
116 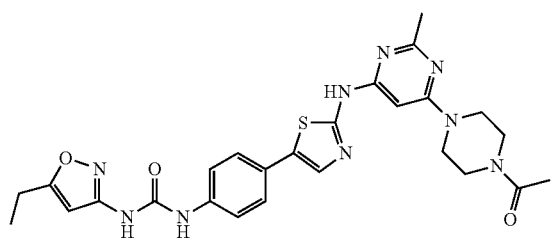
117 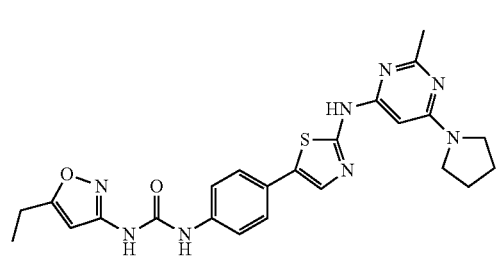
118
119 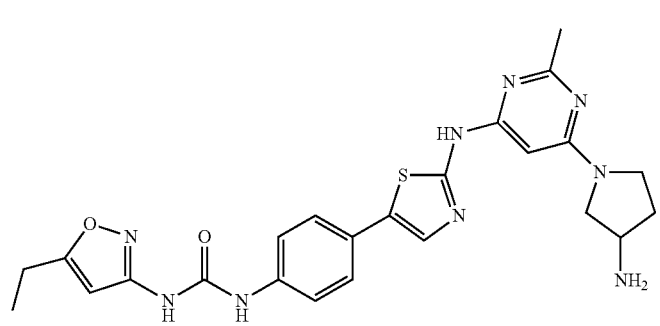

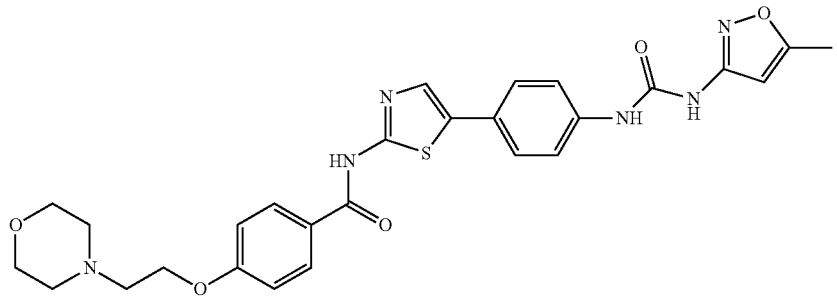
120
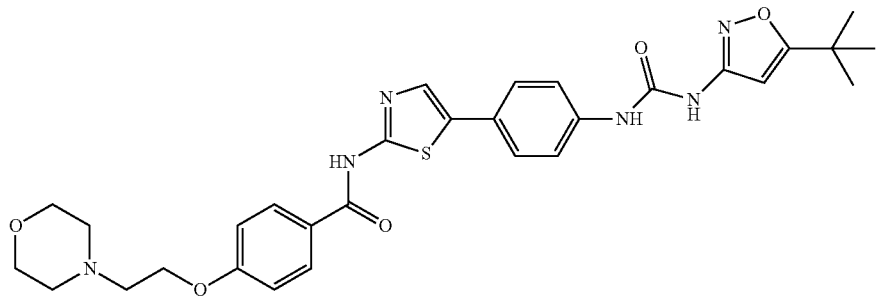
121
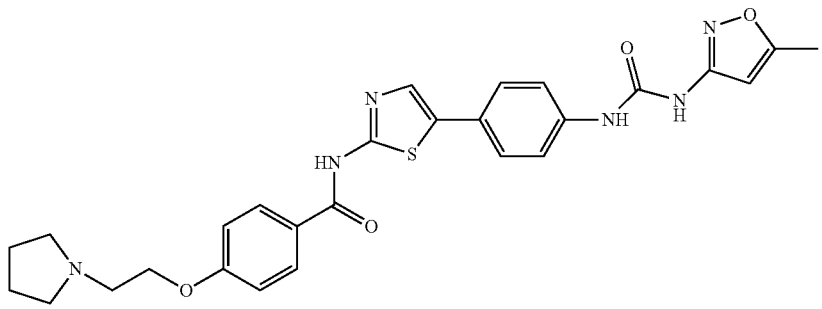
122
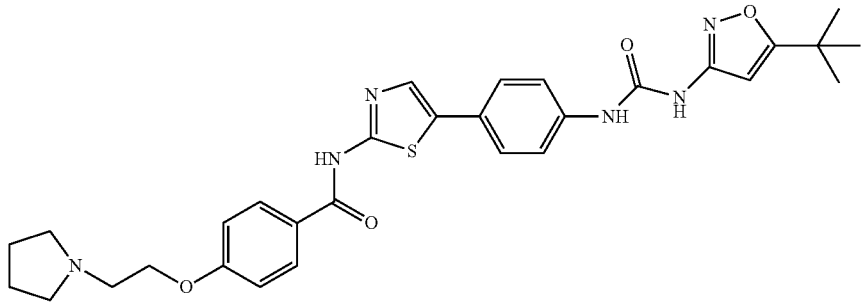
123
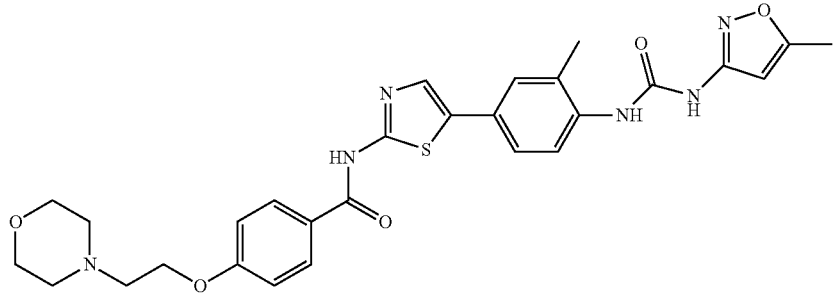
124

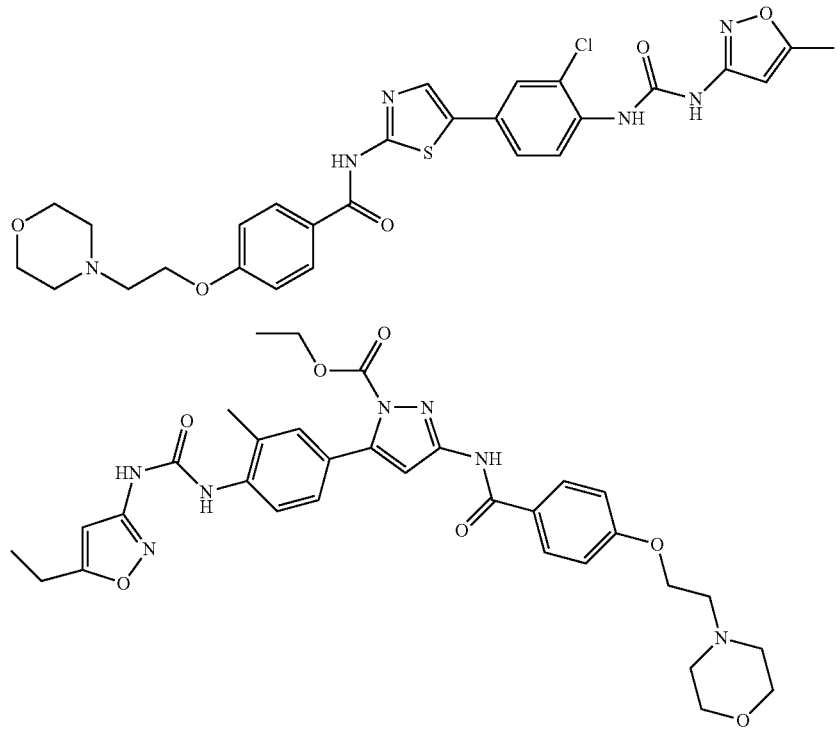

The pyrazole compounds and the thiazole compounds described herein can be prepared by methods well known in the art.

The route shown in Scheme 1 below exemplifies synthesis of the pyrazole compounds of the present invention:

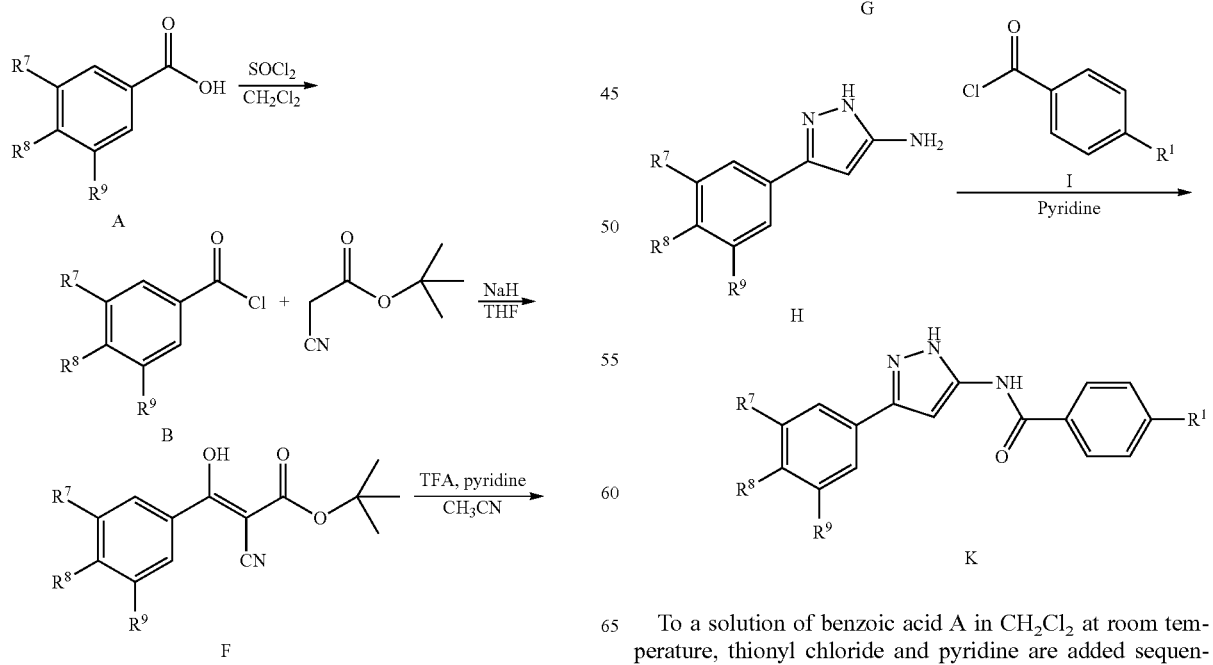

To a solution of benzoic acid A in CH$_2$Cl$_2$ at room temperature, thionyl chloride and pyridine are added sequentially. After refluxing for 8 h, the reaction mixture is cooled to room temperature and then concentrated in vacuo to yield acyl chloride B which is used without further purification. Acyl chloride B reacts with tert-butyl cyanoacetate in the presence of NaH to yield compound F. To a solution of compound F in CH₃CN at room temperature is added sequentially pyridine and TFA. After stirring at room temperature for 8 h, the solvent is evaporated to give a viscous residue, which is purified to yield cyanomethyl ketone G. Reaction of G with hydrazine hydrate by heating at 80° C. for 4 h affords pyrazolylamine H. Compound K can be synthesized via reacting pyrazolylamine H with appropriate acyl chloride I.

The pyrazole compounds of this invention can also be prepared by an alternative method, which is exemplified in Scheme 2 below:

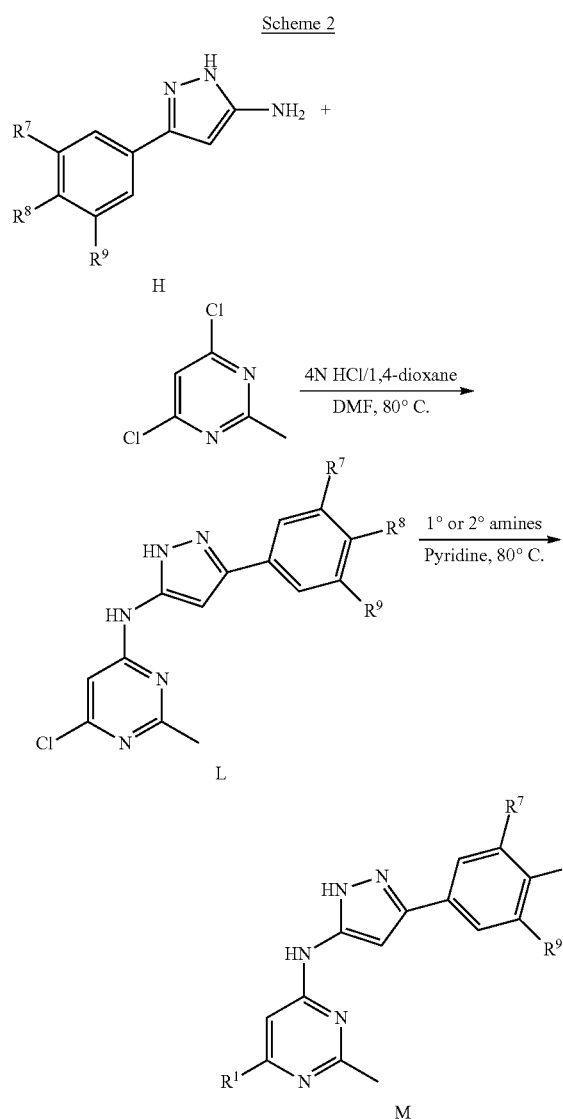

Pyrazolylamine H reacts with 4,6-dichloro-2-methylpyrimidine in the presence of hydrogen chloride solution (4.0 M in dioxane) to yield compound L. Compound L can further react with appropriate 1° or 2° amines at 80° C. for 2 h to afford pyrimidine pyrazole compound M, which is used without further purification.

The route shown in Scheme 3 below exemplifies synthesis of the thiazole compounds of the present invention:

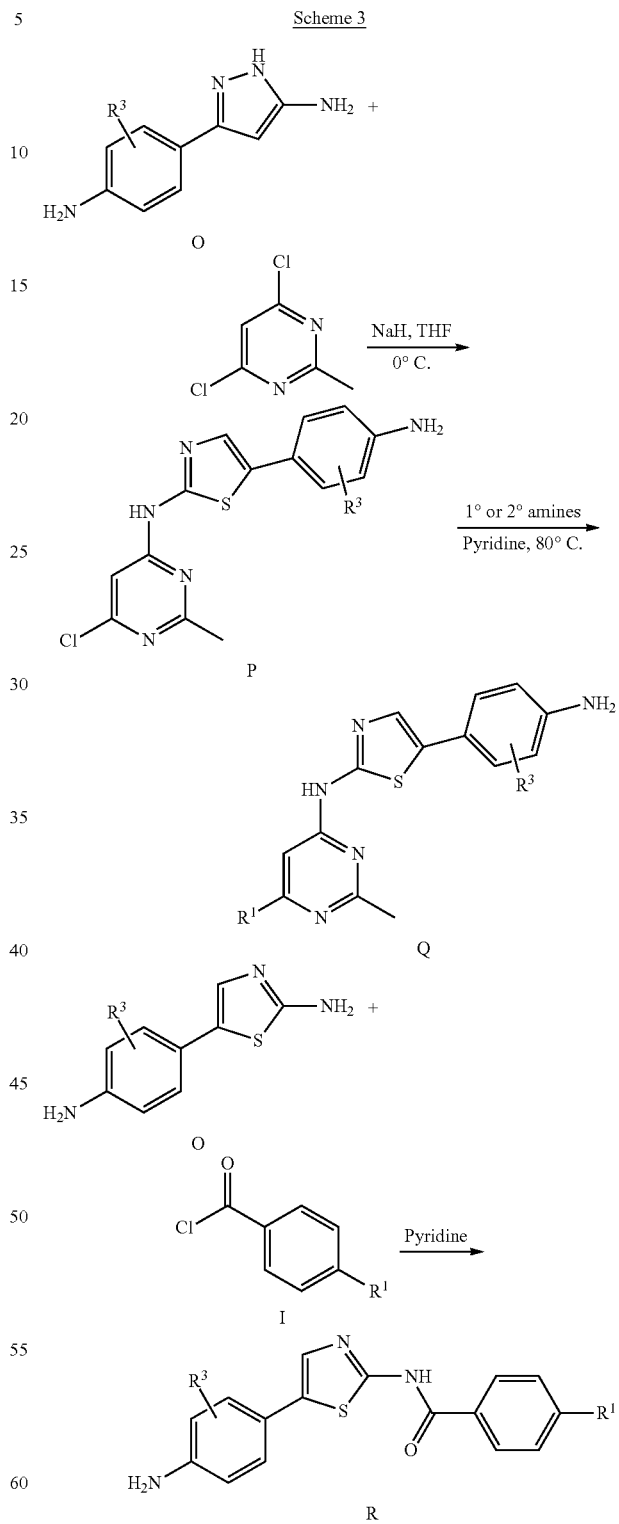

Thiazole amine O is synthesized following the procedure described in Lee et al., *Tetrahedron Letter,* 2000, 41, 3883-86. It reacts with 4,6-dichloro-2-methylpyrimidine, in the presence of NaH in THF, to yield compound P. Compound P can further react with appropriate 1° or 2° amines at 80° C. for 2 h to afford pyrimidine thiazole compound Q, which is used without further purification.

When the thiazole amine O reacts with acyl chloride I in the presence of pyridine, it affords the thiazole amide compound R.

The pyrazole compounds and thiazole compounds thus obtained can be further purified by column chromatography, high performance liquid chromatograph, crystallization, or any other suitable methods.

Other pyrazole compounds and thiazole compounds can be prepared using other suitable starting materials through the above synthetic routes and others known in the art. The methods described above may also additionally include steps, either before or after the steps described specifically herein, to add or remove suitable protecting groups in order to ultimately allow synthesis of the thiophene compounds. In addition, various synthetic steps may be performed in an alternate sequence or order to give the desired compounds. Synthetic chemistry transformations and protecting group methodologies (protection and deprotection) useful in synthesizing applicable pyrazole compounds and thiazole compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The pyrazole compounds and thiazole compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are a pharmaceutical composition that contains an effective amount of a compound of formula (I) of this invention and a pharmaceutically acceptable carrier, and a method for treating cancer associated with FLT3, aurora kinase, or VEGFR by administering to a subject in need of this treatment an effective amount of such a compound of formula (I).

As used herein, the term "treating" or "treatment" refers to administering one or more the above-described compounds to a subject, who has a cancer which is associated with FLT3, aurora kinase, or VEGFR, a symptom of or a predisposition toward it, with the purpose to confer a therapeutic effect, e.g., to cure, relieve, alter, affect, or ameliorate the cancer, the symptom of or the predisposition toward it. Such a subject can be identified by a health care professional based on results from any suitable diagnostic method.

The term "an effective amount" refers to the amount of an active pyrazole or thiazole compound that is required to confer a therapeutic effect on the treated subject. Effective amounts may vary, as recognized by those skilled in the art, depending on the types of diseases treated, route of administration, excipient usage, and the possibility of co-usage with other agents.

In this disclosure, "cancer associated with FLT3, aurora kinase, or VEGFR" refers to a cancer caused by or correlated with (e.g., partially) FLT3, aurora kinase, or VEGFR activity. The activity includes downstream and upstream events in biological pathways involving FLT3, aurora kinase, or VEGFR. Cancer that can be treated by the method of this invention includes both solid and haematological tumours of various organs. Examples of solid tumors include pancreatic cancer, bladder cancer (e.g., urothelium cancer), colorectal cancer, breast cancer (e.g., metastatic breast cancer), male genital tract cancer (e.g., seminal vesicle cancer, testes cancer, germ cell tumors, and prostate cancer such as androgen-dependent and androgen-independent prostate cancer), renal cancer (e.g., metastatic renal cell carcinoma), hepatocellular cancer, lung cancer (e.g., small cell lung cancer, non-small cell lung cancer, bronchioloalveolar carcinoma, and adenocarcinoma of the lung), ovarian cancer (e.g., progressive epithelial or primary peritoneal cancer), cervical cancer, uterus cancer, gestational trophoblastic disease (e.g., choriocarcinoma), gastric cancer, bile duct cancer, gallbladder cancer, small intestine cancer, esophageal cancer, oropharyngeal cancer, hypopharyngeal cancer, eye cancer (e.g., retinoblastoma), nerve cancer (e.g., Schwannoma, meningioma, neuroblastoma, and neuroma), head and neck cancer (e.g., squamous cell carcinoma of the head and neck), melanoma, plasmacytoma, endocrine gland neoplasm (e.g., pituitary adenoma, thyroid cancer, and adrenal tumor), neuroendocrine cancer (e.g., metastatic neuroendocrine tumors), brain tumors (e.g., glioma, anaplastic oligodendroglioma, glioblastoma multiforme, and astrocytoma such as adult anaplastic astrocytoma), bone cancer, and sarcomas from soft tissue or bone (e.g., Kaposi's sarcoma). Examples of hematologic malignancy include acute myeloid leukemia, chloroma, chronic myelogenous leukemia or CML (e.g., accelerated CML and CML blast phase), acute lymphoblastic leukemia, chronic lymphocytic leukemia, Hodgkin's disease, non-Hodgkin's lymphoma (e.g., follicular lymphoma, cutaneous T-cell lymphoma such as mycosis fungoides, and mantle cell lymphoma), B-cell lymphoma, multiple myeloma, Waldenstrom's macroglobulinemia, myelodysplastic syndromes (e.g., refractory anemia, refractory anemia with ringed sideroblasts, refractory anemia with excess blasts or RAEB, and RAEB in transformation or RAEB-T, and myeloproliferative syndromes).

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bio-availability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A pyrazole compound-containing composition or a thiazole compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the compounds of the present invention can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the pyrrazole compounds and the thiazole compounds of this invention in inhibiting FLT3, aurora kinase, or VEGFR. The compounds can further be examined for their efficacy in treating a cancer associated with FLT3, aurora kinase, or VEGFR in vitro or in vivo. For example, a compound can be tested for its efficacy in inhibiting cancel cell growth. Alternatively, it can be administered to an animal (e.g., a mouse model) having the cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Examples 1

Synthesis of Compounds 1-8

Compounds 1-8 were each prepared following the synthetic route shown in the scheme below:

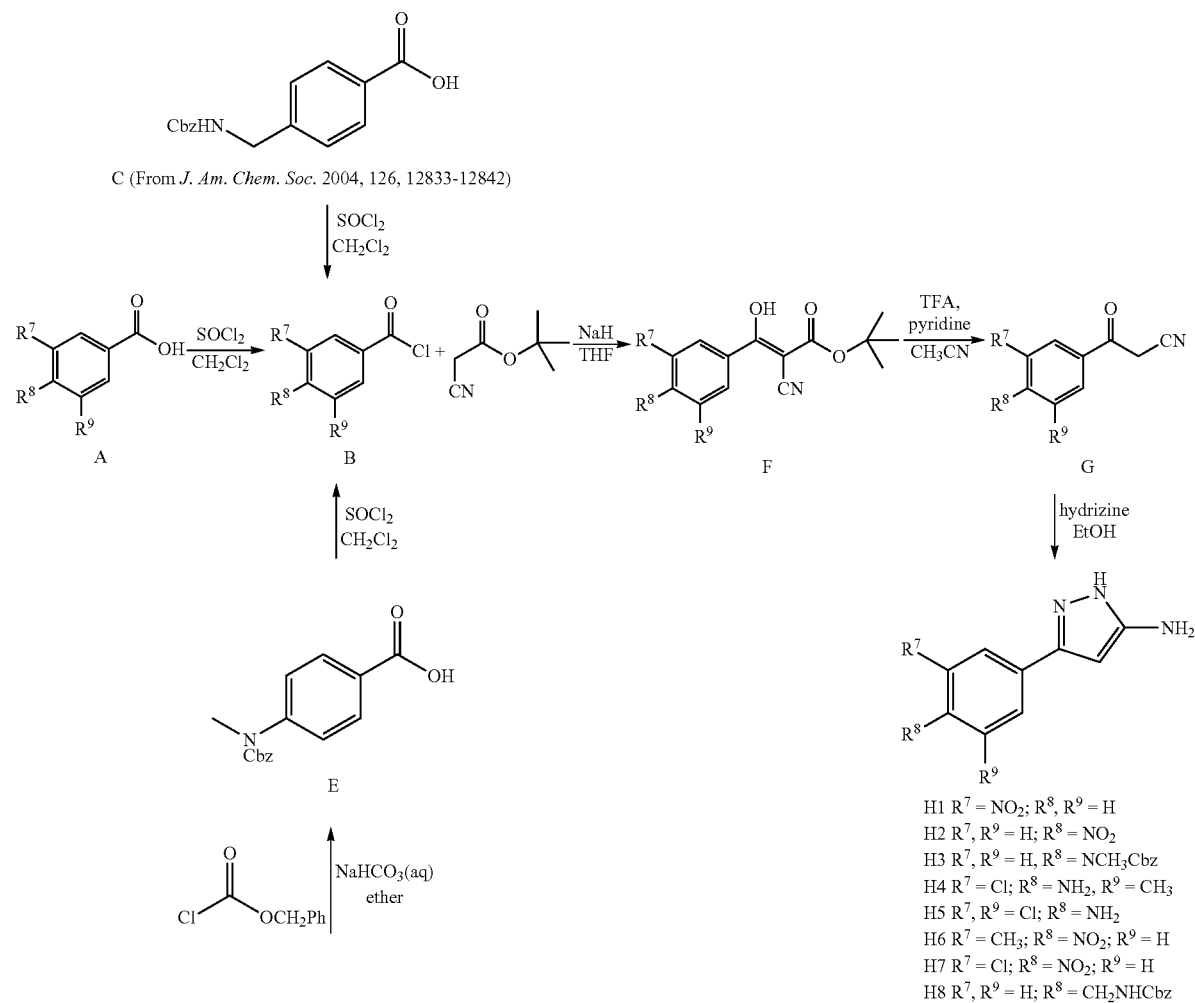

-continued

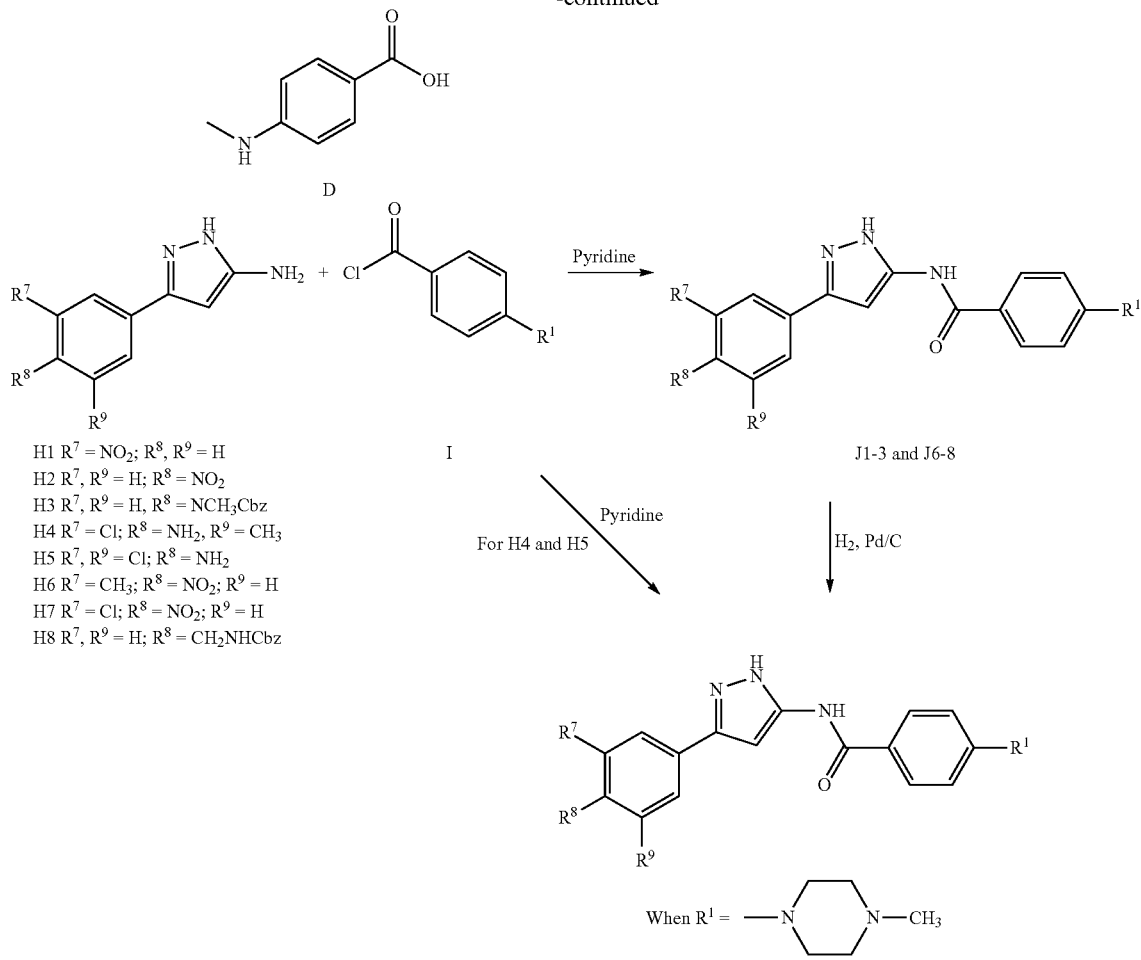

H1 R⁷ = NO₂; R⁸, R⁹ = H
H2 R⁷, R⁹ = H; R⁸ = NO₂
H3 R⁷, R⁹ = H; R⁸ = NCH₃Cbz
H4 R⁷ = Cl; R⁸ = NH₂, R⁹ = CH₃
H5 R⁷, R⁹ = Cl; R⁸ = NH₂
H6 R⁷ = CH₃; R⁸ = NO₂; R⁹ = H
H7 R⁷ = Cl; R⁸ = NO₂; R⁹ = H
H8 R⁷, R⁹ = H; R⁸ = CH₂NHCbz

K1 = 1, K2 = 2, K3 = 3, K4 = 4
K5 = 5, K6 = 6, K7 = 7, K8 = 8
K1 R⁷ = NH₂; R⁸, R⁹ = H
K2 R⁷, R⁹ = H; R⁸ = NH₂
K3 R⁷, R⁹ = H; R⁸ = NHC₃Cbz
K4 R⁷ = Cl; R⁸ = NH₂, R⁹ = CH₃
K5 R⁷, R⁹ = Cl; R⁸ = NH₂
K6 R⁷ = CH₃; R⁸ = NH₂; R⁹ = H
K7 R⁷ = Cl; R⁸ = NH₂; R⁹ = H
K8 R⁷, R⁹ = H; R⁸ = CH₂NH₂

N-(Benzyloxycarbonyl)-4-(methylamino) benzoic acid E: A solution of 4-(methylamino) benzoic acid D (1.01 g, 10 mmol) and sodium bicarbonate (2.10 g, 25 mmol) in 50 mL of diethyl ether/water (1/1) was cooled in an ice-water bath. To this solution was added benzyl chloroformate (2.05 g, 12 mmol) and the mixture stirred vigorously at room temperature for 8 h. The mixture was cooled to 0° C., diluted with ethyl acetate (50 mL), and stirred vigorously while acidifying to pH=3 with 1 N HCl. The organic layer was dried over MgSO₄ and concentrated in vacuo. Purification by flash column chromatography (eluted with CH₂Cl₂/EA=6/4) yielded E as a white solid (65%).

Acyl chloride B: To a solution of benzoic acid A, C or E (1.0 equiv) in CH₂Cl₂ at room temperature was added sequentially thionyl chloride (2.0 equiv) and pyridine (0.2 equiv). After refluxing for 8 h, the reaction was cooled to room temperature. Concentration in vacuo gave the desired compounds B which were used without further purification (>95%).

Pyrazolylamine H:
Step I. Synthesis of α-tert-butylcarboxy-β-hydroxy-cinnamonitrile F:

A suspension of NaH (60% in oil, 1.5 equiv) in THF was cooled in an ice-water bath. To this solution was slowly added tert-butyl cyanoacetate (1.0 equiv) and the reaction stirred at room temperature for 0.5 h. To this white suspension was added acyl chloride B (1.0 equiv) and the reaction stirred at room temperature for 4 h. The reaction was again cooled in an ice-water bath and carefully quenched with 1 N HCl to pH=3. The reaction was diluted with CH₂Cl₂. The organic layer was separated, dried over MgSO₄ and concentrated in vacuo. Purification by flash column chromatography (eluted with CH₂Cl₂/EA) yielded compounds F. Only one of F is selected to show its NMR spectrum and Mass.

tert-Butyl-(Z)-2-cyano-3-hydroxy-3-(4-nitrophenyl)-2-propenoate (F2). ¹H NMR (400 MHz, CDCl₃): δ 8.34 (d, J=9.2 Hz, 2H), 8.14 (d, J=9.2 Hz, 2H), 1.61 (s, 9H); MS (APCI⁻) m/z Calcd for $C_{14}H_{14}F_3N_2O_5$: 290.09; found: 289.1 (M–H⁺).

Step II. Synthesis of Cyanomethyl Ketone G:

To a solution of compounds F (1.0 equiv) in CH₃CN at room temperature was added sequentially pyridine (0.2 equiv) and TFA. After stirring at room temperature for 8 h, the solvent was evaporated to give a viscous residue, which was partitioned between CH₂Cl₂ and water. The organic layer was separated, dried over MgSO₄ and concentrated in vacuo. Purification by flash column chromatography (eluted with CH₂Cl₂/EA) yielded compounds G. Only one of compounds G is selected to show its NMR spectrum and Mass.

2-(4-Nitrophenyl)-2-oxoethyl cyanide (G2). ¹H NMR (400 MHz, CDCl₃): δ 8.38 (d, J=8.8 Hz, 2H), 8.11 (d, J=8.8 Hz, 2H), 4.16 (s, 2H); MS (APCI⁻) m/z Calcd for $C_9H_6N_2O_3$: 190.04; found: 189.1 (M–H⁻).

Step III. Synthesis of Pyrazolylamine H:

To a solution of cyanomethyl ketone G (1.0 equiv) in EtOH at room temperature was added hydrazine hydrate (1.1 equiv) and the resultant mixture was stirred at 80° C. for 4 h. The mixture was cooled to 0° C. and the precipitate was collected by filtration to yield pure compounds H1-3 and H6-8. Compounds H4 and H5 were synthesized under the same reaction conditions and purified by flash column chromatography (eluted with CH₂Cl₂/CH₃OH) to yield the impure compounds H4 and H5 which were used in the next step without further purification.

3-(3-Nitrophenyl)-1H-5-pyrazolamine(H1). ¹H NMR (400 MHz, DMSO-d6): δ 12.25 (s, 0.3H), 11.77 (s, 0.7H), 8.47 (s, 1H), 8.09 (d, J=7.2 Hz, 2H), 7.65 (d, J=6.4 Hz, 1H), 6.02 (s, 0.3H), 5.80 (s, 0.7H), 5.18 (s, 1.4H)), 4.71 (s, 0.6H); MS (ES⁺) m/z Calcd for $C_9H_8N_4O_2$: 204.06; found: 205.1 (M+H⁺).

3-(4-Nitrophenyl)-1H-5-pyrazolamine(H2). ¹H NMR (400 MHz, DMSO-d6): δ 12.31 (s, 0.3H), 11.89 (s, 0.7H), 8.21 (d, J=7.6 Hz, 2H), 7.92 (d, J=7.6 Hz, 2H), 6.05 (s, 0.3H), 5.28 (s, 0.7H), 5.20 (s, 1.4H), 4.76 (s, 0.6H); MS (ES⁺) m/z Calcd for $C_9H_8N_4O_2$: 204.06; found: 205.3 (M+H⁺).

3-(3-Methyl-4-nitrophenyl)-1H-5-pyrazolamine (H6). ¹H NMR (400 MHz, DMSO-d6): δ 11.85 (s, 1H), 8.01 (d, J=8.8 Hz, 1H), 7.73 (s, 1H), 7.72 (d, J=8.4 Hz, 1H), 5.85 (bs, 1H), 5.12 (s, 2H)), 2.57 (s, 3H); MS (ES⁺) m/z Calcd for $C_{10}H_{10}N_4O_2$: 218.08; found: 219.3 (M+H⁺).

3-(3-chloro-4-nitrophenyl)-1H-5-pyrazolamine (H7). ¹H NMR (400 MHz, DMSO-d6): δ 11.96 (s, 1H), 8.08 (d, J=8.8 Hz, 1H), 7.99 (d, J=1.2 Hz, 1H), 7.84 (dd, J=1.2 Hz, 8.4 Hz, 1H), 5.91 (s, 1H), 5.16 (s, 2H). MS (ES⁺) m/z Calcd for $C_9H_7ClN_4O_2$: 238.63; found: 239.0 (M+H⁺).

Benzyl N-[4-(5-amino-1H-3-pyrazolyl)benzyl]carbamate (H8). ¹H NMR (400 MHz, DMSO-d6): δ 11.76 (s, 1H), 7.84 (t, J=5.8 Hz, 1H), 7.58 (d, J=8.0 Hz, 2H), 7.39-7.28 (m, 6H), 7.24 (d, J=8.0 Hz, 2H), 5.73 (s, 1H), 5.05 (s, 2H), 4.82 (bs, 1H)), 4.19 (d, J=6.4 Hz, 2H); MS (ES⁺) m/z Calcd for $C_{18}H_{18}N_4O_2$: 322.14; found: 323.2 (M+H⁺).

Compounds K:
Step I. Synthesis of Compounds J:

To a solution of pyrazolylamine H (1.0 equiv) in pyridine at room temperature was added acyl chloride I (1.2 equiv). After stirring at room temperature for 1 h, the reaction mixture was evaporated to dryness and the residue suspended in 1 N NaHCO₃. The suspension was vigorously stirred at room temperature for 1 h before the resultant solid was collected by filtration and dried in vacuo. Purification by flash column chromatography (eluted with CH₂Cl₂/CH₃OH) yielded compounds J. Only one of J is selected to show its NMR spectrum and Mass.

N1-[3-(4-nitrophenyl)-1H-5-pyrazolyl]-4-[(4-methylpiperazino)methyl]benzamide. ¹H NMR (300 MHz, DMSO-d6): δ 10.98 (s, 1H), 8.31 (d, J=8.4 Hz, 2H), 8.07-7.97 (m, 6H), 7.43 (d, J=7.8 Hz, 2H), 3.52 (s, 2H), 3.34 (s, 4H), 2.36 (s, 4H), 2.15 (s, 3H). MS (ES⁺) m/z Calcd for $C_{22}H_{24}N_6O_3$: 420.19; found: 421.2 (M+H⁺).

Step II. Synthesis of Compounds K1-8:

To a solution of compounds J (1.0 equiv) in EtOH was added 12 N HCl (2.0 equiv) and a catalytic amount of 10% Pd/C under argon at room temperature. The mixture was vigorously stirred at room temperature under an atmospheric pressure of hydrogen for 12 h. The catalyst was removed by filtration and the filtrate was concentrated in vacuo to give the desired compounds K1-3 and K6-8. Compounds K4 and K5 were synthesized under the same reaction conditions as described in the synthesis of compound J, starting from H4-5. Compounds K1-8 were used for next step without further purification or purification by flash column chromatography (eluted with CH₂Cl₂/CH₃OH) yielded Compounds 1-8.

N1-[3-(3-aminophenyl)-1H-5-pyrazolyl]-4-(4-methylpiperazino)benzamide (Compound 1). ¹H NMR (400 MHz, DMSO-d6): δ 12.69 (s, 1H), 10.48 (s, 1H), 7.91 (d, J=8.8 Hz, 2H), 7.07 (t, 1H) 6.97 (d, J=8.8 Hz, 2H), 6.87 (d, J=8.0 Hz, 3H), 6.53 (d, J=7.6 Hz, 1H), 5.18 (s, 2H), 3.27 (t, J=4.8 Hz, 4H), 2.43 (t, J=5.0 Hz, 4H), 2.21 (s, 3H); MS (ES⁺) m/z calcd. for $C_{21}H_{24}N_6O$: 376.20; found: 377.2 (M+H⁺).

N1-[3-(4-aminophenyl)-1H-5-pyrazolyl]-4-(4-methylpiperazino)benzamide (Compound 2). ¹H NMR (400 MHz, DMSO-d6): δ 12.41 (s, 1H), 10.43 (s, 1H), 7.91 (d, J=8.4 Hz, 2H), 7.38 (d, J=7.6 Hz, 2H), 6.96 (d, J=8.8 Hz, 2H), 6.71 (s, 1H), 6.59 (d, J=8.0 Hz, 2H), 5.30 (s, 2H), 3.26 (t, J=4.2 Hz, 4H), 2.42 (t, J=4.4 Hz, 4H), 2.21 (s, 3H); MS (ES⁺) m/z calcd. for $C_{21}H_{24}N_6O$: 376.20; found: 377.2 (M+H⁺), 399.2 (M+Na⁺).

N1-3-[4-(methylamino)phenyl]-1H-5-pyrazolyl-4-(4-methylpiperazino)benzamide (Compound 3). ¹H NMR (400 MHz, DMSO-d6): δ 12.45 (s, 1H), 10.40 (s, 1H), 7.90 (d, J=8.8 Hz, 2H), 7.45 (d, J=8.4 Hz, 2H), 6.96 (d, J=8.4 Hz, 2H), 6.76 (s, 1H), 6.56 (d, J=8.8 Hz, 2H), 5.89 (s, 1H), 3.28-3.20 (m, 4H, overlapping with water peak), 2.68 (d, J=5.2 Hz, 3H), 2.44-2.38 (m, 4H), 2.20 (s, 3H); MS (ES⁺) m/z Calcd for $C_{22}H_{26}N_6O$: 390.22; found: 391.2 (M+H⁺).

N1-[3-(4-amino-3-chloro-5-methylphenyl)-1H-5-pyrazolyl]-4-(4-methylpiperazino) benzamide (Compound 4). ¹H NMR (400 MHz, DMSO-d6): δ 12.54 (s, 1H), 10.43 (s, 1H), 7.92 (d, J=8.8 Hz, 2H), 7.50 (s, 1H), 7.35 (s, 1H), 6.97 (d, J=8.4 Hz, 2H), 6.85 (s, 1H), 5.28 (s, 2H), 3.31-3.20 (m, 4H, overlapping with water peak), 2.40 (t, J=5.2 Hz, 4H), 2.22 (s, 3H), 2.19 (s, 3H); MS (ES⁺) m/z Calcd for $C_{22}H_{25}ClN_6O$: 424.18; found: 425.2 (M+H⁺).

N1-[3-(4-amino-3,5-dichlorophenyl)-1H-5-pyrazolyl]-4-(4-methylpiperazino)benzamide (Compound 5). ¹H NMR (300 MHz, DMSO-d6): δ 10.50 (s, 1H), 7.93 (d, J=8.1 Hz, 2H), 7.67 (s, 1H), 7.63 (s, 1H), 7.00 (d, J=8.1 Hz, 2H), 5.74 (s, 2H), 3.30 (t, J=4.5 Hz, 4H), 2.48 (t, J=4.5 Hz, 4H), 2.24 (s, 3H); MS (ES⁺) m/z Calcd for $C_{21}H_{22}Cl_2N_6O$: 444.12; found: 445.1 (M+H⁺).

N1-[3-(4-amino-3-methylphenyl)-1H-5-pyrazolyl]-4-(4-methylpiperazino)benzamide (Compound 6). ¹H NMR (300 MHz, DMSO-d6): δ 12.40 (s, 1H), 10.38 (s, 1H), 7.91 (d, J=8.7 Hz, 2H), 7.31 (s, 1H) 7.27 (d, J=8.4 Hz, 1H), 6.96 (d, J=8.7 Hz, 2H), 6.74 (s, 1H), 6.63 (d, J=8.4 Hz, 1H), 5.06 (s, 2H), 3.26 (br s, 4H), 2.42 (br s, 4H), 2.21 (s, 3H), 2.09 (s, 3H); MS (ES⁺) m/z calcd. for $C_{22}H_{26}N_6O$: 390.21; found: 413.0 (M+Na), 391.0 (M+H⁺).

N1-[3-(4-amino-3-chlorophenyl)-1H-5-pyrazolyl]-4-(4-methylpiperazino)benzamide (Compound 7). ¹H NMR (300

MHz, DMSO-d6): δ 12.55 (s, 1H), 10.45 (s, 1H), 7.91 (d, J=9.0 Hz, 2H), 7.60 (d, J=1.8 Hz, 1H), 7.40 (dd, J=8.7, 1.8 Hz, 1H), 6.81 (d, J=8.7 Hz, 2H), 6.83 (d, J=8.4 Hz, 2H), 5.57 (s, 2H), 3.31-3.29 (m, 4H), 2.51-2.49 (m, 4H), 2.26 (s, 3H); MS (ES+) m/z calcd. for $C_{21}H_{23}ClN_6O$: 410.16; found: 411.0 (M+H+).

N1-3-[4-(aminomethyl)phenyl]-1H-5-pyrazolyl-4-(4-methylpiperazino)benzamide (Compound 8). $^1$H NMR (400 MHz, DMSO-d6): δ 7.89 (d, J=8.8 Hz, 2H), 7.61 (d, J=8.4 Hz, 1H), 7.57 (d, J=8.0 Hz, 1H), 7.12 (d, J=8.0 Hz, 1H), 7.05 (d, J=8.4 Hz, 1H), 6.75 (d, J=8.8 Hz, 2H), 4.01 (s, 1H), 3.61 (s, 1H), 3.10 (br s, 4H), 2.54 (br s, 4H), 2.22 (s, 3H); MS (ES+) m/z calcd. for $C_{22}H_{26}N_6O$: 390.22; found: 391.2 (M+H+).

Example 2

Synthesis of Compounds 9-11

Below is a general synthetic scheme for the synthesis of Compounds 9-11:

N1-3-[4-(benzoylamino)phenyl]-1H-5-pyrazolyl-4-(4-methylpiperazino)benzamide (Compound 10). $^1$H NMR (400 MHz, DMSO-d6): δ 12.81 (bs, 1H), 10.59 (bs, 1H), 10.39 (s, 1H), 8.01-7.92 (m, 4H), 7.87 (d, J=8.8 Hz, 2H), 7.73 (d, J=8.4 Hz, 2H), 7.63-7.56 (m, 1H), 7.56-7.50 (m, 2H), 7.02 (d, J=8.8 Hz, 2H), 6.93 (bs, 1H), 3.46-3.26 (m, 4H, overlapping with water peak), 3.00-2.60 (m, 4H), 2.48 (s, 3H, overlapping with solvent peak); MS (ES+) m/z Calcd for $C_{28}H_{28}N_6O_2$: 480.23; found: 481.3 (M+H+).

N1-(3-4-[(benzoylamino)methyl]phenyl-1H-5-pyrazolyl)-4-(4-methylpiperazino)benzamide (Compound 11). $^1$H NMR (400 MHz, DMSO-d6): δ 10.64 (s, 1H), 9.09 (t, J=6.0 Hz, 1H), 7.95-7.90 (m, 6H), 7.37 (d, J=8.0 Hz, 2H), 7.55 (t, J=7.2 Hz, 1H), 7.50-7.46 (m, 2H), 7.39 (d, J=8.0 Hz, 2H), 6.98 (d, J=9.2 Hz, 2H), 4.51 (d, J=6.0 Hz, 2H), 3.28 (t, J=4.8 Hz, 4H), 2.44 (t, J=4.8 Hz, 4H), 2.22 (s, 3H); MS (ES+) m/z Calcd for $C_{29}H_{30}N_6O_2$: 494.24; found: 495.3 (M+H+).

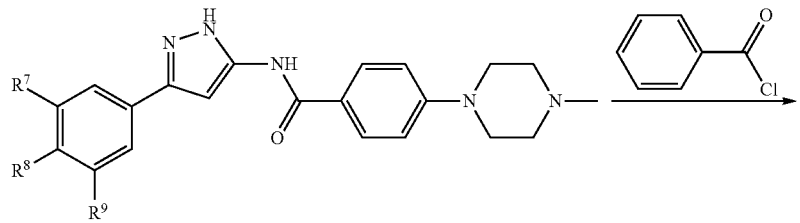

K1 $R^7$ = NH$_2$; $R^8$, $R^9$ = H
K2 $R^7$, $R^9$ = H; $R^8$ = NH$_2$
K8 $R^7$, $R^9$ = H; $R^8$ = CH$_2$NH$_2$

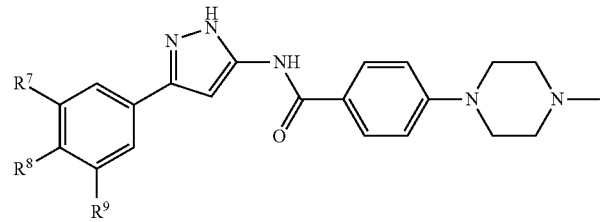

9 $R^7$ = NHC(O)C$_6$H$_5$; $R^9$, $R^8$ = H
10 $R^7$, $R^9$ = H; $R^8$ = NHC(O)C$_6$H$_5$
11 $R^7$, $R^9$ = H; $R^8$ = CH$_2$NHC(O)C$_6$H$_5$

To a solution of K1, K2 or K8 (1.0 equiv) and pyridine (5.0 equiv) in DMSO at room temperature was added benzoyl chloride (1.2 equiv). After 1 h of stirring at room temperature, the reaction was worked up following the same procedure as described in the preparation of compounds J to yield Compounds 9-11.

N1-3-[3-(benzoylamino)phenyl]-1H-5-pyrazolyl-4-(4-methylpiperazino)benzamide (Compound 9). $^1$H NMR (300 MHz, DMSO-d6): δ 12.88 (s, 1H), 10.62 (s, 1H) 10.34 (s, 1H), 8.20 (s, 1H), 7.99 (d, J=8.1 Hz, 2H), 7.93 (d, J=8.7 Hz, 2H), 7.76 (d, J=8.1 Hz, 1H), 7.63-7.40 (m, 5H), 6.98 (d, J=8.7 Hz, 1H), 3.28 (t, J=4.8 Hz, 4H), 2.43 (t, J=4.8 Hz, 4H), 2.21 (s, 3H); MS (ES+) m/z calcd. for $C_{28}H_{28}N_6O_2$: 480.22; found: 481.3 (M+H+).

Example 3

Synthesis of Compounds 12-28

Compounds 12-28 were prepared following the synthetic route shown in the scheme below:

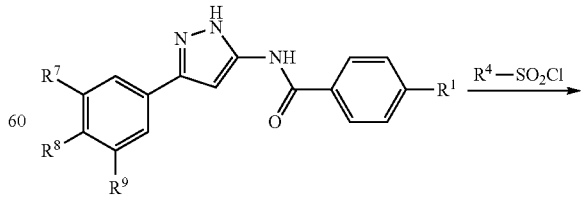

K1 $R^7$ = NH$_2$; $R^8$, $R^9$ = H
K2 $R^7$, $R^9$ = H; $R^8$ = NH$_2$
K8 $R^7$, $R^9$ = H; $R^8$ = CH$_2$NH$_2$

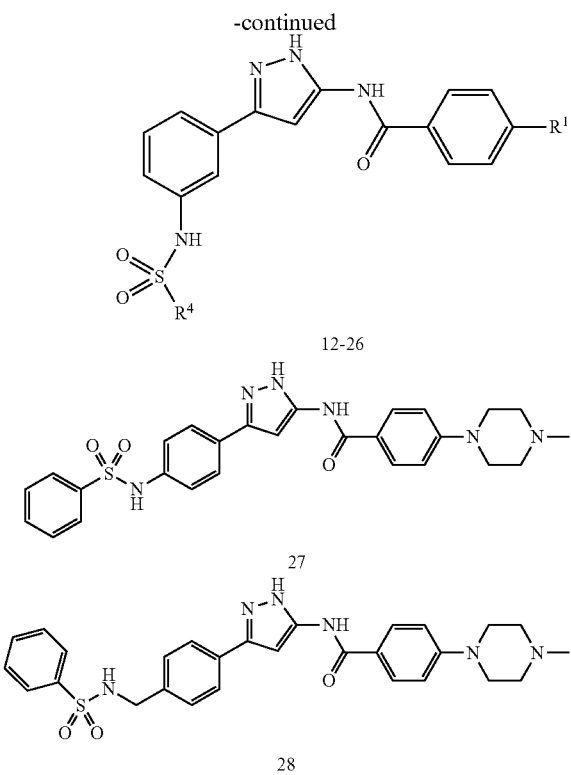

To a solution of K1, K2 or K8 (1.0 equiv) and pyridine (5.0 equiv) in DMSO at room temperature was added sulfonyl chloride R⁴—SO₂Cl (1.2 equiv). After 0.5 h of stirring at room temperature, the reaction was worked up as described for compounds J to yield Compounds 12-28.

N1-(3-3-[(phenylsulfonyl)amino]phenyl-1H-5-pyrazolyl)-4-(4-methylpiperazino)benzamide (Compound 12). $^1$H NMR (400 MHz, DMSO-d6): δ 12.88 (s, 1H), 10.55 (s, 1H), 10.41 (s, 1H), 7.92 (d, J=8.0 Hz, 2H), 7.79 (d, J=7.2 Hz, 2H), 7.62-7.53 (m, 3H), 7.42-7.29 (m, 3H), 7.05-6.98 (m, 4H), 3.29 (t, J=4.8 Hz, 4H), 2.45 (t, J=4.8 Hz, 4H), 2.23 (s, 3H); MS (ES⁺) m/z calcd. for $C_{27}H_{28}N_6O_3S$: 516.62; found: 517.3 (M+H⁺); HRMS (FAB) calcd. for $C_{27}H_{28}N_6O_3S$: 516.1944; found: 516.1937.

N1-[3-(3-[(3-chlorophenyl)sulfonyl]aminophenyl)-1H-5-pyrazolyl]-4-(4-methylpiperazino)benzamide (Compound 13). $^1$H NMR (300 MHz, DMSO-d6): δ 10.63 (s, 1H), 7.93 (d, J=11.0 Hz, 2H), 7.79-7.68 (m, 3H), 7.61-7.55 (m, 3H), 7.50-7.29 (m, 4H), 7.06-6.97 (m, 3H), 6.80 (br s, 1H), 3.28 (br s, 4H), 2.44 (br s, 4H), 2.22 (s, 3H); MS (ES⁺) m/z calcd. for $C_{27}H_{28}N_6O_3S$: 550.06; found: 551.0 (M+H⁺); HRMS (FAB) calcd. for $C_{27}H_{27}ClN_6O_3S$: 550.1554; found: 550.1545.

N1-[3-(3-[(4-chlorophenyl)sulfonyl]aminophenyl)-1H-5-pyrazolyl]-4-(4-methylpiperazino)benzamide (Compound 14). $^1$H NMR (300 MHz, DMSO-d6): δ 12.89 (s, 1H), 12.61 (s, 1H), 10.59 (s, 1H), 7.92 (d, J=8.1 Hz, 2H), 7.67 (d, J=8.7 Hz, 2H), 7.66-7.58 (m, 3H), 7.45-7.31 (m, 3H), 7.05-6.98 (m, 2H), 6.91 (s, 1H), 3.29 (t, J=4.8 Hz, 4H), 2.45 (t, J=4.8 Hz, 4H), 2.23 (s, 3H); MS (ES⁺) m/z calcd. for $C_{27}H_{27}ClN_6O_3S$: 551.06; found: 551.1 (M+H⁺).

N1-[3-(3-[(3-methylphenyl)sulfonyl]aminophenyl)-1H-5-pyrazolyl]-4-(4-methylpiperazino)benzamide (Compound 15). $^1$H NMR (400 MHz, DMSO-d6): δ 12.89 (s, 1H), 10.55 (s, 1H), 10.36 (s, 1H), 7.93 (d, J=8.8 Hz, 2H), 7.63-7.58 (m, 2H), 7.46-7.40 (m, 4H), 7.31 (t, J=8.0 Hz, 1H), 7.05-6.97 (m, 3H), 6.89 (s, 1H), 3.28 (t, J=4.8 Hz, 4H), 2.44 (t, J=4.8 Hz, 4H), 2.34 (s, 3H), 2.22 (s, 3H); MS (ES⁺) m/z calcd. for $C_{28}H_{30}N_6O_3S$: 530.64; found: 531.1 (M+H⁺); HRMS (FAB) calcd. for $C_{28}H_{30}N_6O_3S$: 530.2100; found: 530.2108.

N1-[3-(3-[(4-methylphenyl)sulfonyl]aminophenyl)-1H-5-pyrazolyl]-4-(4-methylpiperazino)benzamide (Compound 16). $^1$H NMR (300 MHz, DMSO-d6): δ 10.59 (s, 1H), 7.93 (d, J=8.7 Hz, 2H), 7.69 (d, J=8.4 Hz, 2H), 7.51-7.27 (m, 5H), 7.07-6.99 (m, 3H), 6.88 (s, 1H), 3.30 (t, J=4.8 Hz, 4H), 2.46 (t, J=4.8 Hz, 4H), 2.33 (s, 3H), 2.24 (s, 3H); MS (ES⁺) m/z calcd. for $C_{28}H_{30}N_6O_3S$: 530.64; found: 531.1 (M+H⁺).

N1-[3-(3-[(4-methoxyphenyl)sulfonyl]aminophenyl)-1H-5-pyrazolyl]-4-(4-methylpiperazino)benzamide (Compound 17). $^1$H NMR (300 MHz, DMSO-d6): δ 12.89 (s, 1H), 10.56 (s, 1H), 7.92 (d, J=8.4 Hz, 2H), 7.73 (dd, J=7.5, 1.5 Hz, 2H), 7.40 (d, J=7.2 Hz, 2H), 7.29 (t, J=7.8 Hz, 1H), 7.09-6.97 (m, 5H), 6.89 (s, 1H), 3.77 (s, 3H), 3.28 (t, J=4.8 Hz, 4H), 2.44 (t, J=4.8 Hz, 4H), 2.22 (s, 3H); MS (ES⁺) m/z calcd. for $C_{28}H_{30}N_6O_4S$: 546.64; found: 547.1 (M+H⁺); HRMS (FAB) calcd. for $C_{28}H_{30}N_6O_4S$: 546.2049; found: 546.2056.

N1-(3-3-[(ethylsulfonyl)amino]phenyl-1H-5-pyrazolyl)-4-(4-methylpiperazino)benzamide (Compound 18). $^1$H NMR (300 MHz, DMSO-d6): δ 12.61 (s, 1H), 10.56 (s, 1H), 9.90 (s, 1H), 7.92 (d, J=8.1 Hz, 2H), 7.47 (d, J=7.8 Hz, 1H), 7.52-7.39 (m, 2H), 7.17 (d, J=6.9 Hz, 1H), 6.98 (d, J=7.8 Hz, 1H), 3.29 (d, J=4.5 Hz, 4H), 3.16-3.14 (m, 2H), 2.44 (t, J=4.5 Hz, 4H), 2.22 (s, 3H), 1.22 (t, J=7.2 Hz, 3H); MS (ES⁺) m/z calcd. for $C_{23}H_{28}N_6O_3S$: 468.6; found: 491.9 (M+Na), 469.1 (M+H⁺).

N1-(3-3-[(propylsulfonyl)amino]phenyl-1H-5-pyrazolyl)-4-(4-methylpiperazino)benzamide (Compound 19). $^1$H NMR (300 MHz, DMSO-d6): δ 12.92 (s, 1H), 10.57 (s, 1H), 9.90 (s, 1H), 7.93 (d, J=8.4 Hz, 2H), 7.52-7.40 (m, 3H), 7.17 (d, J=7.5 Hz, 1H), 7.00-6.97 (m, 3H), 3.29 (t, J=4.8 Hz, 4H), 3.12 (t, J=7.5 Hz, 2H), 2.44 (t, J=4.8 Hz, 4H), 2.22 (s, 3H), 1.71 (qt, J=7.5, 7.5 Hz, 2H), 0.95 (t, J=7.5 Hz, 3H); MS (ES⁺) m/z calcd. for $C_{24}H_{30}N_6O_3S$: 482.59; found: 483.1 (M+H⁺); HRMS (FAB) calcd. for $C_{24}H_{30}N_6O_3S$: 482.2100; found: 482.2103.

N1-(3-3-[(isopropylsulfonyl)amino]phenyl-1H-5-pyrazolyl)-4-(4-methylpiperazino)benzamide (Compound 20). $^1$H NMR (300 MHz, DMSO-d6): δ 10.56 (s, 1H), 7.92 (d, J=7.8 Hz, 1H), 7.45 (d, J=7.8 Hz, 1H), 7.54-7.37 (m, 2H), 7.19 (d, J=7.8 Hz, 1H), 6.99 (d, J=8.4 Hz, 1H), 3.29 (t, J=4.8 Hz, 4H), 2.44 (t, J=4.8 Hz, 4H), 2.22 (s, 3H), 1.81 (s, 1H), 1.27 (s, 3H), 1.25 (s, 3H); MS (ES⁺) m/z calcd. for $C_{24}H_{30}N_6O_3S$: 482.6; found: 505.1 (M+Na), 483.1 (M+H⁺).

N1-(3-3-[(phenylsulfonyl)amino]phenyl-1H-5-pyrazolyl)-3-(4-methylpiperazino)benzamide (Compound 21). $^1$H NMR (400 MHz, DMSO-d6): δ 12.96 (s, 1H), 10.86 (s, 1H), 10.43 (s, 1H), 7.80 (d, J=7.2 Hz, 2H), 7.62-7.53 (m, 4H), 7.43-7.39 (m, 3H), 7.34-7.28 (m, 2H), 7.12 (d, J=6.4 Hz, 1H), 7.05 (d, J=8.0 Hz, 1H), 6.91 (s, 1H), 3.23 (t, J=4.8 Hz, 4H), 2.48 (t, J=4.8 Hz, 4H), 2.24 (s, 3H); MS (ES⁺) m/z calcd. for $C_{27}H_{28}N_6O_3S$: 516.62; found: 517.1 (M+H⁺); HRMS (FAB) calcd. for $C_{27}H_{28}N_6O_3S$: 516.1944; found: 516.1952.

N1-(3-3-[(phenylsulfonyl)amino]phenyl-1H-5-pyrazolyl)-4-morpholino benzamide (Compound 22). $^1$H NMR (300 MHz, DMSO-d6): δ 12.86 (s, 1H), 10.59 (s, 1H), 10.39 (s, 1H), 7.94 (d, J=10.8 Hz, 2H), 7.79 (d, J=11.2 Hz, 2H), 7.63-7.52 (m, 3H), 7.45-7.40 (m, 2H), 7.29 (t, J=10.0 Hz, 1H), 7.02 (t, J=12.0 Hz, 3H), 6.87 (br s, 1H), 3.74 (t, J=6.0 Hz, 4H), 3.26 (t, J=6.0 Hz, 4H); MS (ES⁺) m/z calcd. for $C_{26}H_{25}N_5O_4S$: 503.57; found: 504.0 (M+H⁺).

N1-(3-3-[(phenylsulfonyl)amino]phenyl-1H-5-pyrazolyl)-3-morpholino benzamide (Compound 23). $^1$H NMR (400 MHz, DMSO-d6): δ 12.96 (s, 1H), 10.87 (s, 1H), 10.42 (s, 1H), 7.80 (d, J=8.4 Hz, 2H), 7.63-7.53 (m, 4H), 7.46-7.41 (m, 3H), 7.35 (t, J=8.0 Hz, 1H), 7.30 (t, J=8.0 Hz, 1H), 7.15 (d, J=8.4 Hz, 1H), 7.05 (d, J=8.0 Hz, 1H), 6.92 (br s, 1H), 3.77 (t, J=4.8 Hz, 4H), 3.20 (t, J=4.8 Hz, 4H); MS (ES⁺) m/z calcd. for $C_{26}H_{25}N_5O_4S$: 503.57; found: 504.0 (M+H⁺).

N1-(3-3-[(phenylsulfonyl)amino]phenyl-1H-5-pyrazolyl)-4-(2-tetrahydro-1H-1-pyrrolylethoxy)benzamide (Compound 24). $^1$H NMR (300 MHz, DMSO-d6): δ 10.87 (s, 1H), 10.46 (s, 1H), 8.05 (d, J=8.7 Hz, 2H), 7.79 (d, J=6.9 Hz, 2H), 7.61-7.41 (m, 4H), 7.31-7.26 (m, 2H), 7.12-7.03 (m, 3H), 6.78 (s, 1H), 4.43 (t, J=4.8 Hz, 2H), 3.59 (br, 4H), 3.14-3.04 (m, 2H), 2.00-1.86 (m, 4H); MS (ES$^+$) m/z calcd. for $C_{28}H_{29}N_5O_4S$: 531.63; found: 532.1 (M+H$^+$); HRMS (FAB) calcd. for $C_{28}H_{29}N_5O_4S$: 531.1940; found: 531.1944.

N1-(3-3-[(phenylsulfonyl)amino]phenyl-1H-5-pyrazolyl)-4-(2-morpholinoethoxy)benzamide (Compound 25). $^1$H NMR (400 MHz, DMSO-d6): δ 12.92 (s, 1H), 10.73 (s, 1H), 10.41 (s, 1H), 8.00 (d, J=8.4 Hz, 2H), 7.79 (d, J=6.8 Hz, 2H), 7.63-7.55 (m, 3H), 7.43-7.37 (m, 2H), 7.30 (t, J=8.0 Hz, 1H), 7.05 (d, J=7.6 Hz, 1H), 6.89 (s, 1H), 4.17 (t, J=5.6 Hz, 2H), 3.58 (t, J=4.8 Hz, 4H), 2.71 (t, J=5.6 Hz, 2H), 2.48 (t, J=4.8 Hz, 4H); MS (ES$^+$) m/z calcd. for $C_{28}H_{29}N_5O_5S$: 547.63; found: 548.2 (M+H$^+$).

N1-(3-3-[(phenylsulfonyl)amino]phenyl-1H-5-pyrazolyl)-4-(morpholinomethyl)benzamide (Compound 26). $^1$H NMR (400 MHz, DMSO-d6): δ 12.99 (s, 1H), 10.91 (s, 1H), 10.45 (s, 1H), 8.02 (d, J=5.6 Hz, 2H), 7.80 (d, J=6.8 Hz, 2H), 7.63-7.53 (m, 4H), 7.43 (d, J=8.0 Hz, 1H), 7.35-7.28 (m, 3H), 7.06 (d, J=8.0 Hz, 1H), 6.92 (s, 1H), 3.63 (br s, 6H), 2.41 (br s, 4H); MS (ES$^+$) m/z calcd. for $C_{27}H_{27}N_5O_4S$: 517.60; found: 518.1 (M+H$^+$); HRMS (FAB) calcd. for $C_{27}H_{27}N_5O_4S$: 517.1784; found: 517.1793.

N1-(3-4-[(phenylsulfonyl)amino]phenyl-1H-5-pyrazolyl)-4-(4-methylpiperazino)benzamide (Compound 27). $^1$H NMR (300 MHz, DMSO-d6): δ 12.73 (s, 1H), 10.48 (s, 1H), 10.44 (s, 1H), 7.91 (d, J=8.7 Hz, 2H), 7.79 (d, J=6.6 Hz, 2H), 7.64-7.53 (m, 5H), 7.15 (d, J=8.4 Hz, 2H), 6.97 (d, J=8.4 Hz, 1H), 6.91 (s, 1H), 3.28 (t, J=4.8 Hz, 4H), 2.44 (t, J=4.8 Hz, 4H), 2.22 (s, 3H); MS (ES$^+$) m/z calcd. for $C_{27}H_{28}N_6O_3S$: 516.62; found: 517.2 (M+H$^+$); HRMS (FAB) calcd. for $C_{27}H_{28}N_6O_3S$: 516.1944; found: 516.1951.

N1-[3-(4-[(phenylsulfonyl)amino]methylphenyl)-1H-5-pyrazolyl]-4-(4-methylpiperazino)benzamide (Compound 28). $^1$H NMR (300 MHz, DMSO-d6): δ 10.51 (s, 1H), 8.21 (t, J=6.3 Hz, 1H), 7.93 (d, J=78.7 Hz, 2H), 7.83-7.80 (m, 2H), 7.67-7.58 (m, 4H), 7.34-7.29 (m, 4H), 7.00-6.97 (m, 3H), 4.01 (d, J=6.3 Hz, 2H), 3.29 (br s, 4H), 2.45 (br s, 4H), 2.23 (s, 3H). MS (ES$^+$) m/z Calcd for $C_{28}H_{30}N_6O_3S$: 530.21; found: 5311.2 (M+H$^+$).

Example 4

Synthesis of Compounds 29-66

Below is a general synthetic scheme for the synthesis of Compounds 29-66:

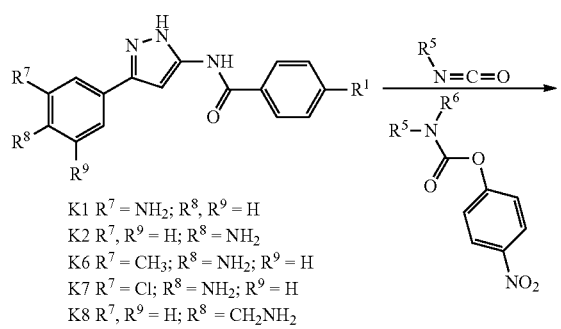

K1 R$^7$ = NH$_2$; R$^8$, R$^9$ = H
K2 R$^7$, R$^9$ = H; R$^8$ = NH$_2$
K6 R$^7$ = CH$_3$; R$^8$ = NH$_2$; R$^9$ = H
K7 R$^7$ = Cl; R$^8$ = NH$_2$; R$^9$ = H
K8 R$^7$, R$^9$ = H; R$^8$ = CH$_2$NH$_2$

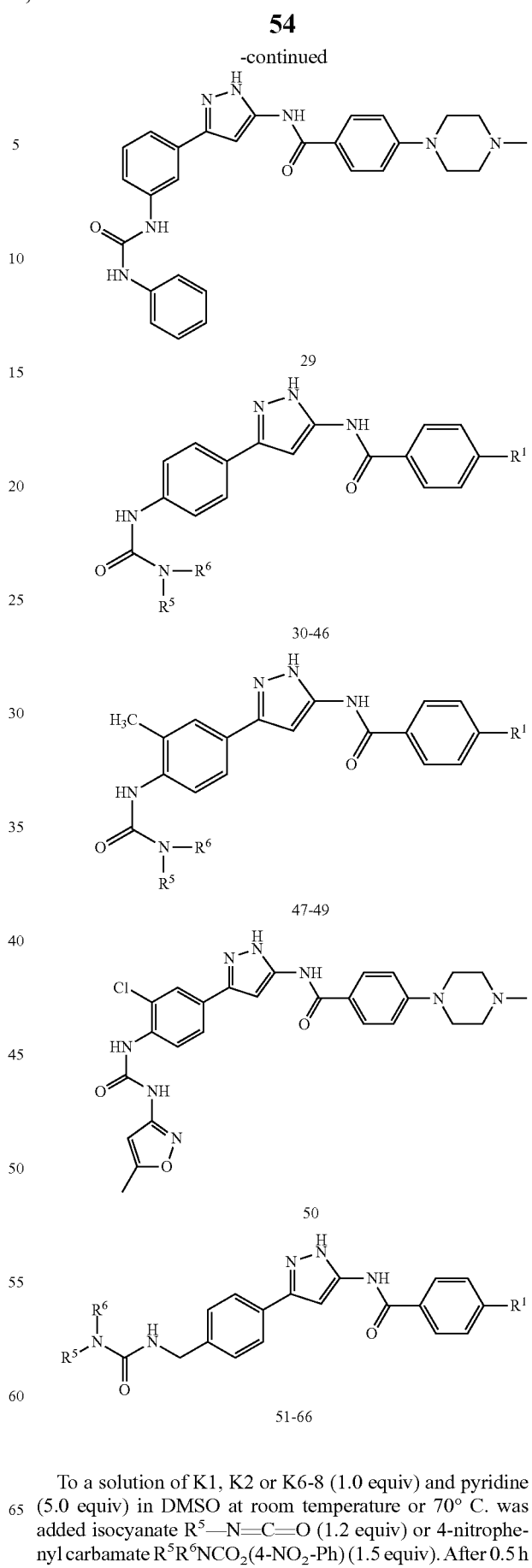

To a solution of K1, K2 or K6-8 (1.0 equiv) and pyridine (5.0 equiv) in DMSO at room temperature or 70° C. was added isocyanate R$^5$—N=C=O (1.2 equiv) or 4-nitrophenyl carbamate R$^5$R$^6$NCO$_2$(4-NO$_2$-Ph) (1.5 equiv). After 0.5 h of stirring at room temperature, the reaction was worked up as described for compounds J to yield Compounds 29-66.

N1-(3-{3-[(anilinocarbonyl)amino]phenyl}-1H-5-pyrazolyl)-4-(4-methylpiperazino)benzamide (Compound 29). $^1$H NMR (300 MHz, DMSO-d6): δ 12.85 (s, 1H), 10.57 (s, 1H), 8.81 (d, J=10.8 Hz, 2H), 7.93 (d, J=8.7 Hz, 2H), 7.89 (s, 1H), 7.48 (d, J=7.8 Hz, 2H), 7.35-7.24 (m, 5H), 6.99-6.94 (m, 3H), 3.28 (t, J=4.8 Hz, 4H), 2.44 (t, J=4.8 Hz, 4H), 2.22 (s, 3H); MS (ES$^+$) m/z calcd. for $C_{28}H_{29}N_7O_2$: 495.24; found: 496.3 (M+H$^+$).

N1-(3-4-[(anilinocarbonyl)amino]phenyl-1H-5-pyrazolyl)-4-(4-methylpiperazino)benzamide (Compound 30). $^1$H NMR (400 MHz, DMSO-d6): δ 12.68 (bs, 1H), 10.54 (s, 1H), 9.22 (s, 1H), 9.11 (s, 1H), 7.93 (d, J=8.8 Hz, 2H), 7.65 (d, J=8.8 Hz, 2H), 7.52 (d, J=8.8 Hz, 2H), 7.45 (d, J=7.6 Hz, 2H), 7.27 (t, J=7.6 Hz, 2H), 7.02-6.88 (m, 3H), 6.86 (bs, 1H), 3.40-3.20 (m, 4H, overlapping with water peak), 2.64-2.60 (m, 4H), 2.35 (s, 3H); MS (ES$^+$) m/z Calcd for $C_{28}H_{29}N_7O_2$: 495.24; found: 496.2 (M+H$^+$).

N1-[3-(4-[(ethylamino)carbonyl]aminophenyl)-1H-5-pyrazolyl]-4-(4-methylpiperazino)benzamide (Compound 31). $^1$H NMR (300 MHz, DMSO-d6): δ 12.67 (s, 1H), 10.47 (s, 1H), 8.57 (s, 1H), 7.93 (d, J=8.4 Hz, 2H), 7.59 (d, J=8.4 Hz, 2H), 7.46 (d, J=8.4 Hz, 2H), 6.97 (d, J=8.7 Hz, 2H), 6.90 (bs, 1H), 6.17 (t, J=5.3 Hz, 1H), 4.153.29-3.26 (m, 4H), 3.16-3.07 (m, 2H), 2.45-2.42 (m, 4H), 2.22 (s, 3H), 1.06(t, J=7.2 Hz, 2H); MS(ES$^+$) m/z calcd, for $C_{24}H_{29}N_7O_2$: 447.24; found: 448.1 (M+H$^+$).

N1-3-[4-([(5-methyl-3-isoxazolyl)amino]carbonylamino) phenyl]-1H-5-pyrazolyl-4-(4-methylpiperazino)benzamide HCl salt (Compound 32). $^1$H NMR (400 MHz, DMSO-d6): δ 10.64 (s, 1H), 10.42 (bs, 1H), 9.61 (s, 1H), 9.23 (s, 1H), 7.97 (d, J=8.8 Hz, 2H), 7.67 (d, J=8.8 Hz, 2H), 7.51 (d, J=8.8 Hz, 2H), 7.06 (d, J=8.8 Hz, 2H), 6.88 (s, 1H), 6.54 (s, 1H), 4.08-4.00 (m, 2H), 3.54-3.40 (m, 2H, overlapping with water peak), 3.18-3.06 (m, 4H), 2.81 (d, J=4.4 Hz, 3H), 2.35 (s, 3H); MS (ES$^+$) m/z Calcd for $C_{26}H_{28}N_8O_3$: 500.23; found: 501.1 (M+H$^+$).

N1-[3-(4-[(2-pyridylamino)carbonyl]aminophenyl)-1H-5-pyrazolyl]-4-(4-methylpiperazino)benzamide (Compound 33). $^1$H NMR (300 MHz, DMSO-d6): δ 10.68 (s, 1H), 10.49 (s, 1H), 9.51 (s, 1H), 7.80 (dd, J=1.2, 4.8 Hz, 2H), 7.93 (d, J=8.4 Hz, 2H), 7.79-7.73 (m, 2H), 7.70 (d, J=8.4 Hz, 2H), 7.61 (d, J=8.4 Hz, 2H), 7.50 (d, J=8.4 Hz, 2H), 7.02-7.05 (m, 2H), 6.99 (d, J=10.5 Hz, 2H), 3.28 (t, J=4.8 Hz, 4H), 2.44 (t, J=4.8 Hz, 4H), 2.22 (s, 3H); MS (ES$^+$) m/z Calcd for $C_{27}H_{28}N_8O_2$: 496.23; found: 497.0 (M+H$^+$).

N1-3-[4-([(5-methyl-1,3-thiazol-2-yl)amino]carbonylamino)phenyl]-1H-5-pyrazolyl-4-(4-methylpiperazino)benzamide (Compound 34). $^1$H NMR (300 MHz, DMSO-d6): δ 10.52 (s, 1H), 10.49 (s, 1H), 9.09 (s, 1H), 7.93 (d, J=9.0 Hz, 2H), 7.89 (d, J=9.0 Hz, 1H), 7.81 (d, J=8.7 Hz, 1H), 7.69 (d, J=8.7 Hz, 2H), 7.60 (d, J=8.7 Hz, 1H), 7.55 (d, J=8.7 Hz, 2H), 7.04-6.97 (m, 3H), 3.29 (t, J=4.8 Hz, 4H), 2.45 (t, J=4.8 Hz, 4H), 2.32 (s, 3H), 2.23 (s, 3H); MS (ES$^+$) m/z Calcd for $C_{26}H_{28}N_8O_2S$: 516.21; found: 517.0 (M+H$^+$).

N1-[3-(4-[(2,5-difluoroanilino)carbonyl]aminophenyl)-1H-5-pyrazolyl]-4-(4-methylpiperazino)benzamide (Compound 35). $^1$H NMR (400 MHz, DMSO-d6): δ 12.75 (s, 1H), 10.50 (s, 1H), 9.27 (s, 1H), 8.88 (s, 1H), 8.06 (ddd, J=3.2, 6.4, 10.8 Hz, 1H), 7.93 (d, J=8.4 Hz, 2H), 7.69 (d, J=8.4 Hz, 2H), 7.53 (d, J=8.4 Hz, 2H), 7.30 (ddd, J=5.2, 9.2, 14.4 Hz, 1H), 6.99-6.97 (m, 3H), 6.86-6.80 (m, 1H), 3.29 (t, J=4.8 Hz, 4H), 2.45 (t, J=4.8 Hz, 4H), 2.23 (s, 3H); MS (ES$^+$) m/z Calcd for $C_{28}H_{27}F_2N_7O_2$: 531.22; found: 532.1 (M+H$^+$).

N1-(3-4-[([5-(tert-butyl)-3-isoxazolyl]aminocarbonyl) amino]phenyl-1H-5-pyrazolyl)-4-(4-methylpiperazino)benzamide (Compound 37). $^1$H NMR (400 MHz, DMSO-d6): δ 12.74 (s, 1H), 10.51 (s, 1H), 9.58 (s, 1H), 8.99 (s, 1H), 7.92 (d, J=9.2 Hz, 2H), 7.69 (d, t, J=8.4 Hz, 2H), 7.53 (d, J=8.8 Hz, 2H), 6.99-6.92 (m, 3H), 6.53 (s, 1H), 3.29-3.27 (m, 4H), 2.47-2.43 (m, 4H), 2.23 (s, 3H), 1.27 (s, 9H); MS(ES$^+$) m/z calcd, for $C_{29}H_{34}N_8O_3$: 542.28; found: 543.1 (M+H$^+$).

N1-3-[4-([(5-methyl-3-isoxazolyl)amino]carbonylamino) phenyl]-1H-5-pyrazolyl-4-(3-tetrahydro-1H-1-pyrrolylpropoxy)benzamide (Compound 38). $^1$H NMR (300 MHz, DMSO-d6): δ 12.79 (s, 1H), 10.68 (s, 1H), 9.58 (s, 1H), 9.12 (s, 1H), 8.00 (d, J=8.1 Hz, 2H), 7.68 (d, J=8.1 Hz, 2H), 7.52 (d, J=8.1 Hz, 2H), 7.01 (d, J=8.1 Hz, 2H), 6.93 (s, 1H), 6.55 (s, 1H), 4.08 (t, J=5.9 Hz, 2H), 2.63-2.54 (m, 6H), 2.36 (s, 3H), 1.92 (t, J=6.6 Hz, 2H), 1.70 (s, 1H); MS (ES$^+$) m/z calcd. for $C_{28}H_{31}N_7O_4$:529.24; found: 530.1 (M+H$^+$).

N1-3-[4-([(5-methyl-3-isoxazolyl)amino]carbonylamino) phenyl]-1H-5-pyrazolyl-4-(2-tetrahydro-1H-1-pyrrolylethoxy)benzamide (Compound 40). $^1$H NMR (400 MHz, DMSO-d6): δ 12.79 (s, 1H), 10.66 (s, 1H), 9.51 (s, 1H), 8.95 (s, 1H), 8.01 (d, J=8.4 Hz, 2H), 7.69 (d, t, J=8.8 Hz, 2H), 7.53 (d, J=8.4 Hz, 2H), 7.03 (d, J=8.4 Hz, 2H), 6.97 (s, 1H), 6.56 (s, 1H), 4.15 (t, J=5.8 Hz, 2H), 2.81 (t, J=5.8 Hz, 2H), 2.52-2.51 (m, 4H, overlapping with solvent peak), 2.37 (s, 3H), 1.72-1.66 (m, 4H); MS(ES$^+$) m/z calcd, for $C_{27}H_{29}N_7O_4$: 515.23; found: 516.6 (M+H$^+$).

N1-(3-4-[([5-(tert-butyl)-3-isoxazolyl]aminocarbonyl) amino]phenyl-1H-5-pyrazolyl)-4-(2-tetrahydro-1H-1-pyrrolylethoxy)benzamide (Compound 41). $^1$H NMR (400 MHz, DMSO-d6): δ 13.59 (s, 1H), 11.48 (s, 1H), 10.39 (s, 1H), 9.80 (s, 1H), 8.82 (d, J=8.8 Hz, 2H), 8.50 (d, J=8.8 Hz, 2H), 8.34 (d, J=8.4 Hz, 2H), 7.85 (d, J=8.8 Hz, 2H), 7.77 (br s, 1H), 7.32 (s, 1H), 4.96 (t, J=5.8 Hz, 2H), 2.11 (s, 9H); MS(ES$^+$) m/z calcd, for $C_{30}H_{35}N_7O_4$: 557.64; found: 558.6 (M+H$^+$).

N1-3-[4-([(5-methyl-3-isoxazolyl)amino]carbonylamino) phenyl]-1H-5-pyrazolyl-4-[(4-methylpiperazino)methyl] benzamide (Compound 42). $^1$H NMR (400 MHz, DMSO-d6): δ 12.82 (s, 1H), 10.79 (s, 1H), 9.52 (s, 1H), 8.96 (s, 1H) 7.97 (d, J=8.0 Hz, 2H), 7.69 (d, J=8.4 Hz, 2H), 7.52 (d, J=8.4 Hz, 2H), 7.40 (d, J=8.4 Hz, 2H), 6.96 (br s, 1H), 6.58 (s, 1H), 3.51 (s, 2H), 3.35 (m, 4H, overlapping with water peak), 2.36 (br s, 7H), 2.14 (s, 3H). MS (ES$^+$) m/z calcd. for $C_{27}H_{30}N_8O_3$: 514.24; found: 537.2 (M+Na), 515.3 (M+H$^+$).

N1-(3-4-[([5-(tert-butyl)-3-isoxazolyl]aminocarbonyl) amino]phenyl-1H-5-pyrazolyl)-4-[(4-methylpiperazino)methyl]benzamide (Compound 43). $^1$H NMR (300 MHz, DMSO-d6): δ 10.79 (s, 1H), 9.73 (s, 1H), 9.23 (s, 1H), 7.98 (d, J=8.1 Hz, 2H), 7.69 (d, J=8.4 Hz, 2H), 7.54 (d, J=8.4 Hz, 2H), 7.41 (d, J=8.1 Hz, 2H), 6.97 (s, 1H), 6.52 (s, 1H), 3.51 (d, J=5.1 Hz, 2H), 3.28 (t, J=4.8 Hz, 4H), 2.37 (t, J=4.8 Hz, 4H), 2.16 (s, 3H), 1.30 (s, 9H); MS (ES$^+$) m/z Calcd for $C_{30}H_{36}N_8O_3$: 556.29; found: 557.4 (M+H$^+$).

N1-(3-4-[([5-(tert-butyl)-3-isoxazolyl]aminocarbonyl) amino]phenyl-1H-5-pyrazolyl)-4-(2-morpholinoethoxy) benzamide (Compound 44). $^1$H NMR (400 MHz, DMSO-d6): 12.79 (s, 1H), 10.67 (s, 1H), 9.57 (s, 1H), 8.94 (s, 1H), 8.01 (d, J=8.8 Hz, 2H), 7.69 (d, J=8.4 Hz, 2H), 7.53 (d, J=8.8 Hz, 2H), 7.04 (d, J=8.8 Hz, 2H), 6.96 (bs, 1H), 6.52 (s, 1H), 4.17 (t, J=5.8 Hz, 2H), 3.58 (t, J=4.6 Hz, 4H), 2.71 (t, J=5.8 Hz, 2H), 2.48-2.47(m, 4H, overlapping with solvent peak), 1.30(s, 9H); MS(ES$^+$) m/z calcd, for $C_{30}H_{35}N_7O_5$: 573.27; found: 574.2 (M+H$^+$).

N1-[3-(4-[(3-fluoroanilino)carbonyl]aminophenyl)-1H-5-pyrazolyl]-4-(2-morpholinoethoxy)benzamide (Compound 45). $^1$H NMR (300 MHz, DMSO-d6): δ 12.77 (s, 1H), 10.69 (s, 1H), 9.35 (s, 1H), 9.25 (s, 1H), 8.02 (d, J=9.0 Hz, 2H), 7.68 (d, J=8.7 Hz, 2H), 7.56-7.49 (m, 2H), 7.34-7.27 (m, 1H), 7.13 (dd, J=8.4 Hz, 0.6 Hz, 1H), 7.05 (d, J=8.7 Hz, 2H), 6.92 (s, 1H), 6.78 (t,d, J=8.4 Hz, 1.8 Hz, 1H), 4.19 (s, 2H), 3.61-3.50 (m, 4H), 2.76-2.73 (m, 2H), 2.51-2.49 (m, 4H, overlapping with solvent peak); MS(ES$^+$) m/z calcd, for $C_{29}H_{29}FN_6O_4$: 544.22; found: 545.1 (M+H$^+$).

N1-3-[4-([(5-methyl-3-isoxazolyl)amino]carbonylamino)phenyl]-1H-5-pyrazolyl-4-(2-morpholinoethoxy)benzamide (Compound 46a). $^1$H NMR (300 MHz, DMSO-d6): δ 12.80 (s, 1H), 10.67 (s, 1H), 9.53 (s, 1H), 8.96 (s, 1H), 7.99 (d, J=8.4 Hz, 2H), 7.66 (d, J=7.8 Hz, 2H), 7.50 (d, J=8.4 Hz, 2H), 7.01 (d, J=8.1 Hz, 2H), 6.94 (s, 1H), 6.53 (s, 1H), 4.14 (t, J=5.6 Hz, 2H), 3.55 (t, J=4.5 Hz, 4H), 2.68 (t, J=5.6 Hz, 2H), 2.50-2.46 (m, 4H, overlapped with DMSO), 2.34 (s, 3H); MS (ES$^+$) m/z calcd. for $C_{27}H_{29}N_7O_5$: 531.22; found: 554.1 (M+Na), 532.0 (M+H$^+$).

N1-3-[4-([(5-ethyl-3-isoxazolyl)amino]carbonylamino)-3-methylphenyl]-1H-5-pyrazolyl-4-(2-morpholinoethoxy)benzamide (46b). $^1$H NMR (400 MHz, DMSO-d6): δ 12.77 (s, 1H), 10.65 (s, 1H), 9.91 (s, 1H), 8.36 (s, 1H), 8.03-7.98 (m, 3H), 7.61-7.55 (m, 2H), 7.04-6.98 (m, 3H), 6.52 (s, 1H), 4.17 (t, J=5.6 Hz, 2H), 3.58 (t, J=4.8 Hz, 4H), 2.75-2.70 (m, 4H), 2.50-2.47 (m, 4H, overlapping with DMSO peak), 2.30 (s, 3H), 1.22 (t, J=7.6 Hz, 3H); MS (ES$^+$) m/z calcd. for $C_{29}H_{33}N_7O_5$: 559.25; found: 560.3 (M+H$^+$).

N1-3-[4-([(5-cyclopropyl-3-isoxazolyl)amino]carbonylamino)-3-methylphenyl]-1H-5-pyrazolyl-4-(2-morpholinoethoxy)benzamide (46c). $^1$H NMR (400 MHz, DMSO-d6): δ 12.77 (s, 1H), 10.66 (s, 1H), 9.89 (s, 1H), 8.34 (s, 1H), 8.02-7.97 (m, 3H), 7.61-7.55 (m, 2H), 7.05-6.98 (m, 3H), 6.45 (s, 1H), 4.17 (t, J=5.6 Hz, 2H), 3.58 (t, J=4.8 Hz, 4H), 2.71 (t, J=5.6 Hz, 2H), 2.54-2.48 (m, 4H, overlapping with DMSO peak), 2.29 (s, 3H), 2.15-2.08 (m, 1H), 1.07-1.03 (m, 2H), 0.91-0.87 (m, 2H); MS (ES$^+$) m/z calcd. for $C_{30}H_{33}N_7O_5$: 571.25; found: 572.3 (M+H$^+$).

N1-3-[3-methyl-4-([(5-methyl-3-isoxazolyl)amino]carbonylamino)phenyl]-1H-5-pyrazolyl-4-(4-methylpiperazino)benzamide (Compound 47). $^1$H NMR (400 MHz, DMSO-d6): δ 12.73 (s, 1H), 10.49 (s, 1H), 9.88 (s, 1H), 8.35 (s, 1H), 7.97-7.91 (m, 3H), 7.60 (s, 1H), 7.55 (d, J=8.4 Hz, 1H), 6.97 (d, J=8.0 Hz, 3H), 6.51 (s, 1H), 3.27 (t, J=4.8 Hz, 4H), 2.42 (t, J=4.8 Hz, 4H), 2.36 (s, 3H), 2.29 (s, 3H), 2.21 (s, 3H); MS (ES$^+$) m/z calcd. for $C_{27}H_{30}N_8O_3$: 514.24; found: 515.2 (M+H$^+$).

N1-3-[3-methyl-4-([(5-methyl-3-isoxazolyl)amino]carbonylamino)phenyl]-1H-5-pyrazolyl-4-[(4-methylpiperazino)methyl]benzamide (Compound 48a). $^1$H NMR (300 MHz, DMSO-d6): δ 10.78 (s, 1H), 9.89 (s, 1H), 8.36 (s, 1H), 7.99-7.97 (m, 3H), 7.62 (s, 1H), 7.57 (d, J=8.7 Hz, 1H), 7.41 (d, J=8.1 Hz, 2H), 7.00 (s, 1H), 6.52 (s, 1H), 3.52 (s, 2H), 3.36 (s, 4H), 2.37 (s, 7H), 2.30 (s, 3H), 2.15 (s, 3H); MS (ES$^+$) m/z Calcd for $C_{28}H_{32}N_8O_3$: 528.26; found: 529.3 (M+H$^+$).

N1-3-[4-([(5-ethyl-3-isoxazolyl)amino]carbonylamino)-3-methylphenyl]-1H-5-pyrazolyl-4-[(4-methylpiperazino)methyl]benzamide (48b). $^1$H NMR (400 MHz, DMSO-d6): δ 12.80 (s, 1H), 10.77 (s, 1H), 9.91 (s, 1H), 8.36 (s, 1H), 7.99-7.97 (m, 3H), 7.62-7.56 (m, 2H), 7.41 (d, J=8.0 Hz, 2H), 7.00 (s, 1H), 6.52 (s, 1H), 3.50 (s, 2H), 3.17 (d, J=4.8 Hz, 3H), 2.67 (q, J=7.6 Hz, 2H), 2.37 (br s, 8H), 2.15 (s, 3H), 1.22 (t, J=7.6 Hz, 3H); MS (ES$^+$) m/z calcd. for $C_{29}H_{34}N_8O_3$: 542.28; found: 543.3 (M+H$^+$).

N1-(3-4-[([5-(tert-butyl)-3-isoxazolyl]aminocarbonyl)amino]-3-methylphenyl-1H-5-pyrazolyl)-4-[(4-methylpiperazino)methyl]benzamide (Compound 49). $^1$H NMR (300 MHz, DMSO-d6): δ 10.78 (s, 1H), 9.95 (s, 1H), 8.35 (s, 1H), 7.99-7.97 (m, 3H), 7.73 (s, 1H), 7.57 (d, J=8.4 Hz, 1H), 7.41 (d, J=8.1 Hz, 2H), 7.11 (s, 1H), 6.48 (s, 1H), 3.52 (s, 2H), 3.35 (s, 4H), 2.37 (s, 4H), 2.30 (s, 3H), 2.15 (s, 3H), 1.30 (s, 9H); MS (ES$^+$) m/z Calcd for $C_{31}H_{38}N_8O_3$: 570.31; found: 571.4 (M+H$^+$).

N1-3-[3-chloro-4-([(5-methyl-3-isoxazolyl)amino]carbonylamino)phenyl]-1H-5-pyrazolyl-4-(4-methylpiperazino)benzamide (Compound 50). $^1$H NMR (400 MHz, DMSO-d6): δ 12.88 (s, 1H), 10.54 (s, 1H), 10.25 (s, 1H), 8.81 (s, 1H), 8.24 (d, J=8.4 Hz, 1H), 7.94-7.91 (m, 3H), 7.71 (d, J=8.8 Hz, 1H), 7.05-6.98 (m, 3H), 6.52 (s, 1H), 3.28 (t, J=4.8 Hz, 4H), 2.44 (t, J=4.8 Hz, 4H), 2.38 (s, 3H), 2.22 (s, 3H); MS (ES$^+$) m/z calcd. for $C_{26}H_{27}ClN_8O_3$: 534.19; found: 535.2 (M+H$^+$).

N1-[3-[4-[(anilinocarbonyl)amino]methylphenyl]-1H-5-pyrazolyl]-4-(4-methylpiperazino)benzamide (Compound 51). $^1$H NMR (400 MHz, DMSO-d6): δ 12.83 (s, 1H), 10.51 (s, 1H), 8.58 (s, 1H), 7.93 (d, J=8.0 Hz, 2H), 7.71 (d, J=7.2 Hz, 2H), 7.43-7.35 (m, 4H), 7.22 (t, J=7.6 Hz, 2H), 7.08-6.85 (m, 3H), 6.89 (t, J=7.2 Hz, 1H), 6.64 (s, 1H), 4.33 (d, J=5.2 Hz, 2H), 3.32-3.20 (m, 4H, overlapping with water peak), 2.48-2.40 (m, 4H, overlapping with solvent peak), 2.22 (s, 3H); MS (ES$^+$) m/z Calcd for $C_{29}H_{31}N_7O_2$: 509.25; found: 510.2 (M+H$^+$).

N1-3-[4-([(2,5-difluoroanilino)carbonyl]aminomethyl)phenyl]-1H-5-pyrazolyl-4-(4-methylpiperazino)benzamide (Compound 52). $^1$H NMR (400 MHz, DMSO-d6): δ 12.84 (s, 1H), 10.51 (s, 1H), 8.66 (s, 1H), 8.06-8.01 (m, 1H), 7.92 (d, J=8.4 Hz, 2H), 7.73 (d, J=8.0 Hz, 2H), 7.38 (d, J=8.0 Hz, 2H), 7.26-7.20 (m, 2H), 7.04-6.93 (m, 2H), 6.77-6.71 (m, 1H), 4.35 (d, J=6.0 Hz, 2H), 3.29-3.27 (m, 4H), 2.46-2.43 (m, 4H), 2.22 (s, 3H); MS(ES$^+$) m/z calcd, for $C_{29}H_{29}F_2N_7O_2$: 545.24; found: 546.1 (M+H$^+$).

N1-(3-4-[([(5-methyl-3-isoxazolyl)amino]carbonylamino)methyl]phenyl-1H-5-pyrazolyl)-4-(4-methylpiperazino)benzamide (Compound 53). $^1$H NMR (400 MHz, DMSO-d6): δ 12.83 (s, 1H), 10.52 (s, 1H), 9.42 (s, 1H), 7.91 (d, J=8.0 Hz, 2H), 7.69 (d, J=7.6 Hz, 2H), 7.33 (d, J=7.6 Hz, 2H), 7.03-6.88 (m, 4H), 6.39 (s, 1H), 4.32 (d, J=5.2 Hz, 2H), 3.28-3.18 (m, 4H), 2.48-2.38 (m, 4H), 2.31 (s, 3H), 2.20 (s, 3H); MS (ES$^+$) m/z Calcd for $C_{27}H_{30}N_8O_3$: 514.24; found: 515.3 (M+H$^+$).

N1-[3-(4-[([5-(tert-butyl)-3-isoxazolyl]aminocarbonyl)amino]methylphenyl)-1H-5-pyrazolyl]-4-(4-methylpiperazino)benzamide (Compound 54). $^1$H NMR (400 MHz, DMSO-d6): δ 12.84 (s, 1H), 10.52 (s, 1H), 9.49 (s, 1H), 7.91 (d, J=8.8 Hz, 2H), 7.69 (d, J=7.6 Hz, 2H), 7.33 (d, J=7.6 Hz, 2H), 7.06-6.92 (m, 4H), 6.36 (s, 1H), 4.32 (d, J=5.6 Hz, 2H), 3.30-3.20 (m, 4H), 2.43-2.38 (m, 4H), 2.20 (s, 3H), 1.25 (s, 9H); MS (ES$^+$) m/z Calcd for $C_{30}H_{36}N_8O_3$: 556.29; found: 557.4 (M+H$^+$).

N1-(3-4-[([(5-methyl-3-isoxazolyl)amino]carbonylamino)methyl]phenyl-1H-5-pyrazolyl)-4-(3-tetrahydro-1H-1-pyrrolylpropoxy)benzamide (Compound 55). $^1$H NMR (300 MHz, DMSO-d6): δ 12.83 (bs, 1H), 10.70 (s, 1H), 9.49 (s, 1H), 7.99 (d, J=8.7 Hz, 2H), 7.71 (d, J=8.4 Hz, 2H), 7.34 (d, J=8.4 Hz, 2H), 7.13-6.93 (m, 4H), 6.39 (s, 1H), 4.33 (d, J=5.7 Hz, 2H), 4.07 (t, J=6.5 Hz, 2H), 3.59-3.45 (m, 2H), 2.45-2.41 (m, 4H), 2.31 (s, 3H), 1.95-1.83 (m, 2H), 1.69-1.64 (m, 4H); MS(ES$^+$) m/z calcd, for $C_{29}H_{33}N_7O_4$: 543.26; found: 544.1 (M+H$^+$).

N1-[3-(4-[([5-(tert-butyl)-3-isoxazolyl]aminocarbonyl)amino]methylphenyl)-1H-5-pyrazolyl]-4-(3-tetrahydro-1H-1-pyrrolylpropoxy)benzamide (Compound 56). $^1$H NMR (300 MHz, DMSO-d6): δ 12.86 (s, 1H), 10.68 (s, 1H), 9.48 (s, 1H), 8.01 (d, J=8.7 Hz, 2H), 7.71 (d, J=8.4 Hz, 2H), 7.34 (t, J=7.9 Hz, 2H), 7.18-7.01 (m, 4H), 6.37 (s, 1H), 4.34 (d, J=5.7 Hz, 2H), 4.10 (d, J=6.6 Hz, 2H), 3.33-2.45 (m, 6H, overlapping with solvent peak), 1.95-1.86 (m, 4H), 1.73-1.63 (s, 9H); MS(ES+) m/z calcd. for $C_{32}H_{39}N_7O_4$: 585.31; found: 586.1 (M+H+).

N1-(3-4-[[(5-methyl-3-isoxazolyl)amino]carbonylamino)methyl]phenyl-1H-5-pyrazolyl]-4-(2-tetrahydro-1H-1-pyrrolylethoxy)benzamide (Compound 57). $^1$H NMR (400 MHz, DMSO-d6): δ 12.87 (s, 1H), 10.67 (s, 1H), 9.41 (s, 1H), 8.01 (d, J=8.0 Hz, 2H), 7.71 (d, J=7.2 Hz, 2H), 7.36 (d, J=7.2 Hz, 2H), 7.04-7.01 (m, 4H), 6.40 (s, 1H), 4.34 (d, J=5.2 Hz, 2H), 4.14 (t, J=5.2 Hz, 2H), 2.81 (t, J=5.2 Hz, 2H), 2.60-2.49 (m, 4H, overlapping with solvent peak), 2.32 (s, 3H), 1.70-1.67 (m, 4H); MS (ES+) m/z Calcd for $C_{28}H_{31}N_7O_4$: 529.24; found: 530.3 (M+H+).

N1-[3-(4-[[(5-(tert-butyl)-3-isoxazolyl]aminocarbonyl)amino]methylphenyl)-1H-5-pyrazolyl]-4-(2-tetrahydro-1H-1-pyrrolylethoxy)benzamide (Compound 58). $^1$H NMR (300 MHz, DMSO-d6): δ 12.87 (s, 1H), 10.67 (s, 1H), 9.48 (s, 1H), 8.01 (d, J=8.7 Hz, 2H), 7.72 (d, J=7.8 Hz, 2H), 7.36 (d, J=7.8 Hz, 2H), 7.05-7.01 (m, 4H), 6.38 (s, 1H), 4.34 (d, J=5.4 Hz, 2H), 4.15 (t, J=5.7 Hz, 2H), 2.82 (t, J=5.7 Hz, 2H), 2.62-2.42 (m, 4H, overlapping with solvent peak), 1.78-1.60 (m, 4H), 1.27 (s, 9H); MS (ES+) m/z Calcd for $C_{31}H_{37}N_7O_4$: 571.29; found: 572.3 (M+H+).

N1-(3-4-[[[(5-methyl-3-isoxazolyl)amino]carbonylamino)methyl]phenyl-1H-5-pyrazolyl]-4-(2-morpholinoethoxy)benzamide (Compound 59a). $^1$H NMR (300 MHz, DMSO-d6): δ 10.68 (s, 1H), 9.42 (s, 1H), 8.01 (d, J=8.4 Hz, 2H), 7.72 (d, J=7.8 Hz, 2H), 7.36 (d, J=7.8 Hz, 2H), 7.05-7.02 (m, 4H), 6.41 (s, 1H), 4.35 (d, J=5.4 Hz, 2H), 4.16 (t, J=5.4 Hz, 2H), 3.59 (t, J=4.5 Hz, 4H), 3.38-3.31 (m, 6H), 2.60 (t, J=5.4 Hz, 2H), 2.33 (s, 3H); MS (ES+) m/z Calcd for $C_{28}H_{31}N_7O_5$: 545.24; found: 546.3 (M+H+).

N1-(3-4-[[[(5-ethyl-3-isoxazolyl)amino]carbonylamino)methyl]phenyl-1H-5-pyrazolyl]-4-(2-morpholinoethoxy)benzamide (59b). $^1$H NMR (400 MHz, DMSO-d6): δ 12.86 (s, 1H), 10.66 (s, 1H), 9.43 (s, 1H), 8.00 (d, J=8.0 Hz, 2H), 7.70 (d, J=7.6 Hz, 2H), 7.35 (d, J=7.6 Hz, 2H), 7.01 (d, J=8.8 Hz, 4H), 6.39 (s, 1H), 4.33 (d, J=5.6 Hz, 2H), 4.15 (t, J=4.8 Hz, 2H), 3.56 (t, J=4.0 Hz, 4H), 2.71-2.63 (m, 4H), 2.49-2.46 (m, 4H, overlapping with DMSO peak), 1.17 (t, J=7.6 Hz, 3H); MS (ES+) m/z calcd. for $C_{29}H_{33}N_7O_5$: 559.25; found: 560.3 (M+H+).

N1-(3-4-[[[(5-isopropyl-3-isoxazolyl)amino]carbonylamino)methyl]phenyl-1H-5-pyrazolyl]-4-(2-morpholinoethoxy)benzamide (59c). $^1$H NMR (400 MHz, DMSO-d6): δ 12.87 (s, 1H), 10.67 (s, 1H), 9.46 (s, 1H), 8.00 (d, J=8.8 Hz, 2H), 7.71 (d, J=7.6 Hz, 2H), 7.35 (d, J=8.0 Hz, 2H), 7.03-7.08 (m, 4H), 6.38 (s, 1H), 4.33 (d, J=6.0 Hz, 2H), 4.16 (t, J=5.6 Hz, 2H), 3.57 (t, J=4.8 Hz, 4H), 3.02-2.95 (m, 1H), 2.70 (t, J=5.6 Hz, 2H), 2.49-2.46 (m, 4H, overlapping with DMSO peak), 1.21 (d, J=6.8 Hz, 6H); MS (ES+) m/z calcd. for $C_{30}H_{35}N_7O_5$: 573.27; found: 574.3 (M+H+).

N1-(3-4-[[[(5-cyclopropyl-3-isoxazolyl)amino]carbonylamino)methyl]phenyl-1H-5-pyrazolyl]-4-(2-morpholinoethoxy)benzamide (59d). $^1$H NMR (300 MHz, DMSO-d6): δ 12.88 (s, 1H), 10.68 (s, 1H), 9.43 (s, 1H), 8.02 (d, J=8.7 Hz, 2H), 7.71 (d, J=8.4 Hz, 2H), 7.36 (d, J=8.1 Hz, 2H), 7.05-6.99 (m, 4H), 6.34 (s, 1H), 4.34 (d, J=6.0 Hz, 2H), 4.17 (t, J=5.7 Hz, 2H), 3.59 (t, J=4.8 Hz, 4H), 2.72 (t, J=5.4 Hz, 2H), 2.49-2.46 (m, 4H, overlapping with DMSO peak), 2.09-2.04 (m, 1H), 1.06-0.99 (m, 2H), 0.88-0.84 (m, 2H); MS (ES+) m/z calcd. for $C_{30}H_{33}N_7O_5$: 571.25; found: 572.3 (M+H+).

N1-[3-(4-[[[(5-(tert-butyl)-3-isoxazolyl]aminocarbonyl)amino]methylphenyl)-1H-5-pyrazolyl]-4-(2-morpholinoethoxy)benzamide (Compound 60). $^1$H NMR (400 MHz, DMSO-d6): δ 12.87 (s, 1H), 10.68 (s, 1H), 9.48 (s, 1H), 8.00 (d, J=8.0 Hz, 2H), 7.71 (d, J=7.2 Hz, 2H), 7.35 (d, J=7.6 Hz, 2H), 7.03 (d, J=8.0 Hz, 2H), 7.00 (s, 1H), 6.38 (s, 1H), 4.33 (t, J=5.2 Hz, 2H), 4.16 (t, J=5.6 Hz, 2H), 3.57 (t, J=4.4 Hz, 4H), 2.70 (t, J=5.2 Hz, 2H), 2.49-2.47 (m, 4H, overlapped with DMSO), 1.27 (s, 9H); MS (ES+) m/z calcd. for $C_{31}H_{37}N_7O_5$: 587.28; found: 588.3 (M+H+).

N1-[3-(4-[(anilinocarbonyl)amino]methylphenyl)-1H-5-pyrazolyl]-4-(2-morpholinoethoxy)benzamide (Compound 61a). $^1$H NMR (300 MHz, DMSO-d6): δ 10.71 (s, 1H), 8.56 (s, 1H), 8.01 (d, J=8.7 Hz, 2H), 7.71 (d, J=7.8 Hz, 2H), 7.42-7.37 (m, 4H), 7.22 (t, J=7.8 Hz, 2H), 7.04-7.02 (m, 3H), 6.90 (t, J=7.2 Hz, 1H), 6.65 (t, J=5.7 Hz, 1H), 4.32 (d, J=5.7 Hz, 2H), 4.17 (t, J=5.7 Hz, 2H), 3.58 (t, J=4.8 Hz, 4H), 3.38-3.23 (m, 4H), 2.71 (t, J=5.7 Hz, 2H); MS(ES+) m/z Calcd for $C_{30}H_{32}N_6O_4$: 540.25; found: 541.3 (M+H+).

N1-3-[4-([(4-fluoroanilino)carbonyl]aminomethyl)phenyl]-1H-5-pyrazolyl-4-(2-morpholinoethoxy)benzamide (61b). $^1$H NMR (300 MHz, DMSO-d6): δ 12.87 (s, 1H), 10.67 (s, 1H), 8.63 (s, 1H), 8.00 (d, J=8.7 Hz, 2H), 7.71 (d, J=8.1 Hz, 2H), 7.44-7.35 (m, 4H), 7.10-7.02 (m, 4H), 6.65 (t, J=6.0 Hz, 1H), 4.32 (d, J=6.0 Hz, 2H), 4.17 (t, J=5.7 Hz, 2H), 3.58 (t, J=4.8 Hz, 4H), 2.71 (t, J=5.7 Hz, 2H), 2.50-2.46 (m, 4H, overlapping with DMSO peak); MS (ES+) m/z calcd. for $C_{30}H_{31}FN_6O_4$: 558.24; found: 559.2 (M+H+).

N1-3-[4-([(4-chloroanilino)carbonyl]aminomethyl)phenyl]-1H-5-pyrazolyl-4-(2-morpholinoethoxy)benzamide (61c). $^1$H NMR (400 MHz, DMSO-d6): δ 12.87 (s, 1H), 10.68 (s, 1H), 8.76 (s, 1H), 8.01 (d, J=8.8 Hz, 2H), 7.72 (d, J=8.0 Hz, 2H), 7.45 (d, J=8.4 Hz, 2H), 7.37 (d, J=7.6 Hz, 2H), 7.27 (d, J=8.4 Hz, 2H), 7.04 (d, J=8.0 Hz, 2H), 6.72 (t, J=5.6 Hz, 1H), 4.32 (d, J=6.0 Hz, 2H), 4.17 (t, J=5.6 Hz, 2H), 3.58 (t, J=4.8 Hz, 4H), 2.71 (t, J=5.6 Hz, 2H), 2.50-2.48 (m, 4H, overlapping with DMSO peak); MS (ES+) m/z calcd. for $C_{30}H_{31}ClN_6O_4$: 574.21; found: 575.2 (M+H+).

N1-(3-4-[[[(5-methyl-3-isoxazolyl)amino]carbonylamino)methyl]phenyl-1H-5-pyrazolyl]-4-[(4-methylpiperazino)methyl]benzamide (Compound 62a). $^1$H NMR (400 MHz, DMSO-d6): δ 12.93 (s, 1H), 10.83 (s, 1H), 9.46 (s, 1H), 7.97 (d, J=8.4 Hz, 2H), 7.72 (d, J=8.4 Hz, 2H), 7.41 (d, J=8.0 Hz, 2H), 7.35 (d, J=8.0 Hz, 2H), 7.04 (d, J=5.8 Hz, 2H), 6.41 (s, 1H), 4.34 (d, J=5.6 Hz, 2H), 3.51 (s, 2H), 2.49-2.28 (m, 8H, overlapping with solvent peak), 2.14 (s, 6H); MS (ES+) m/z calcd, for $C_{28}H_{32}N_8O_3$: 528.26; found: 529.3 (M+H+).

N1-(3-4-[[[(5-ethyl-3-isoxazolyl)amino]carbonylamino)methyl]phenyl-1H-5-pyrazolyl]-4-[(4-methylpiperazino)methyl]benzamide (62b). $^1$H NMR (400 MHz, DMSO-d6): δ 12.91 (s, 1H), 10.79 (s, 1H), 9.45 (s, 1H), 7.98 (d, J=7.6 Hz, 2H), 7.72 (d, J=8.4 Hz, 2H), 7.38 (dd, J=16.4, 8.0 Hz, 4H), 7.03 (s, 2H), 6.41 (s, 1H), 4.35 (d, J=5.6 Hz, 2H), 3.50 (s, 2H), 3.34-3.31 (m, 4H, overlapping with water peak), 2.68 (q, J=7.6 Hz, 2H), 2.35-2.31 (m, 4H), 2.13 (s, 3H), 1.17 (t, J=7.6 Hz, 3H); MS (ES+) m/z calcd. for $C_{29}H_{34}N_8O_3$: 542.28; found: 543.3 (M+H+).

N1-(3-4-[[[(5-isopropyl-3-isoxazolyl)amino]carbonylamino)methyl]phenyl-1H-5-pyrazolyl]-4-[(4-methylpiperazino)methyl]benzamide (62c). $^1$H NMR (400 MHz, DMSO-d6): δ 12.91 (s, 1H), 10.80 (s, 1H), 9.48 (s, 1H), 7.98 (d, J=8.0 Hz, 2H), 7.72 (d, J=8.0 Hz, 2H), 7.39 (dd, J=19.2, 8.0 Hz, 4H), 7.04 (s, 2H), 6.39 (s, 1H), 4.35 (d, J=6.0 Hz, 2H), 3.52 (s, 2H), 3.03-2.96 (m, 1H), 2.38 (br s, 8H), 2.17 (s, 3H), 1.22 (d, J=6.8 Hz, 6H); MS (ES+) m/z calcd. for $C_{30}H_{36}N_8O_3$: 556.29; found: 557.3 (M+H+).

N1-(3-4-[[[(5-cyclopropyl-3-isoxazolyl)amino]carbonylamino)methyl]phenyl-1H-5-pyrazolyl]-4-[(4-methylpiperazino)methyl]benzamide (62d). $^1$H NMR (400 MHz, DMSO-d6): δ 12.91 (s, 1H), 10.80 (s, 1H), 9.42 (s, 1H), 7.98 (d, J=8.0 Hz, 2H), 7.72 (d, J=7.6 Hz, 2H), 7.38 (dd, J=18.8, 8.0 Hz, 4H), 7.03-6.99 (m, 2H), 6.34 (s, 1H), 4.34 (d, J=6.0 Hz, 2H), 3.52 (s, 2H), 2.37 (br s, 8H), 2.15 (s, 3H), 2.10-2.05 (m, 1H), 1.04-0.99 (m, 2H), 0.87-0.83 (m, 2H); MS (ES+) m/z calcd. for $C_{30}H_{34}N_8O_3$: 554.28; found: 555.3 (M+H+).

N1-[3-(4-[([5-(tert-butyl)-3-isoxazolyl]aminocarbonyl)amino]methylphenyl)-1H-5-pyrazolyl]-4-[(4-methylpiperazino)methyl]benzamide (Compound 63). $^1$H NMR (300 MHz, DMSO-d6): δ 10.82 (s, 1H), 10.71 (s, 1H), 9.50 (s, 1H), 7.98 (d, J=8.1 Hz, 2H), 7.72 (d, J=8.1 Hz, 2H), 7.41 (d, J=8.1 Hz, 2H), 7.36 (t, J=8.4 Hz, 2H), 7.02 (t, J=5.7 Hz, 2H), 6.38 (s, 1H), 4.35 (d, J=5.7 Hz, 2H), 3.52 (s, 2H), 3.25 (s, 4H), 2.37 (s, 4H), 2.15 (s, 3H), 1.27 (s, 9H); MS (ES+) m/z Calcd for $C_{31}H_{38}N_8O_3$: 570.31; found: 571.4 (M+H+).

N1-(3-4-[([(5-methyl-1,3-thiazol-2-yl)amino]carbonylamino)methyl]phenyl-1H-5-pyrazolyl)-4-(4-methylpiperazino)benzamide (Compound 64). $^1$H NMR (400 MHz, DMSO-d6): δ 12.85 (s, 1H), 10.54 (s, 1H), 10.33 (s, 1H), 8.12 (d, J=9.2 Hz, 2H), 7.93 (d, J=8.0 Hz, 2H), 7.36 (d, J=8.4 Hz, 2H), 7.07 (s, 1H), 6.99-6.96 (m, 4H), 4.35 (d, J=6.0 Hz, 2H), 3.29-3.27 (m, 4H), 2.46-2.44 (m, 4H), 2.31 (s, 3H), 2.23 (s, 3H); MS(ES+) m/z calcd, for $C_{27}H_{30}N_8O_2S$: 530.22; found: 531.2 (M+H+).

N1-3-[4-([(2-pyridylamino)carbonyl]aminomethyl)phenyl]-1H-5-pyrazolyl-4-(4-methylpiperazino)benzamide (Compound 65). $^1$H NMR (400 MHz, DMSO-d6): δ 12.85 (s, 1H), 10.54 (s, 1H), 9.34 (s, 1H), 8.69 (s, 1H), 8.18-8.17 (m, 1H), 7.93 (d, J=8.8 Hz, 2H), 7.73-7.66 (m, 3H), 7.39-7.36 (m, 3H), 6.98 (d, J=8.4 Hz, 2H), 6.94-6.91 (m, 2H), 4.43 (d, J=4.5 Hz, 2H), 3.29-3.27 (m, 4H), 2.45-2.43 (m, 4H), 2.22 (s, 3H); MS(ES+) m/z calcd, for $C_{28}H_{30}N_8O_2$: 510.25; found: 511.4 (M+H+).

N1-3-[4-([(propylamino)carbonyl]aminomethyl)phenyl]-1H-5-pyrazolyl-4-(2-morpholinoethoxy)benzamide (Compound 66). $^1$H NMR (400 MHz, DMSO-d6): δ 12.65 (s, 1H), 10.46 (s, 1H), 7.80 (d, J=8.6 Hz, 2H), 7.47 (d, J=7.4 Hz, 2H), 7.10 (d, J=7.4 Hz, 2H), 6.82 (d, J=8.6 Hz, 2H), 6.79 (s, 1H), 6.11 (s, 1H), 5.74 (s, 1H), 4.01 (d, J=5.2 Hz, 2H), 3.95 (s, 2H), 3.12 (s, 4H), 2.80-2.73 (m, 2H), 2.30-2.25 (m, 6H), 1.18 (qd, J=7.2, 7.2 Hz, 2H), 0.63 (t, J=7.2 Hz, 3H); MS (ES+) m/z Calcd for $C_{27}H_{34}N_6O_4$: 506.26; found: 507.3 (M+H+).

Example 5

Synthesis of Compounds 67-84

Compounds 67-84 were prepared following the synthetic route shown in the scheme below:

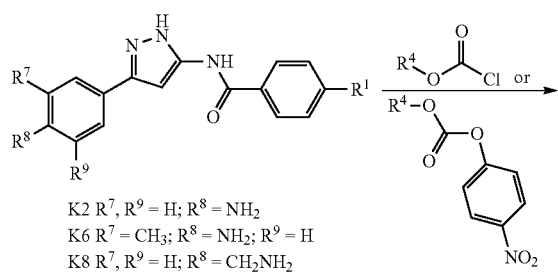

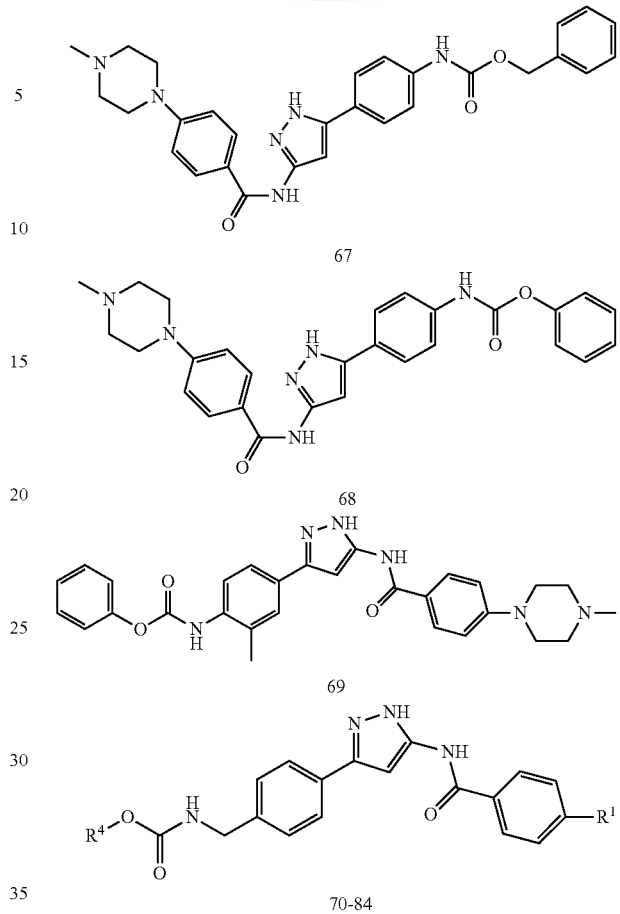

To a solution of K2, K6 or K8 (1.0 equiv) and pyridine (5.0 equiv) in DMSO at room temperature or 70° C. was added chloroformate R4—OCOCl (1.2 equiv) or 4-nitrophenyl carbonate R4OCO2(4-NO2-Ph) (1.5 equiv). After 0.5 h of stirring at room temperature, the reaction was worked up as described for compounds J to yield Compounds 67-84.

Benzyl-N-[4-(5-[4-(4-methylpiperazino)benzoyl]amino-1H-3-pyrazolyl)phenyl]carbamate (Compound 67). $^1$H NMR (400 MHz, DMSO-d6): δ 12.74 (s, 1H), 10.48 (s, 1H), 9.93 (s, 1H), 7.93 (d, J=8.4 Hz, 2H), 7.67 (d, J=8.4 Hz, 2H), 7.54 (d, t, J=8.4 Hz, 2H), 7.47-7.31 (m, 5H), 6.98-6.96 (m, 3H), 5.17 (s, 2H), 3.29-3.27 (m, 4H), 2.45-2.42 (m, 4H), 2.22 (s, 3H); MS(ES+) m/z calcd, for $C_{29}H_{30}N_6O_3$: 510.24; found: 511.1 (M+H+).

Phenyl-N-[4-(5-[4-(4-methylpiperazino)benzoyl]amino-1H-3-pyrazolyl)phenyl]carbamate (Compound 68). $^1$H NMR (400 MHz, DMSO-d6): δ 12.77 (s, 1H), 10.49 (s, 1H), 10.38 (s, 1H), 7.93 (d, J=8.8 Hz, 2H), 7.72 (d, J=8.4 Hz, 2H), 7.58 (d, J=8.4 Hz, 2H), 7.47-7.42 (m, 2H), 7.29-7.24 (m, 3H), 6.98-6.97 (m, 3H), 3.28 (bs, 4H), 2.45-2.43 (m, 4H), 2.22 (s, 3H); MS(ES+) m/z calcd, for $C_{28}H_{28}N_6O_3$: 496.22; found: 497.1 (M+H+).

Phenyl-N[2-methyl-4-(5-[4-(4-methylpiperazino)benzoyl]amino-1H-3-pyrazolyl)phenyl]carbamate (Compound 69). $^1$H NMR (300 MHz, DMSO-d6): δ 10.51 (s, 1H), 9.55 (s, 1H), 7.93 (d, J=8.7 Hz, 2H), 7.76 (s, 1H), 7.56 (t, J=8.1 Hz, 2H), 7.43 (t, J=8.1 Hz, 2H), 7.28-7.22 (m, 3H), 6.98 (d, J=9.9 Hz, 4H), 3.29 (t, J=4.8 Hz, 4H), 2.44 (t, J=4.8 Hz, 4H), 2.35 (s, 3H), 2.22 (s, 3H); MS (ES+) m/z Calcd for $C_{29}H_{30}N_6O_3$: 510.24; found: 511.3 (M+H+).

Benzyl-N-[4-(5-[4-(4-methylpiperazino)benzoyl]amino-1H-3-pyrazolyl)benzyl]carbamate (Compound 70). $^1$H NMR (300 MHz, DMSO-d6): δ 10.75 (br s, 1H), 10.65 (s, 1H), 7.99 (d, J=8.4 Hz, 2H), 7.88 (t, J=6.0 Hz, 1H), 7.71 (d, J=7.8 Hz, 2H), 7.38-7.31 (m, 6H), 7.08 (d, J=8.7 Hz, 2H), 6.96 (br s, 1H), 5.06 (s, 1H), 4.23 (d, J=6.0 Hz, 2H), 4.02 (br s, 2H), 3.47 (br s, 4H), 2.82 (s, 3H), 2.51-2.49 (m, 4H, overlapping with DMSO); MS (ES$^+$) m/z Calcd for $C_{30}H_{32}N_6O_3$: 524.25; found: 525.4 (M+H$^+$).

Benzyl-N-[4-(5-[4-(2-morpholinoethoxy)benzoyl]amino-1H-3-pyrazolyl)benzyl]carbamate (Compound 71). $^1$H NMR (400 MHz, DMSO-d6): δ 10.80 (s, 1H), 8.06 (m, 3H), 7.88 (t, J=6.4 Hz, 1H), 7.71 (d, J=8.4 Hz, 2H), 7.40-7.35 (m, 5H), 7.33 (d, J=8.4 Hz, 2H), 7.11 (d, J=8.4 Hz, 2H), 6.95 (s, 1H), 5.06 (s, 2H), 4.53 (t, J=4.4 Hz, 2H), 4.23 (d, J=6.0 Hz, 2H), 3.97 (d, J=11.6 Hz, 2H), 3.84 (t, J=11.6 Hz, 2H), 3.58 (t, J=4.4 Hz, 2H), 3.59 (d, J=11.6 Hz, 2H), 3.21 (t, J=4.4 Hz, 2H); MS (ES$^+$) m/z Calcd for $C_{31}H_{33}N_5O_5$: 555.25; found: 556.1 (M+H$^+$).

Benzyl-N-[4-(5-[4-(3-tetrahdro-1H-1-pyrrolylpropoxy)benzoyl]amino-1H-3-pyrazolyl)benzyl]carbamate (Compound 72). $^1$H NMR (400 MHz, DMSO-d6): δ 12.91 (s, 1H), 10.73 (s, 1H), 8.03 (d, J=8.8 Hz, 2H), 7.88 (t, J=6.2 Hz, 1H), 7.71 (d, J=8.4 Hz, 2H), 7.39-7.29 (m, 7H), 7.05-6.95 (m, 3H), 5.06 (s, 2H), 4.23 (d, J=6.0 Hz, 2H), 4.13 (t, J=6.0 Hz, 2H), 3.11-2.84 (m, 6H), 2.10-2.04 (m, 2H), 1.84 (s, 4H); MS(ES$^+$) m/z calcd, for $C_{32}H_{35}N_5O_4$: 553.27; found: 554.2 (M+H$^+$).

Benzyl-N-[4-(5-[4-(2-tetrahydro-1H-1-pyrrolylethoxy)benzoyl]amino-1H-3-pyrazolyl)benzyl]carbamate (Compound 73). $^1$H NMR (400 MHz, DMSO-d6): δ 12.86 (s, 1H), 10.66 (s, 1H), 8.00 (d, J=8.4 Hz, 2H), 7.87 (t, J=6.0 Hz, 1H), 7.68 (d, J=7.2 Hz, 2H), 7.39-7.34 (m, 5H), 7.31 (d, J=7.2 Hz, 2H), 7.06-6.98 (m, 3H), 5.04 (s, 2H), 4.22 (d, J=6.0 Hz, 2H), 4.13 (t, J=5.6 Hz, 2H), 2.79 (t, J=5.6 Hz, 2H), 2.56-2.46 (m, 4H, overlapping with solvent peak), 1.74-1.62 (m, 4H); MS (ES$^+$) m/z Calcd for $C_{31}H_{33}N_5O_4$: 539.25; found: 540.3 (M+H$^+$).

(5-Methyl-3-isoxazolyl)methyl-N-[4-(5-[4-(2-morpholinoethoxy)benzoyl]amino-1H-3-pyrazolyl)benzyl]carbamate (Compound 74). $^1$H NMR (300 MHz, DMSO-d6): 12.87 (s, 1H), 10.68 (s, 1H), 8.02-7.94 (m, 3H), 7.71 (d, J=8.1 Hz, 2H), 7.33 (d, J=7.5 Hz, 2H), 7.04 (d, J=8.1 Hz, 3H), 6.21 (s, 1H), 5.06 (s, 2H), 4.23 (d, J=5.7 Hz, 2H), 4.17 (t, J=5.7 Hz, 2H), 3.58 (t, J=4.5 Hz, 4H), 2.71 (t, J=5.7 Hz, 2H), 2.49-2.39 (m, 4H, overlapping with DMSO), 2.34 (s, 3H); MS (ES$^+$) m/z calcd. for $C_{29}H_{32}N_6O_6$: 560.24; found: 583.2 (M+Na), 561.2 (M+H$^+$).

(5-Methyl-3-isoxazolyl)methyl-N-[4-(5-[4-(4-methylpiperazino)benzoyl]amino-1H-3-pyrazolyl)benzyl]carbamate (Compound 75). $^1$H NMR (300 MHz, DMSO-d6): δ 10.51 (s, 1H), 7.97-7.92 (m, 3H), 7.70 (d, J=7.2 Hz, 2H), 7.33 (d, J=7.8 Hz, 2H), 7.00-6.97 (m, 3H), 6.22 (s, 1H), 5.06 (s, 2H), 4.23 (d, J=5.7 Hz, 2H), 3.29 (t, J=4.8 Hz, 4H), 2.44 (t, J=4.8 Hz, 4H), 2.40 (s, 3H), 2.23 (s, 3H); MS (ES$^+$) m/z Calcd for $C_{28}H_{31}N_7O_4$: 529.24; found: 530.3 (M+H$^+$).

(5-Methyl-3-isoxazolyl)methyl-N-[4-(5-[4-(2-tetrahydro-1H-1-pyrrolylethoxy)benzoyl]amino-1H-3-pyrazolyl)benzyl]carbamate (Compound 76). $^1$H NMR (400 MHz, DMSO-d6): δ 12.87 (s, 1H), 10.66 (s, 1H), 8.06-7.90 (m, 3H), 7.69 (d, J=7.6 Hz, 2H), 7.31 (d, J=7.6 Hz, 2H), 7.10-6.92 (m, 3H), 6.20 (s, 1H), 5.04 (s, 2H), 4.21 (d, J=6.0 Hz, 2H), 4.13 (t, J=6.0 Hz, 2H), 2.79 (t, J=6.0 Hz, 2H), 2.52-2.44 (m, 4H, overlapping with solvent peak), 2.38 (s, 3H), 1.74-1.62 (m, 4H); MS (ES$^+$) m/z Calcd for $C_{29}H_{32}N_6O_5$: 544.24; found: 545.3 (M+H$^+$).

Benzyl-N-4-[5-(4-[(4-methylpiperazino)methyl]benzoylamino)-1H-3-pyrazolyl]benzylcarbamate (Compound 77). $^1$H NMR (300 MHz, DMSO-d6): δ 12.91 (s, 1H), 10.82 (s, 1H), 7.98 (d, J=8.1 Hz, 2H), 7.88 (s, 1H), 7.71 (d, J=7.8 Hz, 2H), 7.43-7.31 (m, 9H), 7.03 (s, 1H), 5.06 (s, 2H), 4.23 (d, J=6.3 Hz, 2H), 3.54 (d, J=10.5 Hz, 2H), 2.49-2.38 (m, 8H), 2.17 (s, 3H); MS(ES$^+$) m/z calcd, for $C_{31}H_{34}N_6O_3$: 538.27; found: 539.1 (M+H$^+$).

3-Pyridylmethyl-N-[4-(5-[4-(2-tetrahydro-1H-1-pyrrolylethoxy)benzoyl]amino-1H-3-pyrazolyl)benzyl]carbamate (Compound 78). $^1$H NMR (400 MHz, DMSO-d6): δ 12.85 (s, 1H), 10.67 (s, 1H), 8.55 (s, 1H), 8.49 (d, J=3.6 Hz, 1H), 7.96 (d, J=8.4 Hz, 2H), 7.89 (t, J=6.0 Hz, 1H), 7.74 (d, J=7.6 Hz, 1H), 7.66 (d, J=8.0 Hz, 2H), 7.38-7.35 (m, 1H), 7.27 (d, J=8.0 Hz, 2H), 6.99 (d, J=8.8 Hz, 2H), 5.05 (s, 2H), 4.18 (d, J=6.0 Hz, 2H), 4.10 (t, J=6.0 Hz, 2H), 2.78 (t, J=6.0 Hz, 2H), 2.50-2.45 (m, 4H, overlapped with DMSO), 1.64 (br s, 4H); MS (ES$^+$) m/z calcd. for $C_{30}H_{32}N_6O_4$: 540.24; found: 541.3 (M+H$^+$).

3-Pyridylmethyl-N-[4-(5-[4-(4-methylpiperazino)benzoyl]amino-1H-3-pyrazolyl)benzyl]carbamate (Compound 79). $^1$H NMR (400 MHz, DMSO-d6): δ 12.90 (s, 1H), 10.82 (s, 1H), 8.66 (s, 1H), 8.59 (d, J=4.4 Hz, 2H), 8.00-7.98 (m, 3H), 7.85 (d, J=7.2 Hz, 1H), 7.75 (d, J=7.6 Hz, 2H), 7.47 (dd, J=4.4, 8.0 Hz, 1H), 7.38 (d, J=8.0 Hz, 2H), 7.06-7.03 (m, 3H), 5.10 (s, 2H), 4.23 (d, J=6.0 Hz, 2H), 3.28 (t, J=4.4 Hz, 4H), 2.44 (t, J=4.4 Hz, 4H), 2.22 (s, 3H); MS (ES$^+$) m/z Calcd for $C_{29}H_{31}N_7O_3$: 525.25; found: 526.2 (M+H$^+$).

3-Pyridylmethyl-N-[4-(5-[4-(2-morpholinoethoxy)benzoyl]amino-1H-3-pyrazolyl)benzyl]carbamate (Compound 80). $^1$H NMR (400 MHz, DMSO-d6): δ 12.83 (s, 1H), 10.71 (s, 1H), 8.59 (s, 1H), 8.53 (d, J=4.4 Hz, 1H), 8.00 (d, J=8.8 Hz, 2H), 7.92-7.86 (m, 1H), 7.78 (d, J=8.0 Hz, 1H), 7.69 (d, J=8.4 Hz, 2H), 7.42-7.39 (m, 1H), 7.31 (d, J=8.0 Hz, 2H), 7.03 (d, J=8.8 Hz, 2H), 6.94 (br s, 1H), 5.09 (s, 2H), 4.22 (d, J=6.4 Hz, 2H), 4.16 (t, J=5.6 Hz, 2H), 3.57 (t, J=4.8 Hz, 4H), 2.70 (t, J=5.6 Hz, 2H), 2.53-2.46 (m, 4H, overlapped with DMSO); MS (ES$^+$) m/z calcd. for $C_{30}H_{32}N_6O_5$: 556.24; found: 557.2 (M+H$^+$).

Ethyl-N-[4-(5-[4-(4-methylpiperazino)benzoyl]amino-1H-3-pyrazolyl)benzyl]carbamate (Compound 81). $^1$H NMR (400 MHz, DMSO-d6): δ 12.84 (s, 1H), 10.54 (s, 1H), 7.92 (d, J=8.8 Hz, 2H), 7.71-7.67 (m, 2H), 7.31 (d, J=8.0 Hz, 2H), 6.99-6.97 (m, 3H), 4.19 (d, J=6.0 Hz, 2H), 4.01 (q, J=7.2 Hz, 2H), 3.29-3.27 (m, 4H), 2.45-2.43 (m, 4H), 2.22 (s, 3H), 1.17 (t, J=7.2 Hz, 3H); MS(ES$^+$) m/z calcd, for $C_{25}H_{30}N_6O_3$: 462.24; found: 463.3 (M+H$^+$).

Phenyl-N-[4-(5-[4-(4-methylpiperazino)benzoyl]amino-1H-3-pyrazolyl)benzyl]carbamate (Compound 82). $^1$H NMR (400 MHz, DMSO-d6): δ 12.86 (s, 1H), 10.52 (s, 1H), 8.35 (t, J=6.4 Hz, 2H), 7.93 (d, J=8.8 Hz, 2H), 7.74 (d, J=8.0 Hz, 2H), 7.38 (m, 4H), 7.21 (t, J=7.6 Hz, 1H), 7.13 (d, J=7.6 Hz, 2H), 7.02-6.97 (m, 3H), 4.30 (d, J=6.0 Hz, 2H), 3.33-3.29 (m, 4H), 2.46-2.43 (m, 4H), 2.22 (s, 3H); MS(ES$^+$) m/z calcd, for $C_{29}H_{30}N_6O_3$: 510.24; found: 511.2 (M+H$^+$).

Phenyl-N-[4-(5-[4-(2-tetrahydro-1H-1-pyrrolylethoxy)benzoyl]amino-1H-3-pyrazolyl)phenyl]carbamate (Compound 83). $^1$H NMR (400 MHz, DMSO-d6): δ 12.78 (s, 1H), 10.71 (s, 1H), 10.40 (s, 1H), 8.02 (d, J=8.4 Hz, 2H), 7.72 (d, J=8.4 Hz, 2H), 7.58 (d, J=8.4 Hz, 2H), 7.45 (t, J=8.0 Hz, 2H), 7.30-7.24 (m, 3H), 7.04 (d, J=8.4 Hz, 2H), 6.94 (s, 1H), 4.18 (t, J=5.6 Hz, 2H), 2.90 (t, J=5.6 Hz, 2H), 2.62 (s, 4H), 1.72 (s, 4H); MS (ES$^+$) m/z Calcd for $C_{29}H_{29}N_5O_4$: 511.22; found: 512.2 (M+H$^+$).

Phenyl N-[4-(5-[4-(2-morpholinoethoxy)benzoyl]amino-1H-3-pyrazolyl)benzyl]carbamate (Compound 84). $^1$H NMR (400 MHz, DMSO-d6): δ 12.90 (s, 1H), 10.69 (s, 1H), 8.35 (t, J=6.0 Hz, 1H), 8.02 (d, J=8.4 Hz, 2H), 7.74 (d, J=8.0 Hz, 2H), 7.48-7.32 (m, 4H), 7.21 (t, J=7.2 Hz, 1H), 7.14 (d, J=8.4 Hz, 2H), 7.10-6.98 (m, 3H), 4.31 (d, J=6.0 Hz, 2H), 4.17 (t, J=5.6 Hz, 2H), 3.58 (t, J=4.6 Hz, 4H), 2.71 (t, J=6.0 Hz, 2H), 2.58-2.46 (m, 4H, overlapping with solvent peak); MS (ES+) m/z Calcd for $C_{30}H_{31}N_5O_5$: 541.23; found: 542.2 (M+H+).
Example 6
Synthesis of Compounds 85-119
Below is a general synthetic scheme for the synthesis of Compounds 85-119:
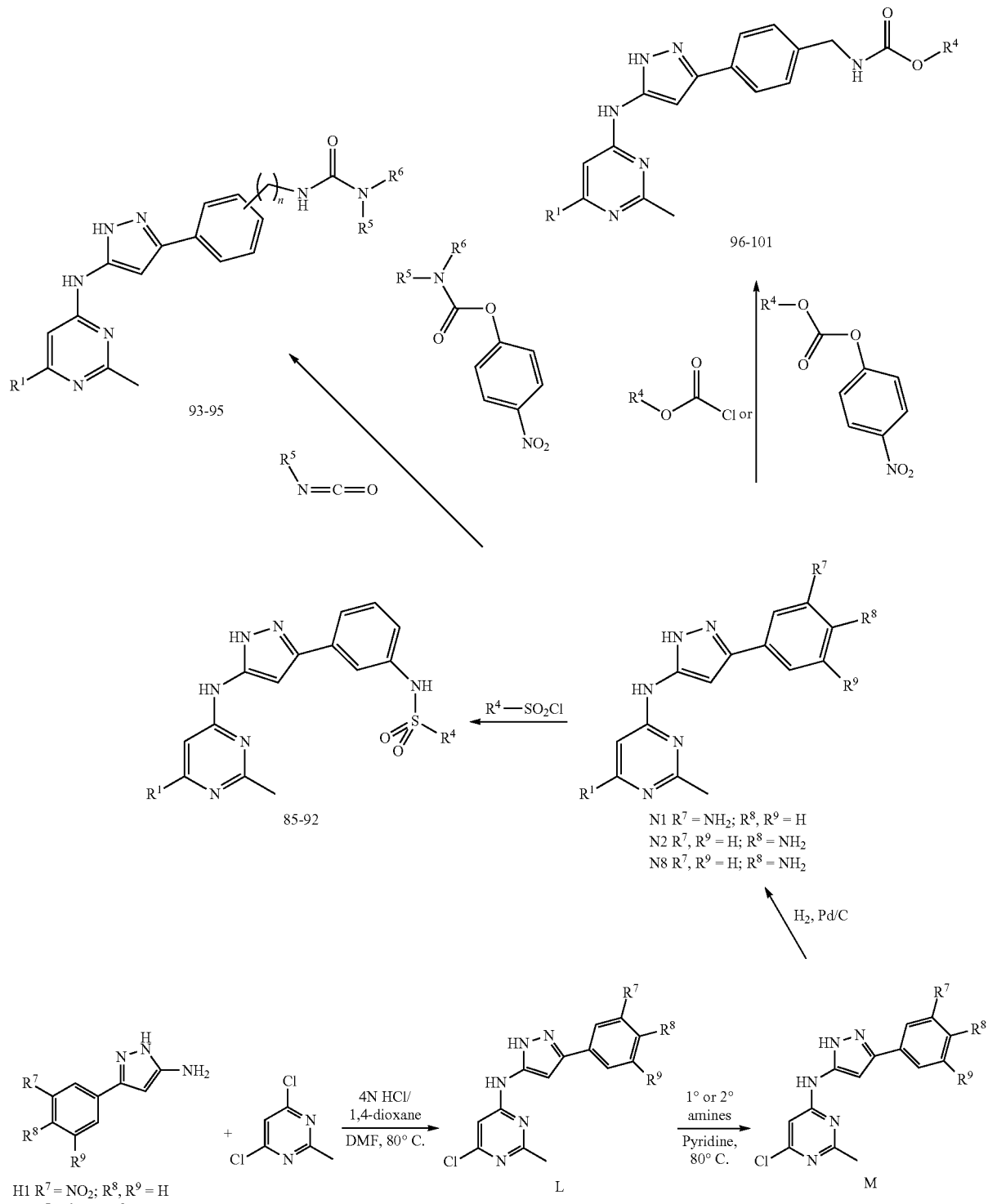

-continued

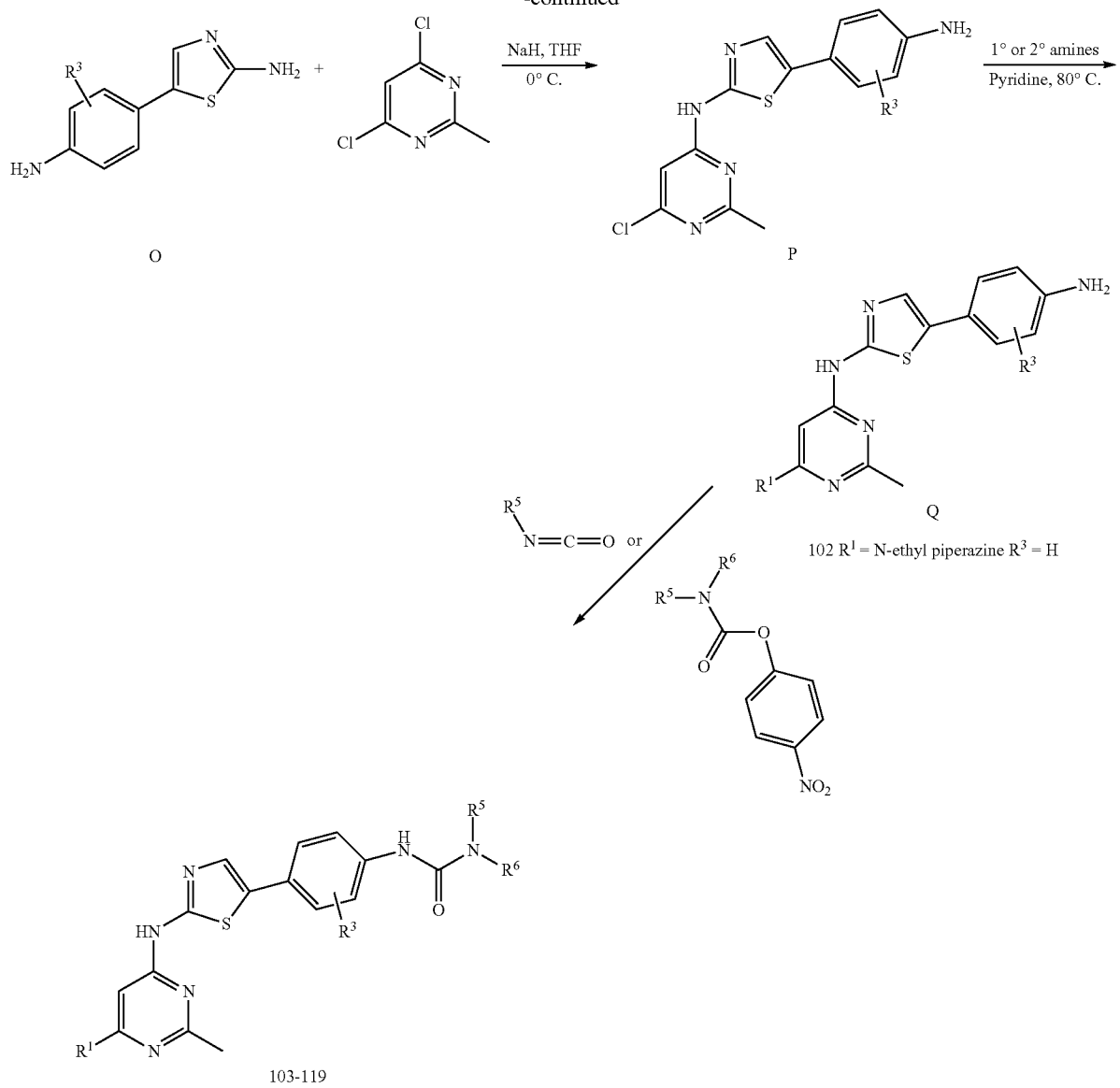

Note: Compound O was synthesized following the procedure described in *Tetrahedron Letter* 2000, 41, 3883-3886.

Step I. Synthesis of Compounds L:

To a solution of H1, H2 or H8 (1.0 equiv) and 4,6-dichloro-2-methylpyrimidine (1.5 equiv) in DMF at room temperature was added hydrogen chloride solution (4.0 M in dioxane, 1.6 equiv) and the resultant mixture was stirred at 80° C. for 4 h. After cooling to room temperature, the solvent was evaporated in vacuo to give a viscous residue, which was partitioned between EtOAc and 1 N NaHCO$_3$. The organic layer was separated, dried over MgSO$_4$ and concentrated in vacuo. Purification by flash column chromatography (eluted with CH$_2$Cl$_2$/CH$_3$OH) yielded compounds L. Only one of L is selected to show its NMR spectrum and Mass.

N-(6-chloro-2-methyl-4-pyrimidinyl)-N-[5-(3-nitrophenyl)-1H-3-pyrazolyl]amine. $^1$H NMR (400 MHz, DMSO-d6): δ 13.21 (s, 1H), 10.34(s, 1H) 10.34 (s, 1H), 8.58 (s, 1H), 8.18 (d, J=7.2 Hz, 2H), 7.74 (t, J=8.0 Hz, 1H), 6.85 (br s, 1H), 2.46 (s, 3H); MS (ES$^+$) m/z calcd. for C$_{14}$H$_{11}$ClN$_6$O$_2$: 330.06; found: 331.1 (M+H$^+$).

Step II. Synthesis of Compounds P:

A suspension of NaH (60% in oil, 2.1 equiv) in THF was cooled in an ice-water bath. To this solution was added O (1.0 equiv) and the reaction stirred at 0° C. for 0.5 h. To this white suspension was added 4,6-dichloro-2-methylpyrimidine (1.1 equiv) and the reaction stirred at 0° C. for 1 h. The reaction was quenched with ice water and partitioned between CH$_2$Cl$_2$ and 1 N NaHCO$_3$. The organic layer was separated, dried over MgSO$_4$ and concentrated in vacuo. Purification by flash column chromatography (eluted with CH$_2$Cl$_2$/CH$_3$OH) yielded compounds P. Only one of P is selected to show its NMR spectrum and Mass.

N2-(6-chloro-2-methyl-4-pyrimidinyl)-5-(4-aminophenyl)-1,3-thiazol-2-amine. $^1$H NMR (300 MHz, DMSO-d6): δ 11.77 (s, 1H), 7.54 (s, 1H), 7.28-7.24 (m, 2H), 6.89 (s, 1H), 6.59-6.56 (m, 2H), 5.31 (s, 2H), 2.55 (s, 3H); MS (ES$^+$) m/z calcd. for C$_{14}$H$_{12}$ClN$_5$S: 317.05; found: 318.1 (M+H$^+$).

Step III. Synthesis of Compounds M and Q:

To a solution of L or P (1.0 equiv) in pyridene at room temperature was added 1° or 2° amines (2.0 equiv) and the resultant mixture was stirred at 80° C. for 2 h. After cooling to room temperature, the reaction was worked up as described for the synthesis of compounds J to yield compounds M or Q, respectively, which were used without further purification or Q was purified to get compound 102.

Step IV. Synthesis of Compounds N:

Starting with M, the same procedures were followed as described in the synthesis of K to yield compounds N without further purification.

Step V. Synthesis of Compounds 85-119:

Starting with N, the same procedures were followed as described in the synthesis of Compounds 12-28 to yield Compounds 85-92, as described in the synthesis of Compounds 29-66 to yield Compounds 93-95, and as described in the synthesis of Compounds 67-84 to yield Compounds 96-101. Compounds 103-119 were synthesized from Q and followed the same procedures as described in the synthesis of Compounds 29-66.

N1-[3-(5-[2-methyl-6-(4-methylpiperazino)-4-pyrimidinyl]amino-1H-3-pyrazolyl)phenyl]-1-benzenesulfonamide (Compound 85). $^1$H NMR (400 MHz, DMSO-d6): δ 12.72 (s, 1H), 10.41 (s, 1H), 9.35 (s, 1H), 7.81-7.78 (m, 2H), 7.63-7.53 (m, 3H), 7.38-7.26 (m, 3H), 7.04 (d, J=7.6 Hz, 1H), 6.66 (s, 1H), 6.36 (s, 1H), 3.49 (t, J=4.4 Hz, 4H), 2.38 (t, J=4.4 Hz, 4H), 2.30 (s, 3H), 2.22 (s, 3H); MS (ES$^+$) m/z calcd. for $C_{25}H_{28}N_8O_2S$: 504.61; found: 505.1 (M+H$^+$); HRMS (FAB) calcd. for $C_{25}H_{28}N_8O_2S$: 504.2056; found: 504.2066.

N1-[3-(5-[2-methyl-6-(4-methylpiperazino)-4-pyrimidinyl]amino-1H-3-pyrazolyl)phenyl]-3-methyl-1-benzenesulfonamide (Compound 86). $^1$H NMR (400 MHz, DMSO-d6): δ 12.70 (s, 1H), 10.31 (s, 1H), 9.38 (s, 1H), 7.59 (d, J=6.8 Hz, 1H), 7.44-7.36 (m, 3H), 7.28 (t, J=7.6 Hz, 1H), 7.21 (t, J=7.6 Hz, 1H), 7.12 (d, J=7.6 Hz, 1H), 7.04 (d, J=8.0 Hz, 1H), 6.63 (s, 1H), 6.35 (s, 1H), 3.49 (br, 4H), 2.40 (br, 4H), 2.33 (s, 3H), 2.30 (s, 3H), 2.23 (s, 3H); MS (ES$^+$) m/z calcd. for $C_{26}H_{30}N_8O_2S$: 518.64; found: 519.1 (M+H$^+$).

N1-(3-5-[(6-[2-(dimethylamino)ethyl]amino-2-methyl-4-pyrimidinyl)amino]-1H-3-pyrazolylphenyl)-1-benzenesulfonamide (Compound 87). $^1$H NMR (400 MHz, DMSO-d6): δ 12.59 (s, 1H), 9.13 (s, 1H), 7.79 (d, J=7.2 Hz, 2H), 7.63-7.53 (m, 4H), 7.37-7.27 (m, 3H), 7.02 (d, J=8.0 Hz, 1H), 6.59 (s, 1H), 6.37-6.29 (m, 1H), 3.42-3.19 (m, 1H, overlapping with H$_2$O peak), 2.39 (t, J=6.8 Hz, 2H), 2.25 (s, 2H), 2.18 (s, 9H); MS(ES$^+$) m/z calcd. for $C_{24}H_{28}N_8O_2S$: 492.60; found: 493.2 (M+H$^+$).

N1-3-[5-(2-methyl-6-[(2-morpholinoethyl)amino]-4-pyrimidinylamino)-1H-3-pyrazolyl]phenyl-1-benzenesulfonamide (Compound 88). $^1$H NMR (400 MHz, DMSO-d6): δ 12.59 (s, 1H), 10.41 (s, 1H), 9.13 (s, 1H), 7.79 (d, J=7.2 Hz, 2H), 7.63-7.53 (m, 3H), 7.39-7.27 (m, 3H), 7.04 (d, J=8.0 Hz, 1H), 6.64 (s, 1H), 6.38 (s, 1H), 3.33 (br s, 4H), 2.40 (t, J=6.4 Hz, 2H), 2.25 (s, 3H), 2.18 (br s, 6H); MS (ES$^+$) m/z calcd. for $C_{26}H_{30}N_8O_3S$: 534.63; found: 535.1 (M+H$^+$).

N1-3-[5-(2-methyl-6-[(3-morpholinopropyl)amino]-4-pyrimidinylamino)-1H-3-pyrazolyl]phenyl-1-benzenesulfonamide (Compound 89). $^1$H NMR (400 MHz, DMSO-d6): δ 12.62 (s, 1H), 10.42 (s, 1H), 9.23 (s, 1H), 7.79 (d, J=7.2 Hz, 2H), 7.63-7.53 (m, 3H), 7.39-7.26 (m, 3H), 7.03 (d, J=7.6 Hz, 1H), 6.95 (s, 1H), 6.33 (s, 1H), 3.69 (br s, 4H), 3.24 (br s, 2H), 2.99-2.67 (m, 6H), 2.28 (s, 3H), 1.79 (br s, 2H); MS (ES$^+$) m/z calcd. for $C_{27}H_{32}N_8O_3S$: 548.66; found: 549.1 (M+H$^+$); HRMS (FAB) calcd. for $C_{27}H_{32}N_8O_3S$: 548.2318; found: 548.2321.

N1-[3-(5-[6-(4-hydroxypiperidino)-2-methyl-4-pyrimidinyl]amino-1H-3-pyrazolyl)phenyl]-1-benzenesulfonamide (Compound 90). $^1$H NMR (400 MHz, DMSO-d6): δ 12.72 (s, 1H), 10.43 (s, 1H), 9.32 (s, 1H), 7.80 (d, J=7.2 Hz, 2H), 7.63-7.53 (m, 3H), 7.39-7.28 (m, 3H), 7.04 (d, J=7.6 Hz, 1H), 6.34 (s, 1H), 4.78 (s, 1H), 3.96 (d, J=12.8 Hz, 2H), 3.75-3.69 (m, 1H), 3.17 (t, J=10.4 Hz, 2H), 2.34 (s, 3H), 1.78 (d, J=9.6 Hz, 2H), 1.39-1.23 (m, 2H); MS (ES$^+$) m/z calcd. for $C_{25}H_{27}N_7O_3S$: 505.59; found: 506.1 (M+H$^+$).

N1-3-[5-(6-[4-(2-hydroxyethyl)piperazino]-2-methyl-4-pyrimidinylamino)-1H-3-pyrazolyl]phenyl-1-benzenesulfonamide (Compound 91). $^1$H NMR (400 MHz, DMSO-d6): δ 12.83 (s, 1H), 10.44 (s, 1H), 9.56 (s, 1H), 7.79 (d, J=6.8 Hz, 2H), 7.63-7.53 (m, 3H), 7.37-7.28 (m, 3H), 7.03 (d, J=8.0 Hz, 1H), 6.59 (s, 1H), 6.37 (s, 1H), 3.56-3.49 (m, 8H), 2.50-2.45 (m, 4H), 2.30 (s, 3H); MS (ES$^+$) m/z calcd. for $C_{26}H_{30}N_8O_3S$: 534.63; found: 535.1 (M+H$^+$); HRMS (FAB) calcd. for $C_{26}H_{30}N_8O_3S$: 534.2162; found: 534.2166.

N1-[3-(5-[2-methyl-6-(4-methylpiperazino)-4-pyrimidinyl]amino-1H-3-pyrazolyl)phenyl]-1-butanesulfonamide (Compound 92). $^1$H NMR (400 MHz, DMSO-d6): δ 12.72 (s, 1H), 9.84 (s, 1H), 9.30 (s, 1H), 7.47-7.36 (m, 3H), 7.16 (d, J=6.8 Hz, 1H), 6.86 (s, 1H), 6.69 (s, 1H), 3.43 (br, 4H), 3.08 (t, J=7.6 Hz, 2H), 2.32 (br, 4H), 2.24 (s, 3H), 2.16 (s, 3H), 1.61 (tt, J=7.6, 7.6 Hz, 2H), 1.30 (qt, J=7.2, 7.6 Hz, 2H), 0.78 (t, J=7.2 Hz, 3H); MS (ES$^+$) m/z calcd. for $C_{23}H_{32}N_8O_2S$: 484.62; found: 485.1 (M+H$^+$).

N-[5-(tert-butyl)-3-isoxazolyl]-N'-4-[5-(6-[4-(2-hydroxyethyl)piperazino]-2-methyl-4-pyrimidinylamino)-1H-3-pyrazolyl]benzylurea (Compound 93a). MS (ES$^+$) m/z calcd. for $C_{29}H_{38}N_{10}O_3$: 574.69; found: 575.3 (M+H$^+$).

N-[5-(tert-butyl)-3-isoxazolyl]-N'-[4-(5-[2-methyl-6-(4-methylpiperazino)-4-pyrimidinyl]amino-1H-3-pyrazolyl)benzyl]urea (93b). $^1$H NMR (400 MHz, DMSO-d6): δ 12.70 (s, 1H), 9.49 (s, 1H), 9.31 (s, 1H), 7.66 (d, J=7.2 Hz, 2H), 7.34 (d, J=8.0 Hz, 2H), 7.01 (t, J=6.0 Hz, 1H), 6.69 (s, 1H), 6.46 (s, 1H), 6.37 (m, 1H), 4.33 (d, J=6.0 Hz, 2H), 3.48 (d, J=4.8 Hz, 4H), 2.36 (t, J=4.8 Hz, 4H), 2.28 (s, 3H), 2.20 (s, 3H), 1.26 (s, 9H); MS (ES$^+$) m/z calcd. for $C_{28}H_{36}N_{10}O_2$: 544.30; found: 545.3 (M+H$^+$).

N-[5-(tert-butyl)-3-isoxazolyl]-N'-(4-5-[(2-methyl-6-piperazino-4-pyrimidinyl)amino]-1H-3-pyrazolylbenzyl)urea (93c). $^1$H NMR (400 MHz, DMSO-d6): δ 12.69 (s, 1H), 9.52 (s, 1H), 9.33 (s, 1H), 7.65 (d, J=7.6 Hz, 2H), 7.33 (d, J=8.4 Hz, 2H), 7.08 (t, J=6.0 Hz, 1H), 6.50 (s, 1H), 6.46 (d, J=6.4 Hz, 1H), 6.36 (m, 1H), 4.32 (d, J=5.6 Hz, 2H), 3.53-3.49 (m, 4H, overlapping with DMSO peak), 2.91 (t, J=4.8 Hz, 4H), 2.28 (s, 3H), 1.25 (s, 9H); MS (ES$^+$) m/z calcd. for $C_{27}H_{34}N_{10}O_2$: 530.29; found: 531.3 (M+H$^+$).

N-[4-(5-[2-methyl-6-(4-methylpiperazino)-4-pyrimidinyl]amino-1H-3-pyrazolyl)phenyl]-N'-phenylurea (Compound 94). $^1$H NMR (400 MHz, DMSO-d6): δ 12.58 (s, 1H), 9.32 (s, 1H), 8.88 (s, 1H), 8.78 (s, 1H) 7.61 (d, J=8.8 Hz, 2H), 7.57 (d, J=4.4 Hz, 1H), 7.52 (d, J=8.8 Hz, 2H), 7.45-7.27 (m, 3H), 6.96 (t, J=7.2 Hz, 1H), 6.63 (s, 1H), 6.38 (s, 1H), 3.41 (br s, 6H), 2.37 (br s, 3H), 2.28 (s, 3H), 2.20 (s, 2H); MS (ES$^+$) m/z calcd. for $C_{26}H_{29}N_9O$: 483.25; found: 484.1 (M+H$^+$).

Benzyl-N-[4-(5-[2-methyl-6-(4-methylpiperazino)-4-pyrimidinyl]amino-1H-3-pyrazolyl)benzyl]carbamate (Compound 96). $^1$H NMR (300 MHz, DMSO-d6): δ 12.68 (s, 1H), 9.29 (s, 1H), 7.86 (t, J=6.0 Hz, 1H), 7.65 (d, J=7.2 Hz, 2H), 7.36-7.24 (m, 7H), 6.66 (s, 1H), 6.46 (d, 1H), 5.05 (s, 2H), 4.22 (d, J=6.0 Hz, 2H), 3.43-3.40 (m, 4H), 2.36-2.34 (m, 4H), 2.29 (s, 3H), 2.20 (s, 3H); MS (ES$^+$) m/z calcd. for $C_{28}H_{32}N_8O_2$: 512.26; found: 513.3 (M+H$^+$).

Benzyl-N-4-[5-(6-[4-(2-hydroxyethyl)piperazino]-2-methyl-4-pyrimidinylamino)-1H-3-pyrazolyl]benzylcarbamate (Compound 97). ¹H NMR (400 MHz, DMSO-d6): δ 12.72 (s, 1H), 9.35 (s, 1H), 7.90 (t, J=6.0 Hz, 1H), 7.67 (d, J=7.6 Hz, 2H), 7.42-7.36 (m, 5H), 7.33 (d, J=8.0 Hz, 2H), 6.69 (s, 1H), 6.47 (s, 1H), 5.07 (s, 2H), 4.48 (t, J=5.2 Hz, 1H), 4.24 (d, J=6.4 Hz, 2H), 3.57-3.52 (m, 6H), 2.52-2.44 (m, 6H, overlapped with DMSO), 2.31 (s, 3H); MS (ES⁺) m/z calcd. for $C_{28}H_{34}N_8O_3$: 542.27; found: 543.3 (M+H⁺).

(5-Methyl-3-isoxazolyl)methyl-N-4-[5-(6-[4-(2-hydroxyethyl)piperazino]-2-methyl-4-pyrimidinylamino)-1H-3-pyrazolyl]benzylcarbamate (Compound 98). ¹H NMR (300 MHz, DMSO-d6): δ 12.68 (s, 1H), 9.33 (s, 1H), 7.96 (t, J=6.0 Hz, 1H), 7.64 (d, J=8.1 Hz, 2H), 7.30 (d, J=8.4 Hz, 2H), 6.64 (s, 1H), 6.44 (s, 1H), 6.20 (s, 1H), 5.04 (s, 2H), 4.48-4.44 (m, 1H), 4.21 (d, J=6.3 Hz, 2H), 3.55-3.47 (m, 6H), 2.50-2.39 (m, 6H, overlapped with DMSO), 2.28 (s, 6H); MS (ES⁺) m/z calcd. for $C_{27}H_{33}N_9O_4$: 547.26; found: 570.3 (M+Na), 548.3 (M+H⁺).

(5-Methyl-3-isoxazolyl)methyl-N-[4-(5-[2-methyl-6-(4-methylpiperazino)-4-pyrimidinyl]amino-1H-3-pyrazolyl)benzyl]carbamate (Compound 99). ¹H NMR (400 MHz, DMSO-d6): δ 12.69 (s, 1H), 9.34 (s, 1H), 7.97 (t, J=6.0 Hz, 1H), 7.65 (d, J=8.0 Hz, 2H), 7.30 (d, J=8.4 Hz, 2H), 6.66 (s, 1H), 6.44 (s, 1H), 6.20 (s, 1H), 5.04 (s, 2H), 4.21 (d, J=6.0 Hz, 2H), 3.55 (br s, 4H), 3.15 (s, 1H), 2.39 (br s, 4H), 2.28 (s, 3H), 2.19 (s, 3H); MS (ES⁺) m/z calcd. for $C_{26}H_{31}N_9O_3$: 517.26; found: 518.3 (M+H⁺).

2-Pyridylmethyl-N-4-[5-(6-[4-(2-hydroxyethyl)piperazino]-2-methyl-4-pyrimidinylamino)-1H-3-pyrazolyl]benzylcarbamate (Compound 100). ¹H NMR (300 MHz, DMSO-d6): δ 12.71 (s, 1H), 9.34 (s, 1H), 8.62 (s, 1H), 8.56 (d, J=4.8 Hz, 1H), 7.94 (t, J=6.0 Hz, 1H), 7.80 (d, J=7.8 Hz, 1H), 7.67 (d, J=7.5 Hz, 2H), 7.45-7.41 (m, 1H), 7.33 (d, J=7.8 Hz, 2H), 6.68 (s, 1H), 6.47 (s, 1H), 5.12 (s, 2H), 4.48 (br s, 1H), 4.24 (d, J=6.0 Hz, 2H), 3.55-3.50 (m, 6H), 2.53-2.42 (m, 6H, overlapped with DMSO), 2.31 (s, 3H); MS (ES⁺) m/z calcd. for $C_{28}H_{33}N_9O_3$: 543.27; found: 544.3 (M+H⁺).

3-Pyridylmethyl-N-[4-(5-[2-methyl-6-(4-methylpiperazino)-4-pyrimidinyl]amino-1H-3-pyrazolyl)benzyl]carbamate (Compound 101). ¹H NMR (400 MHz, DMSO-d6): δ 12.70 (s, 1H), 9.32 (s, 1H), 8.59 (s, 1H), 8.52 (d, J=4.4 Hz, 1H), 7.92 (t, J=6.4 Hz, 1H), 7.78 (d, J=8.0 Hz, 1H), 7.64 (d, J=7.2 Hz, 2H), 7.42-7.38 (m, 1H), 7.30 (d, J=8.0 Hz, 2H), 6.68 (s, 1H), 6.45 (s, 1H), 5.08 (s, 2H), 4.21 (d, J=6.4 Hz, 2H), 3.48 (br s, 4H), 2.37 (br s, 4H), 2.28 (s, 3H), 2.20 (s, 3H); MS (ES⁺) m/z calcd. for $C_{27}H_{31}N_9O_2$: 513.26; found: 514.3 (M+H⁺).

N2-[2-methyl-6-(4-ethylpiperazino)-4-pyrimidinyl]-4-(4-amino-3-phenyl)-1,3-thiazol-2-amine (102). ¹H NMR (300 MHz, DMSO-d6): δ 7.43 (s, 1H), 7.23 (d, J=8.1 Hz, 2H), 6.58 (d, J=8.7 Hz, 2H), 6.04 (s, 1H), 5.24 (s, 1H), 3.48 (br s, 4H), 2.42-2.31 (m, 10H), 1.02 (t, J=7.2 Hz, 3H). MS (ES⁺) m/z Calcd for $C_{19}H_{22}ClN_7S$: 395.52; found: 396.1 (M+H⁺).

N-(5-methyl-3-isoxazolyl)-N'-[4-(2-[2-methyl-6-(4-methylpiperazino)-4-pyrimidinyl]amino-1,3-thiazol-5-yl)phenyl]urea (Compound 103). ¹H NMR (400 MHz, DMSO-d6): δ 11.15 (s, 1H), 9.46 (s, 1H), 8.92 (s, 1H), 7.67 (s, 1H), 7.50 (ABq, Δν_{AB}=13.4 Hz, J_{AB}=8.8 Hz, 4H), 6.55 (s, 1H), 6.04 (s, 1H), 3.50 (t, J=4.8 Hz, 4H), 2.41 (s, 3H), 2.37 (m, 7H), 2.21 (s, 3H); MS (ES⁺) m/z calcd. for $C_{24}H_{27}N_9O_2S$: 505.20; found: 506.2 (M+H⁺).

N-[5-(tert-butyl)-3-isoxazolyl]-N'-[4-(2-[2-methyl-6-(4-methylpiperazino)-4-pyrimidinyl]amino-1,3-thiazol-4-yl)phenyl]urea (Compound 104). ¹H NMR (400 MHz, DMSO-d6): δ 11.13 (s, 1H), 9.53 (s, 1H), 8.93 (s, 1H), 7.67 (s, 1H), 7.53-7.47 (m, 4H), 6.51 (s, 1H), 6.04 (s, 1H), 3.50 (br s, 4H), 2.41 (s, 3H), 2.36 (t, J=4.8 Hz, 4H), 2.21 (s, 3H), 1.30 (s, 9H). MS (ES⁺) m/z Calcd for $C_{27}H_{33}N_9O_2S$: 547.25; found: 548.3 (M+H⁺).

N-(3-chlorophenyl)-N'-(4-2-[(2-methyl-6-piperazino-4-pyrimidinyl)amino]-1,3-thiazol-5-ylphenyl)urea (108). ¹H NMR (400 MHz, DMSO-d6): δ 11.07 (s, 1H), 9.01 (s, 1H), 8.99 (s, 1H), 7.72-7.65 (m, 2H), 7.57-7.50 (m, 4H), 7.32-7.27 (m, 2H), 7.04-7.00 (m, 2H), 6.06 (s, 1H), 3.43 (br s, 4H, overlapping with water peak), 2.76 (t, J=4.8 Hz, 4H), 2.41 (s, 3H); MS (ES⁺) m/z calcd. for $C_{25}H_{25}ClN_8OS$: 520.16; found: 521.1 (M+H⁺).

N-[4-(2-[6-(4-aminopiperidino)-2-methyl-4-pyrimidinyl]amino-1,3-thiazol-5-yl)phenyl]-N'-phenylurea (109). ¹H NMR (400 MHz, DMSO-d6): δ 8.80 (s, 1H), 8.70 (s, 1H), 7.64 (s, 1H), 7.49-7.45 (m, 6H), 7.28 (t, J=7.6 Hz, 2H), 6.97 (t, J=7.2 Hz, 1H), 6.06 (s, 1H), 4.12 (d, J=12.0 Hz, 2H), 3.33 (br s, 2H, overlapping with water peak), 2.94 (t, J=11.6 Hz, 4H), 2.41 (s, 3H), 1.76 (d, J=10.0 Hz, 2H), 1.16 (d, J=10.4 Hz, 2H); MS (ES⁺) m/z calcd. for $C_{26}H_{28}N_8OS$: 500.21; found: 501.2 (M+H⁺).

N-4-[2-(6-[4-(aminomethyl)piperidino]-2-methyl-4-pyrimidinylamino)-1,3-thiazol-4-yl]phenyl-N'-phenylurea (110). ¹H NMR (400 MHz, DMSO-d6): δ 8.90 (s, 1H), 8.80 (s, 1H), 7.64 (s, 1H), 7.49-7.46 (m, 6H), 7.28 (t, J=7.6 Hz, 2H), 6.95 (t, J=6.4 Hz, 1H), 6.04 (s, 1H), 4.24 (s, 2H), 3.31 (br s, 2H, overlapping with water peak), 2.82 (t, J=11.6 Hz, 4H), 2.40 (s, 3H), 1.75-1.69 (m, 2H), 1.51 (br s, 1H), 1.06 (br s, 2H); MS (ES⁺) m/z calcd. for $C_{27}H_{30}N_8OS$: 514.23; found: 515.2 (M+H⁺).

N-(5-ethyl-3-isoxazolyl)-N'-(4-2-[(2-methyl-6-piperazino-4-pyrimidinyl)amino]-1,3-thiazol-5-ylphenyl)urea (111). ¹H NMR (300 MHz, DMSO-d6): δ 11.09 (s, 1H), 9.48 (s, 1H), 8.92 (s, 1H), 7.65 (s, 1H), 7.48 (ABq, Δν_{AB}=13.2 Hz, J_{AB}=9.0 Hz, 4H), 6.54 (s, 1H), 6.00 (s, 1H), 3.41 (br s, 4H), 2.71-2.66 (m, 6H), 2.39 (s, 3H), 1.20 (t, J=7.5 Hz, 3H); MS (ES⁺) m/z calcd. for $C_{24}H_{27}N_9O_2S$: 505.20; found: 506.2 (M+H⁺).

N-(5-ethyl-3-isoxazolyl)-N'-[4-(2-[6-(4-ethylpiperazino)-2-methyl-4-pyrimidinyl]amino-1,3-thiazol-5-yl)phenyl]urea (112). ¹H NMR (400 MHz, DMSO-d6): δ 11.12 (s, 1H), 9.48 (s, 1H), 8.95 (s, 1H), 7.66 (s, 1H), 7.48 (ABq, Δν_{AB}=16.4 Hz, J_{AB}=8.8 Hz, 4H), 6.55 (s, 1H), 6.05 (s, 1H), 3.50 (br s, 4H), 2.70 (q, J=7.6 Hz, 2H), 2.41-2.32 (m, 9H), 1.22 (t, J=7.6 Hz, 3H), 1.03 (t, J=7.2 Hz, 3H); MS (ES⁺) m/z calcd. for $C_{26}H_{31}N_9O_2S$: 533.23; found: 534.2 (M+H⁺).

N-(4-chlorophenyl)-N'-[4-(2-[6-(4-ethylpiperazino)-2-methyl-4-pyrimidinyl]amino-1,3-thiazol-5-yl)phenyl]urea (113). ¹H NMR (300 MHz, DMSO-d6): 11.10 (s, 1H), 8.84-8.81 (m, 2H), 7.63 (s, 1H), 7.49-7.43 (m, 6H), 7.32 (s, 1H), 7.29 (s, 1H), 6.03 (s, 1H), 3.48 (br s, 4H), 2.40-2.30 (m, 9H), 1.01 (t, J=7.2 Hz, 3H); MS (ES⁺) m/z calcd. for $C_{27}H_{29}ClN_8OS$: 548.19; found: 549.2 (M+H⁺).

N-(5-cyclopropyl-3-isoxazolyl)-N'-(4-2-[(2-methyl-6-piperazino-4-pyrimidinyl)amino]-1,3-thiazol-5-ylphenyl)urea (114). ¹H NMR (300 MHz, DMSO-d6): 11.10 (s, 1H), 9.47 (s, 1H), 8.34 (s, 1H), 7.65 (s, 1H), 7.48 (ABq, Δν_{AB}=13.8 Hz, J_{AB}=8.7 Hz, 4H), 6.47 (s, 1H), 6.01 (s, 1H), 3.44 (br s, 4H), 2.76 (br s, 4H), 2.39 (s, 3H), 2.13-2.04 (m, 1H), 1.06-0.99 (m, 2H), 0.89-0.84 (m, 2H); MS (ES⁺) m/z calcd. for $C_{25}H_{27}N_9O_2S$: 517.20; found: 518.2 (M+H⁺).

N-(5-cyclopropyl-3-isoxazolyl)-N'-[4-(2-[6-(4-ethylpiperazino)-2-methyl-4-pyrimidinyl]amino-1,3-thiazol-5-yl)phenyl]urea (115). ¹H NMR (400 MHz, DMSO-d6): 11.12 (s, 1H), 9.44 (s, 1H), 8.88 (s, 1H), 7.65 (s, 1H), 7.48 (ABq, Δν_{AB}=18.4 Hz, J_{AB}=8.8 Hz, 4H), 6.47 (s, 1H), 6.03 (s, 1H), 3.48 (br s, 4H), 2.40 (br s, 7H), 2.34 (q, J=7.2 Hz, 2H), 2.12-2.06 (m, 1H), 1.05-0.99 (m, 5H), 0.89-0.85 (m, 2H); MS (ES⁺) m/z calcd. for $C_{27}H_{31}N_9O_2S$: 545.23; found: 546.2 (M+H⁺).

N-[4-(2-[6-(4-acetylpiperazino)-2-methyl-4-pyrimidinyl] amino-1,3-thiazol-5-yl)phenyl]-N'-(5-ethyl-3-isoxazolyl) urea (116). ¹H NMR (400 MHz, DMSO-d6): δ 11.18 (s, 1H), 9.48 (s, 1H), 8.93 (s, 1H), 7.67 (s, 1H), 7.50 (ABq, $\Delta v_{AB}$=16.4 Hz, $J_{AB}$=8.8 Hz, 4H), 6.55 (s, 1H), 6.06 (s, 1H), 3.56-3.53 (m, 8H), 2.70 (q, J=7.6 Hz, 2H), 2.41 (s, 3H), 2.03 (s, 3H), 1.20 (t, J=7.6 Hz, 3H); MS (ES⁺) m/z calcd. for $C_{26}H_{29}N_9O_3S$: 547.21; found: 548.2 (M+H⁺).

N-(5-ethyl-3-isoxazolyl)-N'-(4-2-[(2-methyl-6-tetrahydro-1H-1-pyrrolyl-4-pyrimidinyl)amino]-1,3-thiazol-5-ylphenyl)urea (117). ¹H NMR (400 MHz, DMSO-d6): δ 11.04 (s, 1H), 9.50 (s, 1H), 8.94 (s, 1H), 7.63 (s, 1H), 7.48 (ABq, $\Delta v_{AB}$=14.8 Hz, $J_{AB}$=8.8 Hz, 4H), 6.54 (s, 1H), 5.76 (s, 1H), 3.32 (br s, 4H, overlapping with water peak), 2.80 (q, J=7.6 Hz, 2H), 2.38 (s, 3H), 1.90 (br s, 4H), 1.20 (t, J=7.6 Hz, 3H); MS (ES⁺) m/z calcd. for $C_{24}H_{26}N_8O_2S$: 490.19; found: 491.2 (M+H⁺).

N-[4-(2-[6-(4-aminopiperidino)-2-methyl-4-pyrimidinyl] amino-1,3-thiazol-5-yl)phenyl ]N'-(5-ethyl-3-isoxazolyl) urea (118). ¹H NMR (300 MHz, DMSO-d6): δ 10.55 (s, 1H), 10.11 (d, J=9.6 Hz, 2H), 8.38 (s, 1H), 7.78 (s, 1H), 7.52 (ABq, $\Delta v_{AB}$=18.0 Hz, $J_{AB}$=8.7 Hz, 4H), 6.55 (s, 1H), 6.10 (s, 1H), 4.26 (d, J=12.6 Hz, 2H), 3.26 (br s, 2H), 2.93 (t, J=12.3 Hz, 2H), 2.68 (q, J=7.5 Hz, 2H), 2.42 (s, 3H), 1.95 (d, J=11.4 Hz, 2H), 1.40 (d, J=10.8 Hz, 2H), 1.21 (t, J=7.5 Hz, 3H); MS (ES⁺) m/z calcd. for $C_{25}H_{29}N_9O_2S$: 519.22; found: 520.2 (M+H⁺).

N-[4-(2-[6-(3-aminotetrahydro-1H-1-pyrrolyl)-2-methyl-4-pyrimidinyl]amino-1,3-thiazol-5-yl)phenyl]N'-(5-ethyl-3-isoxazolyl)urea (119). ¹H NMR (400 MHz, DMSO-d6): δ 8.94 (s, 1H), 7.63 (s, 1H), 7.48 (ABq, $\Delta v_{AB}$=14.0 Hz, $J_{AB}$=8.4 Hz, 4H), 6.53 (s, 1H), 5.73 (s, 1H), 3.37 (br s, 7H, overlapping with water peak), 2.69 (q, J=7.2 Hz, 2H), 2.37 (s, 3H), 1.99 (br s, 1H), 1.67 (br s, 1H), 1.19 (t, J=7.6 Hz, 3H); MS (ES⁺) m/z calcd. for $C_{24}H_{27}N_9O_2S$: 505.20; found: 506.2 (M+H⁺).

Example 7

Synthesis of Compounds 120-125

Below is a general synthetic scheme for the synthesis of Compounds 120-125:

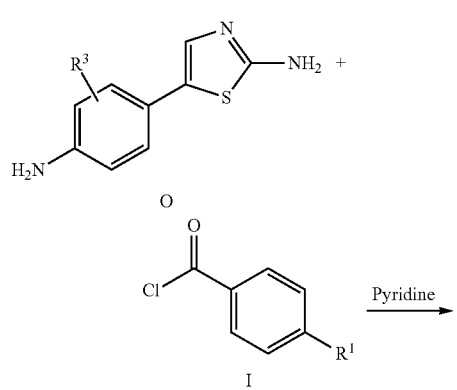

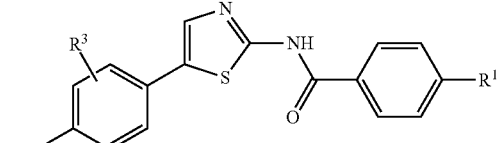

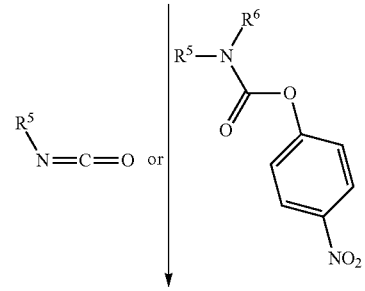

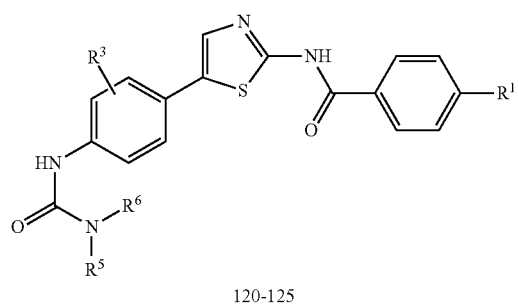

120-125

Step I. Synthesis of Compounds R:

To a solution of O (1.0 equiv) in pyridine at room temperature was added acyl chloride I (1.2 equiv). After 1 h of stirring at room temperature, the reaction was worked up as described for the synthesis of compounds J to yield compounds R. Only one of R is selected to show its NMR spectrum and Mass.

N1-[4-(4-aminophenyl)-1,3-thiazol-2-yl]-4-(4-methylpiperazino)benzamide. ¹H NMR (400 MHz, DMSO-d6): δ 9.96 (s, 1H), 7.87 (d, J=8.8 Hz, 2H), 7.74 (d, J=8.4 Hz, 2H), 7.37 (d, J=8.4 Hz, 2H), 7.31 (s, 1H), 7.07 (s, 2H), 7.01 (d, J=8.4 Hz, 2H), 3.34-3.29 (m, 4H, overlapped with water), 2.50-2.45 (m, 4H, overlapped with DMSO), 2.22 (s, 3H); MS (ES⁺) m/z calcd. for $C_{21}H_{23}N_5OS$: 393.16; found: 394.1 (M+H⁺).

Step II. Synthesis of Compounds 120-125:

Starting with R, the same procedures were followed as in the synthesis of Compounds 29-66 to yield Compounds 120-125.

N1-5-[4-([(5-methyl-3-isoxazolyl)amino]carbonylamino) phenyl]-1,3-thiazol-2-yl-4-(2-morpholinoethoxy)benzamide (Compound 120). ¹H NMR (400 MHz, DMSO-d6): δ 10.75 (s, 1H), 10.20 (s, 1H), 9.80 (s, 1H), 7.96 (d, J=8.8 Hz, 2H), 7.84-7.72 (m, 3H), 7.58 (d, J=8.8 Hz, 2H), 7.08 (d, J=8.8 Hz, 2H), 6.61 (s, 1H), 4.18 (t, J=5.6 Hz, 2H), 3.58 (t, J=4.4 Hz, 4H), 2.72 (t, J=5.6 Hz, 2H), 2.47 (t, J=4.4 Hz, 4H), 2.39 (s, 3H); MS (ES⁺) m/z calcd. for $C_{27}H_{28}N_6O_5S$: 548.18; found: 549.2 (M+H⁺).

Example 8

Synthesis of 46b Prodrug

Below is a general synthetic scheme for the synthesis of 46b prodrug:

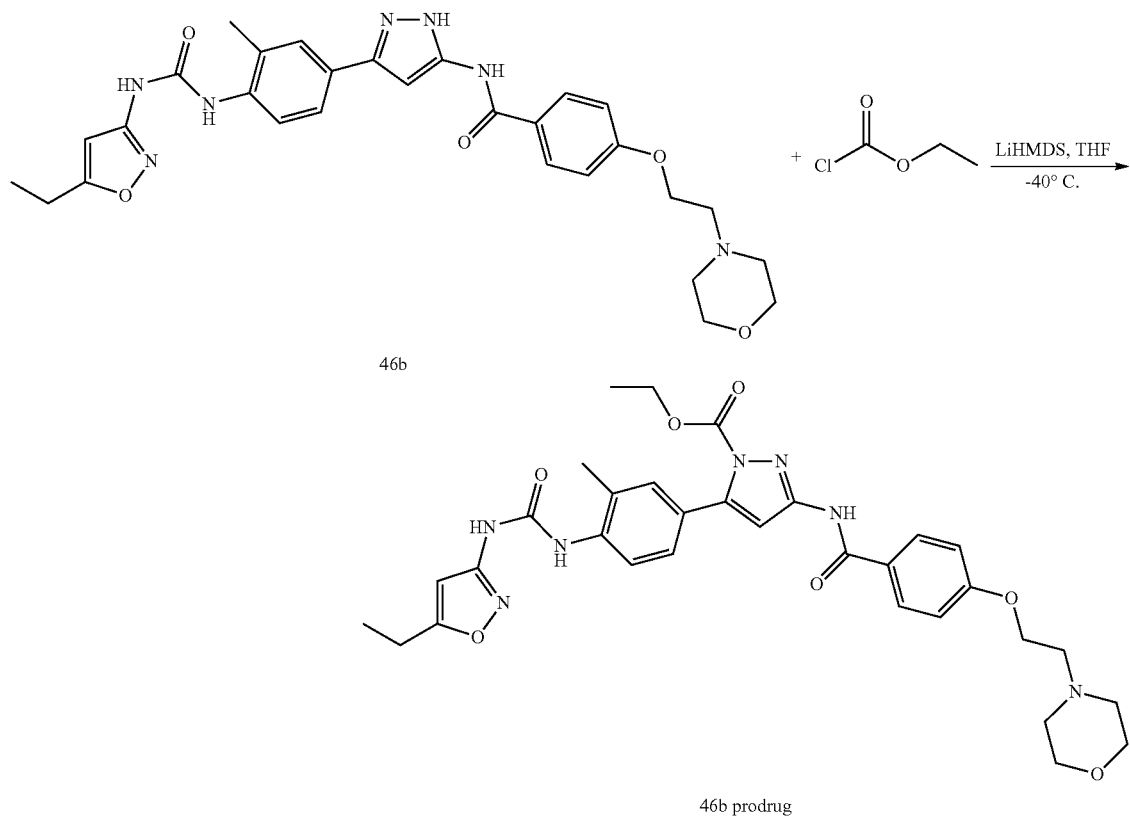

To a stirred solution of 46b (0.56 g, 1 mmol) in anhydrous THF (50 mL) at −40° C. was added lithium bis(trimethylsilyl) amide 1.0 M in THF (1.2 mL, 1.20 mmol) under argon. After the mixture was stirred at −40° C. for 10 min, ethyl chloroformate (0.13 g, 1.2 mmol) was added. The reaction was stirred at −40° C. for 30 min, and carefully quenched with water (20 mL). The mixture was diluted with ethyl acetate (100 mL). The organic layers were separated, washed with brine, dried over magnesium sulfate, concentrated and purified by flash chromatography on silica gel with 4% $CH_3OH/CH_2Cl_2$ to give 46b Prodrug as an off-white solid.

5-{4-[3-(5-Ethyl-isoxazol-3-yl)-ureido]-3-methyl-phenyl}-3-[4-(2-morpholin-4-yl-ethoxy)-benzoylamino]-pyrazole-1-carboxylic acid ethyl ester (46b Prodrug). $^1H$ NMR (400 MHz, $CDCl_3$): δ 9.47 (s, 1H), 9.37 (bs, 2H), 8.09 (d, J=8.8 Hz, 1H), 7.91 (d, J=8.8 Hz, 2H), 7.32-7.28 (m, 2H), 7.16 (s, 1H), 6.94 (d, J=8.8 Hz, 2H), 6.10 (bs, 1H), 4.33 (q, J=7.0 Hz, 2H), 4.15 (t, J=5.6 Hz, 2H), 3.79-3.68 (m, 4H), 2.82 (t, J=5.8 Hz, 2H), 2.77 (q, J=7.6 Hz, 2H) 2.66-2.52 (m, 4H), 2.39 (s, 3H), 1.31 (t, J=7.4 Hz, 3H), 1.24 (t, J=7.0 Hz, 3H); MS ($ES^+$) m/z calcd. for $C_{32}H_{37}N_7O_7$: 631.28; found: 632.2 (M+H$^+$).

Example 9

Oral Bioavailability (F %) of Parent Compound and its Prodrug

46b Prodrug, formulated in DMSO/PEG400 (20/80, v/v), was administered orally to rats (10 mg/Kg) in pharmacokinetic studies. The conversion of the compounds of 46b Prodrug into the corresponding parent compound (46b) was monitored in plasma by HPLC/MS/MS analysis at 15 and 30 min, 1, 2, 4, 6, 8, and 24 h post-dosing. All blood samples were taken from the jugular vein and centrifugated to obtain plasma.

Oral bioavailability, presented as a percentage (F %), was calculated by dividing the oral AUC value of the parent compound after the prodrug being administered by the average IV AUC value of the parent compound after its being administered following dose normalization.

The results are shown in the table below:

| Compound | Identification or Code | F % |
|---|---|---|
| N-(5-{4-[3-(5-Ethyl-isoxazol-3-yl)-ureido]-3-methyl-phenyl}-2H-pyrazol-3-yl)-4-(2-morpholin-4-yl-ethoxy)-benzamide | Parent compound (46b) | 8 |

| Compound | Identification or Code | F % |
|---|---|---|
| 5-{4-[3-(5-Ethyl-isoxazol-3-yl)-ureido]-3-methyl-phenyl}-3-[4-(2-morpholin-4-yl-ethoxy)-benzoylamino]-4,5-dihydro-pyrazole-1-carboxylic acid ethyl ester | 46b prodrug | 20 |

Example 10

Inhibiting FLT3 Activity

GST-FLT3-KD$^{WT}$ containing the FLT3 kinase catalytic domain (residues Y567~S993) were expressed in Sf9 insect cells transfected the baculovirus containing pBac-PAK8-GST-FLT3-KD plasmid. The FLT3$^{WT}$ Kinase-Glo assays were carried out in 96-well plates at 30° C. for 4 hrs and tested compound in a final volume of 50 μl including the following components: 75 ng GST-FLT3-KD$^{WT}$ proteins, 25 mM HEPES, pH 7.4, 4 mM MnCl$_2$, 10 mM MgCl$_2$, 2 mM DTT, 0.02% Triton X-100, 0.1 mg/ml bovine serum albumin, 25 μM Her2 peptide substrate, 0.5 mM Na$_3$VO$_4$, and 1 μM ATP. Following incubation, 50 μl Kinase-Glo Plus Reagent (Promega, Madison, Wis., USA) was added to each well and the mixture was incubated at 25° C. for 20 min. A 70-μL aliquot of each reaction mixture was transferred to a black microtiter plate and the luminescence was measured on Wallac Vector 1420 multilabel counter (PerkinElmer, Shelton, Conn., USA).

Multiple compounds were tested. Unexpectedly, Compounds 2, 6, 11, 12, 15, 24, 30, 32, 37, 41, 43, 44, 47, 49, 51, 57, 60, 61a, 68, 70, 73, 75, 77, 80, 82, 85, 96, 97, 99, 101, 102, 112, and 119 showed low IC$_{50}$ values between 1-20 nM.

Example 11

Inhibiting VEGFR 1/2 Activity

The recombinant GST-VEGFR1 (residues R781-I1338) or GST-VEGFR2 (residues V789-V1356) containing kinase domain were expressed in Sf9 insect cells. The kinase assay were carried out in 96-well plates with tested compound in a final volume of 50 μl reaction at 30° C. for 120 minutes with following components: 25 mM HEPES pH 7.4, 10 mM MgCl$_2$, 4 mM MnCl$_2$, 0.5 mM Na3VO4, 2 mM DTT, 0.02% Triton X100, 0.01% BSA, 1 μM ATP, 2 μM polyGlu4:Tyr peptide, 50~100 ng recombinant VEGFR1 or VEGFR2. Following incubation, 50 μl Kinase-Glo Plus Reagent (Promega, Madison, Wis., USA) was added to each well and the mixture was incubated at 25° C. for 20 min. A 70-μL aliquot of each reaction mixture was transferred to a black microtiter plate and the luminescence was measured on Wallac Vector 1420 multilabel counter (PerkinElmer, Shelton, Conn., USA).

Multiple compounds were tested in the VEGFR1 assay. Compounds 12, 15, 24, 32, 37, 41, 43, 44, 68, 70, 73, 75, 82, 85, 96, 46b, 46c, 59d, 62b, 62d, 112, and 119 unexpectedly showed IC$_{50}$ values lower than 1 μM. Among them, Compounds 37, 41, 43, 44, 70, 73, 82, 46c, 62b, 112, and 119 showed IC$_{50}$ values lower than 100 nM.

Multiple compounds were also tested in the VEGFR2 assay. Compounds 6, 12, 15, 24, 30, 32, 37, 41, 43, 44, 47, 51, 57, 60, 61a, 68, 70, 73, 75, 82, 85, 96, 97, 107, 46b, 46c, 59d, 62b, 62d, 112, and 119 unexpectedly showed IC$_{50}$ values lower than 1 μM. Among them, Compounds 6, 12, 15, 24, 68, 70, 73, 75, 82, 85, 96, 97 and 107 showed IC$_{50}$ values between 55 nM and 400 nM; and Compounds 30, 32, 37, 41, 43, 44, 47, 51, 57, 60, 61a, 46c, 59d, 62b, 62d, 112, and 119 showed IC$_{50}$ values between 1-55 nM.

Example 12

Inhibiting Aurora Kinase A Activity

The recombinant GST-Aurora A (residues S123-S401) containing kinase domain were expressed in Sf9 insect cells. The kinase assay were carried out in 96-well plates with tested compound in a final volume of 50 μl reaction at 37° C. for 90 minutes with following components: 50 mM Tris-HCl pH 7.4, 10 mM NaCl, 10 mM MgCl2, 0.01% BSA, 5 μM ATP, 1 mM DTT and 15 μM tetra(LRRASLG) peptide, and 150 ng recombinant Aurora A. Following incubation, 50 μl Kinase-Glo Plus Reagent (Promega, Madison, Wis., USA) was added to each well and the mixture was incubated at 25° C. for 20 min. A 70-μL aliquot of each reaction mixture was transferred to a black microtiter plate and the luminescence was measured on Wallac Vector 1420 multilabel counter (PerkinElmer, Shelton, Conn., USA).

Multiple compounds were tested. It was unexpected that Compounds 10, 12, 15, 30, 32, 43, 44, 47, 61a, 70, 85, 103, 107, 46b, 46c, 112, and 119 showed IC$_{50}$ values lower than 1 μM. Among them, Compounds 10, 32, 43, 44, 102, 120, 46b, 46c, 112, and 119 showed IC$_{50}$ values lower than 200 nM.

Example 13

In vitro Anticancer Activity (Cell Lines and MTS Cell Viability Assay)

The leukemias cell lines MOLM-13, MV4:11, RSV4:11, MOLT-4, U937, and K562 were purchased from American Type Culture Collection (ATCC, Manassas, Va., USA). The non-leukemias cell lines HCC827, H1975, NCIH460, A431, Huh7, SF268, MCF-7, HCT-116, and normal human fetal fibroblast cell line Detriot 551 were purchased from American Type Culture Collection (ATCC, Manassas, Va., USA). All leukemias cell lines and HCC827, H1975, NCIH460, A431 were maintained in RPMI 1640 medium supplemented with 10% fetal bovine serum (FBS), 10 U/ml penicillin, and 10 g/ml streptomycin at 37° C. and 5% CO$_2$. The cell lines Huh7, SF268, MCF-7, and Detroit 551 were cultured in DMEM medium supplemented with 10% FBS, 0.01% nonessential amino acids, 10 U/ml penicillin, and 10 g/ml streptomycin. HCT-116 were cultured in McCoy's 5A medium supplemented with 10% FBS, 0.01% nonessential amino acids, 10 U/ml penicillin, and 10 g/ml streptomycin. To determine cell viability after drug treatment, assays were performed by seeding 10,000 cells (leukemias cell lines) or 2,500 cells (non-leukemias cell lines) per well in a 96-well culture plate. After 16 h, cells were then treated with vehicle or various concentrations of compound in medium for 72 h. Viable cells were quantitated using the MTS method (Promega, Madison, Wis., USA) according to the manufacturer's recommended protocol. The results were determined by measuring the absorbance at 490 nm using a plate reader (Victor2; PerkinElmer, Shelton, Conn., USA). The GI$_{50}$ value was defined as the amount of compound that caused 50% reduction in cell viability in comparison with DMSO-treated (vehicle) control and was calculated using Prism version 4 software (GraphPad, San Diego, Calif., USA).

Multiple compounds were tested against MOLM-13. It was unexpected that, in the MTS cell viability assay, Compounds 2, 6, 10, 11, 12, 15, 24, 30, 32, 37, 41, 43, 44, 47, 49, 51, 57, 60, 61a, 68, 70, 73, 75, 77, 80, 82, 85, 96, 97, 99, 101, 103, 120, 46b, 46c, 59d, 62b, 62d, 112, and 119 inhibited the growth of MOLM-13 cell with $GI_{50}$ values lower than 210 nM. Among them, Compounds 10, 11, 12, 15, 24, 82, 85, and 120 showed $GI_{50}$ values between 10-210 nM; and Compounds 2, 6, 30, 32, 37, 41, 43, 44, 47, 49, 51, 57, 60, 61a, 68, 70, 73, 75, 77, 80, 96, 97, 99, 101, 103, 46b, 46c, 59d, 62b, 62d, 112, and 119 showed $GI_{50}$ values between 1-10 nM.

Representative $IC_{50}$ and $GI_{50}$ values obtained in Examples 10-13 are shown in the table below:

| Compd | IC$_{50}$ (nM) | | | | GI$_{50}$ (nM) |
| --- | --- | --- | --- | --- | --- |
| | wt-FLT3 | VEGFR1 | VEGFR2 | Aurora A | MOLM-13 Cell |
| 46b | 27 | 290 | 151 | 22 | 1 |
| 46c | 38 | 53 | 37 | 41 | 2 |
| 59d | 21 | 342 | 45 | ND | 6 |
| 62b | 26 | 29 | 37 | >1,000 | 2 |
| 62d | 38 | 180 | 23 | ND | 3 |
| 112 | 15 | 20 | 25 | 32 | 2 |
| 119 | 14 | 63 | 7 | 38 | 3 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

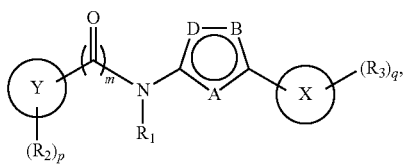

(I)

wherein
A is CR', B is N or NR, and D is N or NR, in which R is H or C(O)OR$_f$ and R' is H or alkyl, R$_f$ being C$_1$-C$_6$ alkyl, aryl, or cycloalkyl;
X is phenylene;
Y is arylene or heteroarylene;
R$_1$ is H or alkyl;
R$_2$ is alkyl, heterocyclyl, or alkoxy when p is 1 and each of the R$_2$ groups, independently, is alkyl, heterocyclyl, or alkoxy when p is 2 or 3;
R$_3$ is NR$_a$C(O)R$_b$, CR$_a$R$_b$NR$_c$C(O)NR$_d$R$_e$, NR$_a$S(O$_2$)R$_b$, NR$_a$C(O)NR$_b$R$_c$, NR$_a$C(O)OR$_b$, or CR$_a$R$_b$NR$_c$C(O)OR$_d$ when q is 1; and each of the R$_3$ groups, independently, is amino, halo, alkyl, NR$_a$C(O)R$_b$, CR$_a$R$_b$NR$_c$C(O)NR$_d$R$_e$, NR$_a$S(O$_2$)R$_b$, NR$_a$C(O)NR$_b$R$_c$, NR$_a$C(O)OR$_b$, or CR$_a$R$_b$NR$_c$—C(O)OR$_d$ when q is 2 or 3;

in which each of R$_a$, R$_b$, R$_c$, R$_d$, and R$_e$, independently, is H, alkyl, cyclyl, heterocyclyl, aryl, heteroaryl, arylalkyl, or heteroalkyl;
m is 1;
p is 1, 2, 3; and
q is 1, 2, 3.
2. The compound of claim 1, wherein A is CH, R is C(O) OR$_f$, in which R$_f$ is C$_1$-C$_6$ alkyl, aryl, or cycloalkyl.
3. The compound of claim 2, R$_f$ is C$_1$-C$_6$ alkyl.
4. The compound of claim 1, wherein Y is arylene and R$_1$ is H.
5. The compound of claim 4, wherein Y is phenylene.
6. The compound of claim 1, wherein Y is heteroarylene and R$_1$ is H.
7. The compound of claim 6, wherein Y is pyrimidinylene.
8. A compound, wherein the compound is
N1-[3-(4-aminophenyl)-1H-5-pyrazolyl]-4-(4-methylpiperazino) benzamide;
N1-3-[3-(benzoylamino)phenyl]-1H-5-pyrazolyl-4-(4-methylpiperazino) benzamide;
N1-(3-3-[(phenylsulfonypl)amino]phenyl-1H-5-pyrazolyl)-4-(4-methylpiperazino)benzamide;
N1-(4-methyl-3-{4-[({[(5-methyl-3-isoxazolyl)amino] carbonyl}amino) methyl]phenyl}-1H-5-pyrazolyl)-4-(4-methylpiperazino)benzamide;
N1-(3-4-[([5-(tert-butyl)-3-isoxazolyl]aminocarbonyl) amino]phenyl-1H-5-pyrazolyl)-4-(2-morpholinoethoxy)benzamide;
N1-(3-4-[([5-(tert-butyl)-3-isoxazolyl]aminocarbonyl) amino]-3-methylphenyl-1H-5-pyrazolyl)-4-[(4-methylpiperazino)methyl]benzamide;
N1-[3-(4-[([5-(tert-butyl)-3-isoxazolyl]aminocarbonyl) amino]methylphenyl)-1H-5-pyrazolyl]-4-[(4-methylpiperazino)methyl]benzamide;
Phenyl-N-[4-(5-[4-(4-methylpiperazino)benzoyl]amino-1H-3-pyrazolyl)phenyl]carbamate;
(5-Methyl-3-isoxazolyl)methyl-N-[4-(5-[4-(2-morpholinoethoxy)benzoyl]amino-1H-3-pyrazolyl)benzyl]carbamate;
N1-[3-(5-[2-methyl-6-(4-methylpiperazino)-4-pyrimidinyl]amino-1H-3-pyrazolyl)phenyl]-1-benzenesulfonamide;
N-[5-(tert-butyl)-3-isoxazolyl]-N'-4-[5-(6-[4-(2-hydroxyethyl)piperazino]-2-methyl-4-pyrimidinylamino)-1H-3-pyrazolyl]benzylurea;
(5-Methyl-3-isoxazolyl)methyl-N-4-[5-(6-[4-(2-hydroxyethyl)piperazino]-2-methyl-4-pyrimidinylamino)-1H-3-pyrazolyl]benzylcarbamate;
N-(5-methyl-3-isoxazolyl)-N'-[4-(2-[2-methyl-6-(4-methylpiperazino)-4-pyrimidinyl]amino-1,3-thiazol-5-yl) phenyl]urea;
N1-5-[4-([(5-methyl-3-isoxazolyl)amino]carbonylamino) phenyl]-1,3-thiazol-2-yl-4-(2-morpholinoethoxy)benzamide;
N-(5-{4-[3-(5-Ethyl-isoxazol-3-yl)-ureido]-3-methyl-phenyl}-2H-pyrazol-3-yl)-4-(2-morpholin-4-yl-ethoxy)-benzamide;
5-{4-[3-(5-Ethyl-isoxazol-3-yl)-ureido]-3-methyl-phenyl}-3-[4-(2-morpholin-4-yl-ethoxy)-benzoylamino]-pyrazole-1-carboxylic acid ethyl ester;
N-(5-{4-[3-(5-Cyclopropyl-isoxazol-3-yl)-ureidomethyl]-phenyl}-2H-pyrazol-3-yl)-4-(4-methyl-piperazin-1-ylmethyl)-benzamide;
N-(5-{4-[3-(5-Cyclopropyl-isoxazol-3-yl)-ureidomethyl]-phenyl}-2H-pyrazol-3-yl)-4-(2-morpholin-4-yl-ethoxy)-benzamide;

N-(5-{4-[3-(5-Ethyl-isoxazol-3-yl)-ureidomethyl]-phenyl}-2H-pyrazol-3-yl)-4-(4-methyl-piperazin-1-ylmethyl)-benzamide;

N1-(3-4-[([(5-cyclopropyl-3-isoxazolyl)amino]carbonylamino)methyl]phenyl-1H -5-pyrazolyl)-4-[(4-methylpiperazino)methyl]benzamide;

1-(5-Ethyl-isoxazol-3-yl)-3-(4-{2-[6-(4-ethyl-piperazin-1-yl)-2-methyl-pyrimidin-4-ylamino]-thiazol-5-yl}-phenyl)-urea; or 1-(4-{2-[6-(3-Amino-pyrrolidin-1-yl)-2-methyl-pyrimidin-4-ylamino]-thiazol-5-yl}-phenyl)-3-(5-ethyl-isoxazol-3-yl)-urea.

9. A pharmaceutical composition comprising a pharmaceutically acceptable carrier and a compound of claim 1.

10. The compound of claim 1, wherein q is 1.

11. A compound of formula (I):

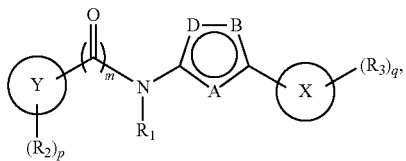

wherein

A is CH, B is NH, and D is N;

X is phenylene; Y is pyrimidinylene;

$R_1$ is H or alkyl;

$R_2$ is alkyl, halo, heteroalkyl, alkoxyalkyl, heterocyclyl, alkoxy, or amino;

$R_3$ is alkyl, halo, amino, $C(O)NR_aR_b$, $CR_aR_bNR_cC(O)NR_dR_e$, $CR_aR_bNR_cC(O)OR_d$, $CR_aR_bNR_cS(O)R_d$, $CR_aR_bNR_cS(O_2)R_d$, $NR_aR_b$, $NR_aC(O)NR_bR_c$, $NR_aS(O_2)R_b$, $NR_aC(O)R_b$, $NR_aC(O)OR_b$, or $S(O_2)NR_aR_b$, in which each of $R_a$, $R_b$, $R_c$, $R_d$, and $R_e$, independently, is H, alkyl, cyclyl, heterocyclyl, aryl, heteroaryl, arylalkyl, or heteroalkyl;

m is 0;

p is 0, 1, 2, 3; and q is 1, 2, 3.

12. A compound of formula (I):

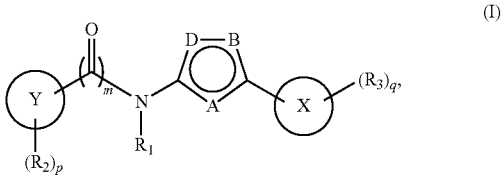

wherein

A is S, B is CR', and D is N, in which R' is H or alkyl;

X is phenylene; Y is pyrimidinylene;

$R_1$ is H or alkyl;

$R_2$ is alkyl, halo, heteroalkyl, alkoxyalkyl, heterocyclyl, alkoxy, or amino;

$R_3$ is alkyl, halo, amino, $NR_aR_b$, $NR_aC(O)NR_bR_c$, $NR_aS(O_2)R_b$, or $NR_aC(O)R_b$, in which each of $R_a$, $R_b$, and $R_c$, independently, is H, alkyl, cyclyl, heterocyclyl, aryl, heteroaryl, arylalkyl, or heteroalkyl;

m is 0;

p is 0, 1, 2, 3; and q is 1,2,3.

13. The compound of claim 11, wherein $R_1$ is H.

14. The compound of claim 12, wherein $R_1$ is H.

* * * * *